United States Patent
Kaufman et al.

(10) Patent No.: US 9,260,696 B2
(45) Date of Patent: Feb. 16, 2016

(54) METHOD FOR DEVELOPING NATURAL KILLER CELLS FROM STEM CELLS

(71) Applicants: Dan S. Kaufman, Minneapolis, MN (US); David A. Knorr, Minneapolis, MN (US)

(72) Inventors: Dan S. Kaufman, Minneapolis, MN (US); David A. Knorr, Minneapolis, MN (US)

( * ) Notice: Subject to any disclaimer, the term of this patent is extended or adjusted under 35 U.S.C. 154(b) by 176 days.

(21) Appl. No.: 13/868,785

(22) Filed: Apr. 23, 2013

(65) Prior Publication Data

US 2013/0287751 A1 Oct. 31, 2013

Related U.S. Application Data

(60) Provisional application No. 61/637,592, filed on Apr. 24, 2012.

(51) Int. Cl.
| | |
|---|---|
| *C12N 5/071* | (2010.01) |
| *C12N 5/02* | (2006.01) |
| *C12N 5/0783* | (2010.01) |
| *A61K 35/17* | (2015.01) |
| *A61K 35/545* | (2015.01) |

(52) U.S. Cl.
CPC .............. *C12N 5/0646* (2013.01); *A61K 35/17* (2013.01); *A61K 35/545* (2013.01); *C12N 2501/125* (2013.01); *C12N 2501/2303* (2013.01); *C12N 2501/2307* (2013.01); *C12N 2501/2315* (2013.01); *C12N 2501/26* (2013.01); *C12N 2502/1171* (2013.01); *C12N 2506/02* (2013.01); *C12N 2506/45* (2013.01); *C12N 2527/00* (2013.01)

(58) Field of Classification Search
None
See application file for complete search history.

(56) References Cited

U.S. PATENT DOCUMENTS

| 8,372,642 B2 | 2/2013 | Rajesh et al. | |
|---|---|---|---|
| 8,513,012 B2 | 8/2013 | Daigh | |
| 2013/0287751 A1* | 10/2013 | Kaufman | A61K 35/17 424/93.71 |

FOREIGN PATENT DOCUMENTS

WO WO 2011/068896 6/2011

OTHER PUBLICATIONS

Knorr, et al., "Clinical-scale derivation of natural killer cells from human pluripotent cells for cancer therapy", *Stem Cells Translational Medicine*, 2:274-283, 2013.
Knorr, et al., "Differentiation of human natural killer cells from pluripotent stem cells in a feeder free system amenable to clinical translation", *Blood (ASH Annual Meeting Abstracts)*, 116:Abstract 107, 2010.
Knorr, et al., "Engineered human embryonic stem cell-derived lymphocytes to study in vivo trafficking and immunotherapy", *Stem Cells and Development*, 22(13):1861-9, 2013.
Knorr, et al., "Pluripotent stem cell-derived natural killer cells for cancer therapy", *Transl Res.*, 156(3):147-154, 2010.
Ng, et al., "A protocol describing the use of a recombinant protein-based, animal product-free medium (APEL) for human embryonic stem cell differentiation as spin embryoid bodies", *Nature Protocols*, 3:768-776, 2008.
Ni, et al., "Human pluripotent stem cells produce natural killer cells that mediate anti-HIV-1 activity by utilizing diverse cellular mechanisms", *Journal of Virology*, 85(1):43-50, 2011.
PCT International Search Report and Written Opinion, issued in International Application No. PCT/US2013/037782, mailed Jun. 28, 2013.
Tabatabaei-Zavareh, et al., "Characterization of developmental pathway of natural killer cells from embryonic stem cells in vitro", *PLoS one*, 2(2):e232, 2007.
Woll, et al., "Human embryonic stem cell-derived NK cells acquire functional receptors and cytolytic activity", *Journal of Immunology*, 175:5095-5103, 2005.
Woll, et al., "Human embryonic stem cells differentiate into a homogeneous population of natural killer cells with potent in vivo antitumor activity", *Blood*, 113(24):6094-6101, 2009.

* cited by examiner

*Primary Examiner* — Michael Burkhart
(74) *Attorney, Agent, or Firm* — Parker Highlander PLLC

(57) ABSTRACT

A method for producing NK cells from pluripotent stem cells, which includes culturing pluripotent stem cells in a first serum-free medium, aggregating the undifferentiated stem cells to form embryoid bodies, which are cultured to produce hematopoietic precursor cells, and culturing the precursor cells in a serum-free medium to produce the NK cells. Methods for using such NK cells, e.g., in the treatment of cancer and infectious disease are also provided.

17 Claims, 24 Drawing Sheets

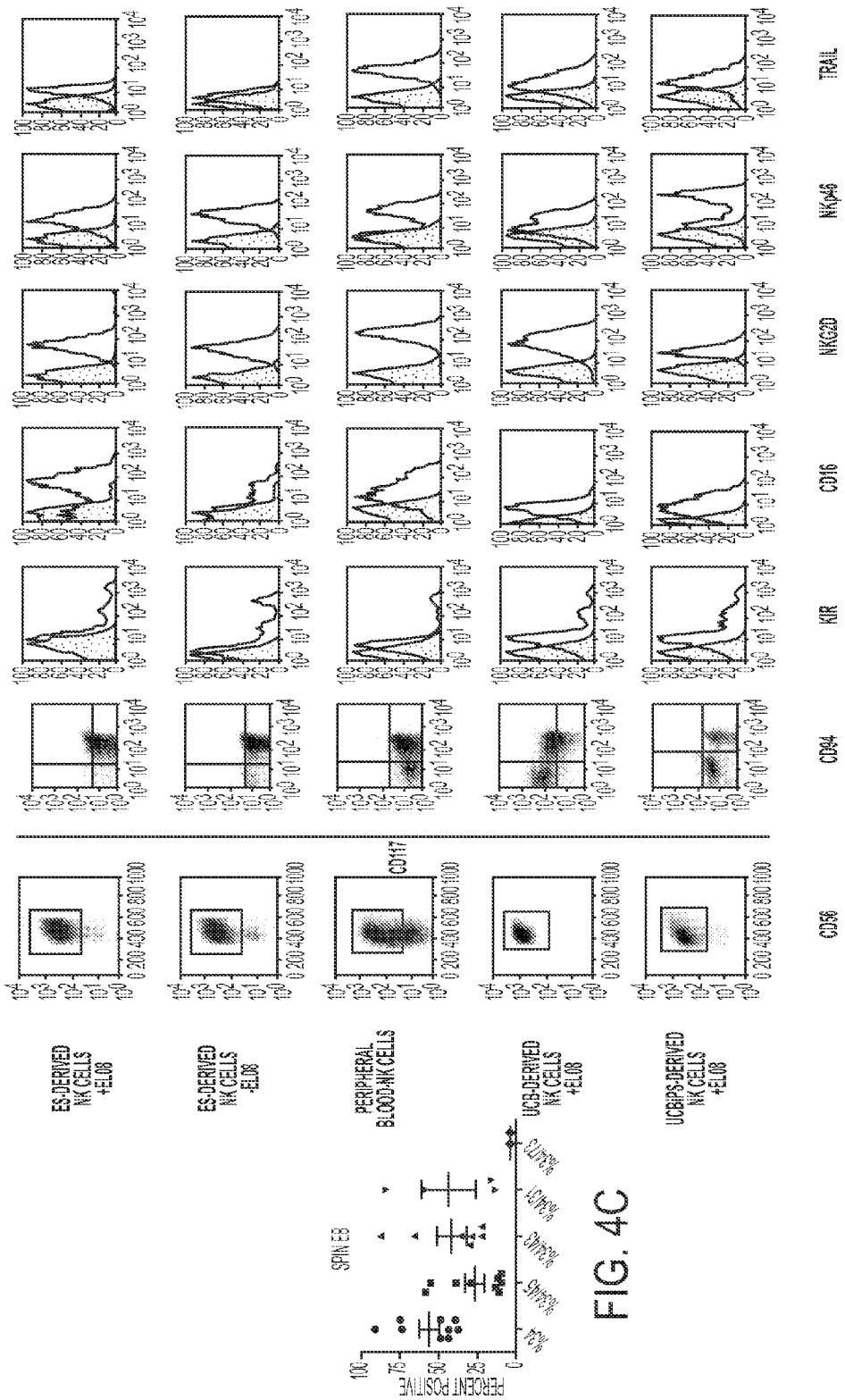

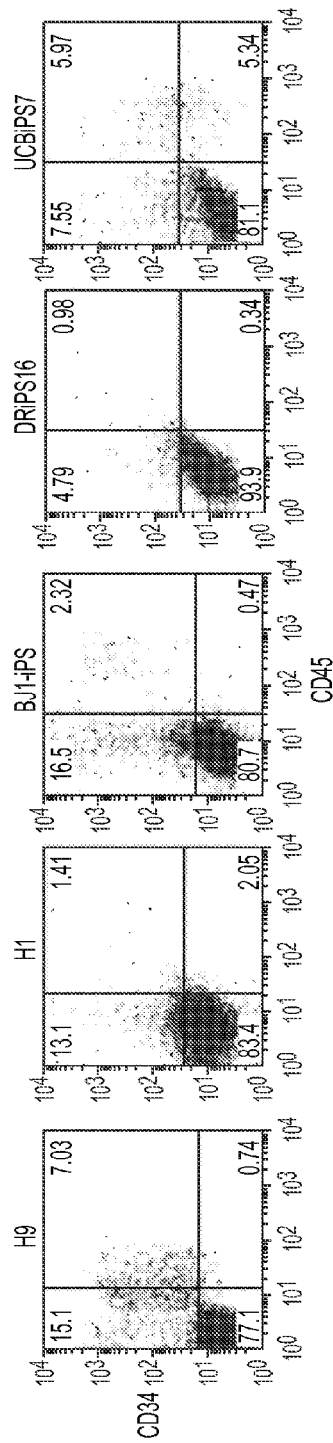
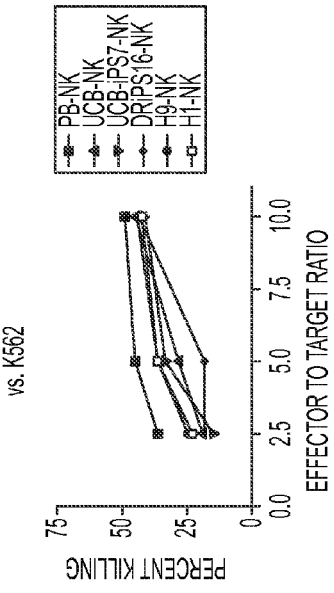
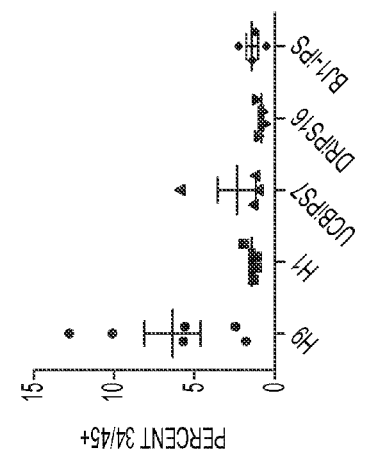
FIG. 8A
FIG. 8B
FIG. 8C

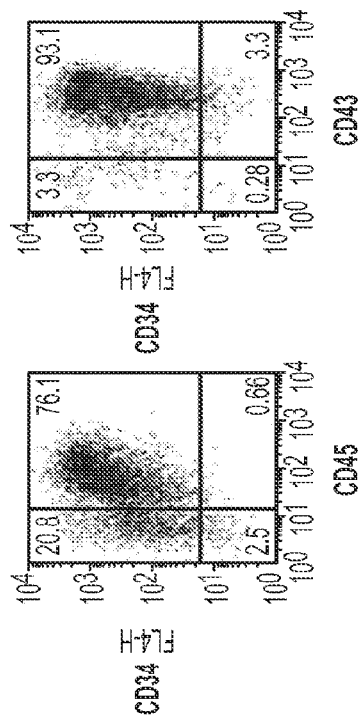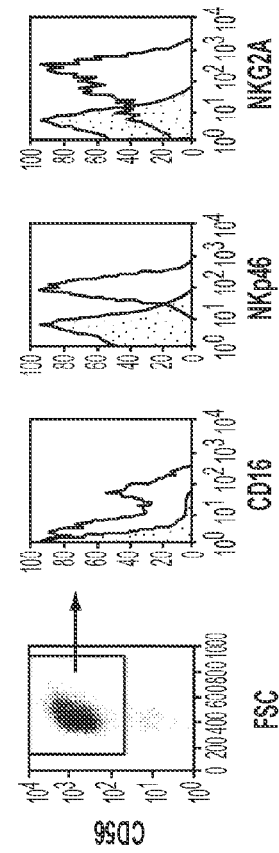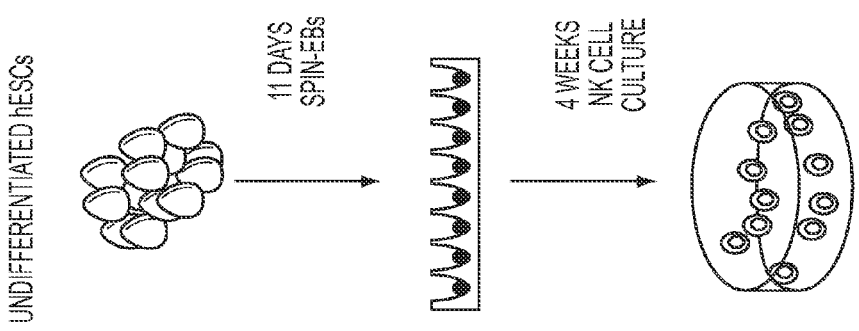

METHOD FOR DEVELOPING NATURAL KILLER CELLS FROM STEM CELLS

This application claims the benefit of U.S. Provisional Patent Application No. 61/637,592, filed Apr. 24, 2012, the entirety of which is incorporated herein by reference.

The invention was made with government support under Grant Nos. RO1 HL77923, T32 HD060536, and T32 GM008244 awarded by the National Institutes of Health. The government has certain rights in the invention.

BACKGROUND OF THE INVENTION

1. Field of the Invention

The present invention relates generally to the field of stem cell differentiation. More particularly, it concerns a method for developing natural killer cells that can be used in killing cancerous cells and/or virally-infected cells.

2. Description of Related Art

Natural killer cells (NK) cells are cytotoxic lymphocytes and play a role in an innate immune system. For example, NK cells can respond to virally infected cells and tumors. NK cells also play a role in adaptive immune response. Generally, NK cells differentiate and mature in the bone marrow, lymph node, spleen, tonsils, and thymus.

Pluripotent stem cells can differentiate into diverse specialized cell types including all derivatives of the three primary germ layers: ectoderm, endoderm, and mesoderm. Human embryonic stem cells (hESCs) are pluripotent stem cells derived from the inner cell mass of the blastocyst, an early-stage human embryo. Induced pluripotent stem cells (iPSCs) are a type of pluripotent stem cell artificially derived from a non-pluripotent cell (typically an adult somatic cell) by expression of specific genes. The process of lymphopoiesis initiating from hematopoietic cell populations isolated from mouse or human bone marrow or human umbilical cord blood (UCB) has been documented, but relatively little is known about the ability of undifferentiated hESCs or iPSCs to differentiate into the lymphoid lineage.

SUMMARY OF THE INVENTION

In a first embodiment of a method for producing NK cells from undifferentiated pluripotent stem cells comprises placing undifferentiated stem cells in a first serum-free medium, aggregating the undifferentiated stem cells in the first serum-free medium and forming embryoid bodies (EBs) by spin aggregation (resulting in formation of spin embryoid bodies (spin EBs)), culturing the spin-EBs in the first serum-free medium for inducing production of precursor cells from the spin-EBs, and culturing the precursor cells in a second serum-free medium for producing the NK cells from the precursor cells. The method uses undifferentiated stem cells that are undifferentiated human embryonic stem cells (hESCs) or undifferentiated induced pluripotent stem cells (iPSCs).

In a further embodiment there is provided a method for producing NK cells from pluripotent stem cells, the method comprising: (a) aggregating the pluripotent stem cells in a first serum-free medium, thereby forming embryoid bodies; (b) culturing the embryoid bodies in a second serum-free medium, thereby producing hematopoietic progenitor cells; and (c) culturing the hematopoietic progenitor cells in a third serum-free medium comprising interleukin 3 (IL-3), interleukin 7 (IL-7), interleukin 15 (IL-15), stem cell factor (SCF), and/or Fms-related tyrosine kinase 3 ligand (FLT3L), thereby producing natural killer cells. In some aspects, the pluripotent stem cells are human cells such as human embryonic stem cells or induced pluripotent stem cells. In certain aspects, a second serum-free medium of the embodiments comprises SCF, bone morphogenetic protein 4 (BMP4) and/or vascular endothelial growth factor (VEGF). In further aspects the method is carried out over a period of less than about 90 days, e.g., between about 10, 20, 25, or 30 days and 40, 45, 50, 60, 70 or 80 days. For example, in some aspects, the culturing of step (b) is carried out over a period of between 3 and 30 days, such as for 3-25 days, 6-20 days or 6-15 days. Likewise, in some aspects, the culturing of step (c) is carried out over a period of between 5 and 100 days, such as for 5-80 days, 10-70 days or 20-60 days.

An array of methods are available for forming embryoid bodies and may be used in accordance with the embodiments. For example, in one aspect, aggregation of embryoid bodies is performed by spin aggregation. Methods for culture of embryoid bodies and cells therefrom are also well known in the art. In some aspects, a step of culturing embryoid bodies is performed in the absence of murine stroma such as, for example, M210-B4 murine stromal cells. In some aspects, culturing of embryoid bodies is the absence of exogenous stroma or in the absence of stromal cells. As used herein exogenous stroma refers to stromal cells that added to culture, such as cells that are genetically different from the cells of the embryoid bodies (e.g., cells that are not derived from the same pluripotent stem cells as the embryoid bodies).

In some aspects, the method of the embodiments produces precursor cells that include CD34$^+$ cells that express CD34, CD34$^+$CD43$^+$ cells that co-express CD34 and CD43, and/or CD34$^+$CD45$^+$ cells that co-express CD34 and CD45. In an embodiment of the method, the step of culturing the precursor cells in the second serum-free medium is in the absence of exogenous stromal cells, such as, for example, EL08-1D2 exogenous stromal cells. In further aspects, the method does not require (and does not include) a step of cell sorting for sorting the precursor cells (e.g., based on glycoproteins expressed by the precursor cells), between the culturing EBs step and the culturing the precursor cells step. Thus, the batch of the precursor cells from the first culturing step can be directly transferred to a culturing using the second serum-free medium, without an intervening cell sorting step there between. In some aspects, the method produces NK cells, such as for example NK cells that express one or more of CD56, killer immunoglobulin-like receptors (KIRs), CD16, NKp44, NKp46, and NKG2D.

An embodiment of the method for producing NK cells from undifferentiated stem cells in some cases comprises placing undifferentiated stem cells in a first serum-free medium, aggregating the undifferentiated stem cells in the first serum-free medium and forming EBs, culturing the EBs (e.g., spin-EBs) in the first serum-free medium for inducing production of precursor cells from the EBs, culturing the precursor cells in a second serum-free medium for producing the NK cells from the precursor cells. In some aspects, a method further comprises obtaining or producing inactivated (e.g., irradiated) artificial antigen presenting cells (aAPCs). Methods for producing such aAPCs are know in the art and further detailed herein. Thus, I some aspects, NK cells are co-cultured with inactivated aAPCs. The step of co-culturing the NK cells with the aAPCs can be done in a medium that comprises, for example, interleukin 2 (IL2). In some aspects, the co-culturing is performed at a ratio of natural killer cells to inactivated aAPCs of about 5:1 to about 1:5. For example, the co-culture of NK cells and aAPCs can be at a ratio 1:1 (NK cells:aAPCs), 2:1 (NK cells:aAPCs) or 1:2 (NK cells: aAPCs).

A method for killing cancerous cells and/or virally-infected cells include the method for producing NK cells, as disclosed above, further comprising extracting the NK cells, and delivering the NK cells to a solid mass of cancerous cells. The delivering step can be injection of the NK cells into an animal or human.

In one embodiment, the present disclosure provides a method for producing natural killer cells from pluripotent stem cells comprising (a) aggregating pluripotent stem cells in a first serum-free medium, thereby forming embryoid bodies; (b) culturing the embryoid bodies in a second serum-free medium, thereby producing hematopoietic progenitor cells; and (c) culturing the hematopoietic progenitor cells in a third serum-free medium comprising interleukin 3 (IL-3), interleukin 7 (IL-7), interleukin 15 (IL-15), stem cell factor (SCF), and Fms-related tyrosine kinase 3 ligand (FLT3L), thereby producing natural killer cells.

In certain aspects, the pluripotent stem cells may be human embryonic stem cells (hESCs) or induced pluripotent stem cells (iPSCs). In certain aspects, the culturing in step (b) may be performed in the absence of murine stroma or murine stromal cells. In certain aspects, the culturing in step (c) may be performed in the absence of exogenous stroma or stromal cells. In one aspect, the method does not include a step of cell sorting between steps (b) and (c). The culturing in step (b) may be carried out for 4-40 days, preferably 6-20 days. The culturing in step (c) may be carried out for 10-100 days, preferably 20-60 days.

In some aspects, the hematopoietic progenitor cells may express CD34, co-express CD34 and CD43, or co-express CD34 and CD45. In one aspect, the natural killer cells that are produced may express one or more of CD56, killer immunoglobulin-like receptor (KIRs), CD16, NKp44, NKp46, and NKG2D.

As detailed above, in one aspect, the method may further comprise co-culturing the natural killer cells with irradiated (or otherwise inactivated) artificial antigen presenting cells (aAPCs). Said co-culturing may be performed in a medium comprising IL-2. Said co-culturing may be performed at a ratio of natural killer cells to inactivated aAPCs of about 5:1, 2:1, 1:1, 1:2, 1:3, 1:4, 1:5 or 1:10.

In a further embodiment, the present disclosure provides an immunotherapeutic method of treating a patient comprising administering an effective amount of natural killer cells produced by a method of the embodiments to a patient in need thereof. In yet further embodiment an immunotherapeutic method is provided comprising (a) producing a population of natural killer cells by a method of the embodiments; and (b) administering an effective amount of the NK cells to a patient in need thereof. For example, in some aspects, the patient is a cancer patient or a patient with an infectious disease, such as a viral infection. In some aspects, the patient is infected with human immunodeficiency virus (HIV), Epstein-Barr virus (EBV), herpes simplex virus (HSV), cytomegalovirus (CMV), varicella-zoster virus (VZV), hepatitis B virus (HBV) or hepatitis C virus (HCV). It will be understood by a skilled artisan that therapeutic methods of the embodiments may, in some aspects, involve the use of NK cells derived from autologous stem cells (e.g., cells produced from a patient blood sample or from a cord blood sample). In other aspects, the NK cells may be derived from heterologous cells.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4C shows example percentages of spin EBs expressing various molecules. Quantification of the high level of blood progenitors produced in the spin EB system. Percentages of cells expressing CD34 alone or in combination with CD45, CD43, CD31, and CD73 are shown. Each dot represents results from a separate experiment. Lines indicate mean±SEM.

FIG. 4D shows examples of derived NK cells expressing various effector molecules. CD56$^+$ NK cells derived from hESCs (with or without EL08-1D2 feeders), PB-NKs, or iPSCs (UCBiPS7). hESC- and iPSC-derived NK cells formed a CD117$^-$94$^+$ homogeneous, mature population similar to activated PB-NKs. Each also expressed various effectors molecules, including KIR, CD16, NKG2D, NKp46, and the apoptosis-inducing ligand TRAIL. Histograms representative of at least three independent experiments.

FIG. 8A shows CD34 and CD45 expression results of precursor cells. CD34$^+$CD45$^+$ progenitors derived from hESCs (H1, H9) or iPSCs (BJ1-iPS, DRiPS16, UCBiPS7) following 21 days on M210-B4 stroma.

FIG. 8B shows CD34 and CD45 expression ratio of pre-cursor cells. Differentiation efficiencies of hESCs and iPSCs, at least four separate experiments for each line.

FIG. 8C shows cytotoxicity results of derived NK cells. Cytotoxicity assay against K562 tumor cells. hESC- and iPSC-derived NK cells kill CML targets cells at a significantly higher level than UCB-derived NK cells. Means of cytotoxicity, n=3 for each except H1 (n=2), BJ1iPS-derived NK cell antitumor activity has previously been demonstrated (Ni et al., 2011).

FIG. 17 Derivation of natural killer (NK) cells from human embryonic stem cells (hESCs) expressing firefly luciferase. (A) Schematic for the derivation of hESC-derivedNKcells. GFP-luciferase$^+$ hESCs were dissociated and plated in spin EB conditions for 11 days. Cells were then transferred to conditions supporting NK cell development. (B) After 11 days in spin EB culture, cells were dissociated and stained for the progenitor markers CD34, CD45, and CD43 for FACs analysis. Spin EB-derived progenitor cells expressed high levels of CD34, CD43, and CD45. (C) Following 4 weeks in NK cell culture, cells were harvested and stained for FACs analysis. hESCs expressing GFP and luciferase differentiate into pure populations of NK cells expressing CD56, CD16, NKp46, and NKG2A. Each flow plot is representative of at least five independent experiments. EB, embryoid body.

DESCRIPTION OF ILLUSTRATIVE EMBODIMENTS

Figure 1:
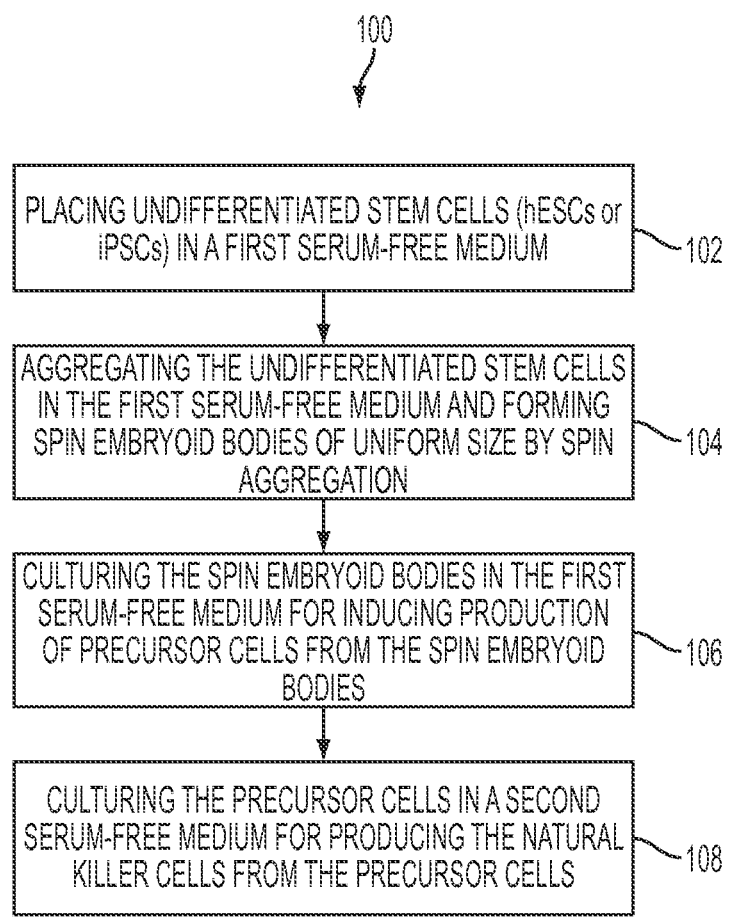
FIG. 1 shows a flow chart of an embodiment of the method for producing NK cells from undifferentiated stem cells.

Adoptive transfer of antitumor lymphocytes has gained intense interest in the field of cancer therapeutics over the past two decades. Human natural killer (NK) cells are a promising source of lymphocytes for anticancer immunotherapy. Cytokine-producing NK cells are part of the innate immune system and exhibit potent antitumor activity without need for human leukocyte antigen matching and without prior antigen exposure. Both T cell- and NK cell-based adoptive immunotherapies have been used to treat patients with refractory malignancies (Ljunggren and Malmberg, 2007; Miller et al., 2005; Rosenberg et al., 2008). A major hindrance to expanded use of these therapies is the need for cell processing and donor selection. Although T-cell development from human pluripotent stem cells (hPSCs) has been reported, it remains relatively inefficient (Galic et al., 2006; Timmermans et al., 2009).

In contrast, the use of human embryonic stem cells (hESCs) and induced pluripotent stem cells (iPSCs) to generate NK cells with antitumor and antiviral capacity is practiced (Ni et al., 2011; Woll et al., 2009; Woll et al., 2005). NK cells derived from hESCs and iPSCs possess a mature phenotype, secrete cytokines, and are cytotoxic against both hematologic and solid malignancies in vitro and in vivo (Ni et al., 2011; Woll et al., 2009; Woll et al., 2005). Therefore, the derivation of NK cells from pluripotent stem cells could provide a standardized, off-the-shelf therapeutic with a potent antitumor response to treat thousands of patients with refractory malignancies. To date, studies on hematopoietic cell development from human embryonic stem cells (hESC) and induced pluripotent stem cells (iPSCs) have used incompletely defined conditions, including the use of murine stromal cell layers, and been on a limited scale, such as the sorting of small number of hESC/iPSC-derived hematopoietic progenitor cells. Although the use of murine stromal layers does not absolutely prohibit clinical translation (if master cells banks are used), the use of culture systems that eliminate xenogeneic cells provides more defined conditions for NK cell development. Elimination of murine stromal support also provides an important developmental model to study receptor-ligand interactions driving NK cell licensing.

Herein, an efficient system for the development of functional NK cells from hESCs and iPSCs, as well as an improved method suitable for clinical translation, is described. The inventors have used a two-stage culture system to efficiently produce NK cells from hESCs and iPSCs in the absence of cell sorting and without need for xenogeneic stromal cells. This novel combination of embryoid body formation using defined conditions and artificial antigen-presenting cells (e.g., aAPCs expressing membrane-bound interleukin 21) allows production of mature and functional NK cells from several different hESC and iPSC lines. Notably, the feeder-free defined culture conditions for producing NK cells detailed herein were more efficient than previous feeder-cell based systems at generating functional NK cells (see, e.g., FIG. 4B vs. FIGS. 7-8). Although different hESC and iPSC lines had varying efficiencies in hematopoietic development, all cell lines tested could produce functional NK cells. These methods can be used to generate enough cytotoxic NK cells to treat a single patient from fewer than 250,000 input hESCs/iPSCs. Additionally, this strategy provides a genetically amenable platform to study normal NK cell development and education in vitro.

Figure 2:
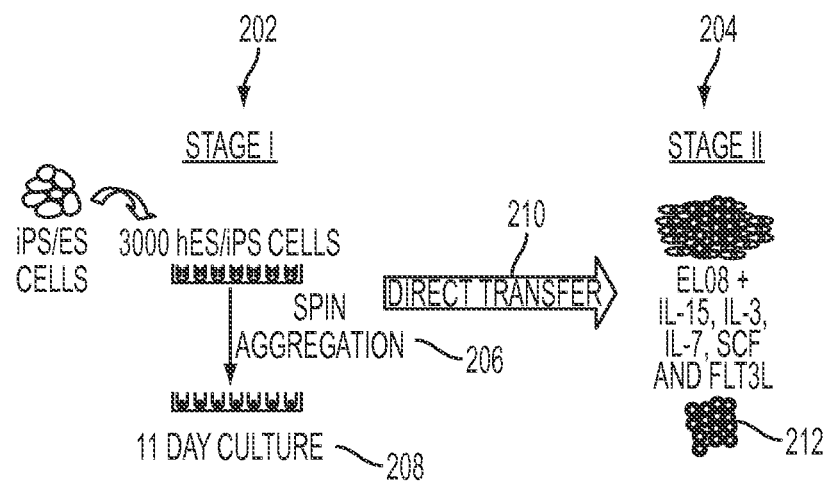
FIG. 2 shows an embodiment of the method for producing NK cells from undifferentiated stem cells. Schematic of hematopoietic and NK cell development from undifferentiated hESCs/iPSCs using the spin EB method.

The present disclosure demonstrates that a feeder-free system can be used to generate large numbers of cytotoxic NK cells for clinical translation. NK cells derived in this feeder-free system had a genotype and phenotype similar to those grown using murine stromal cells (Ni et al., 2011; Woll et al., 2009). High levels of effector molecules were expressed on the surface of NK cells from hESCs and iPSCs, including both KIR and CD16. Notable differences in the level of KIR and CD16 expression between the stromal-based and feeder-free method were likely due to developmental kinetics. When using the M210-B4 stromal-based method it is necessary to enrich the population for CD34$^+$/CD45$^+$ progenitor cells prior to NK cell differentiation as it gives rise to low frequencies (2%-10%) of these cells (FIG. 1). Although direct transfer of spin EBs allowed successful NK cell development, it may take longer for optimal CD16 and KIR acquisition because of the lower starting percentage (26.2±6.6%; FIG. 2) of progenitor cells. However, there are no intrinsic differences between NK cells derived using either method as it can be demonstrated that they express KIRs CD16 and other typical NK cell surface receptors and antigens following expansion with aAPCs. Additionally, both stromal-based and feeder-free NK cells are functionally similar as they kill tumor targets and virally-infected targets at approximately equivalent levels.

I. Definitions

"Differentiation" is a process by which a less specialized cell becomes a more specialized cell type cell to form progeny of at least one new cell type, either in culture or in vivo, than it would have under the same conditions without differentiation. Under certain conditions, the proportion of progeny with characteristics of the new cell type may be at least about 1%, 5%, 25% or more in order of increasing preference.

The term "differentiated cell" as used herein can refer to a precursor cell that has developed from an unspecialized phenotype to a specialized phenotype. For example, embryonic cells can differentiate into an epithelial cell lining of the intestine. Differentiated cells can be isolated from a fetus or a live born animal, for example.

The term "undifferentiated cell" as used herein can refer to a precursor cell that has an unspecialized phenotype and is capable of differentiating. An example of an undifferentiated cell is a stem cell.

"Pluripotent" implies that a cell is capable, through its progeny, of giving rise to all the cell types that comprise the adult animal, including the germ cells. Embryonic stem cells, induced pluripotent stem cells, and embryonic germ cells are pluripotent cells under this definition.

The term "embryonic stem cell" as used herein can refer to pluripotent cells isolated from an embryo that are maintained in in vitro cell culture. Such cells are rapidly dividing cultured cells isolated from cultured embryos that retain in culture the ability to give rise, in vivo, to all the cell types that comprise the adult animal, including the germ cells. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells may have a rounded cell morphology and may grow in rounded cell clumps on feeder layers. Embryonic stem cells are well known to a person of ordinary skill in the art.

II. Cell Culture

The term "cultured" as used herein in reference to cells can refer to one or more cells that are undergoing cell division or not undergoing cell division in an in vitro environment. An in vitro environment can be any medium known in the art that is suitable for maintaining cells in vitro, such as suitable liquid media or agar, for example.

The starting cell and the differentiated cell generally have differing requirements for culture medium and conditions. It is usual to carry out at least an initial stage of culture, after introduction of the differentiation factors, in the presence of medium and under culture conditions known to be suitable for growth of the starting cell. This is followed by a subsequent period of culture in the presence of a differentiation medium and under conditions known to be suitable for the differentiated cell. After a sufficient time for differentiation, the differentiated cells may be further cultured for expansion of the differentiated cells in an expansion medium. Such an expansion medium may comprise one or more signaling inhibitors as described above or comprise a culture medium essentially free of these inhibitors. The differentiation conditions may be essentially free of feeder cells. In further aspects, the differentiation medium may be chemically defined.

The medium according to the present embodiments can be a serum-containing or serum-free medium. The serum-free medium refers to media with no unprocessed or unpurified serum, and accordingly can include media with purified blood-derived components or animal tissue-derived components (such as growth factors). From the aspect of preventing contamination with heterogeneous animal-derived components, serum can be derived from the same animal as that of the stem cell(s).

The medium according to the present embodiments may contain or may not contain any alternatives to serum. The alternatives to serum can include materials that appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto.

Maintenance of Pluripotent Cells

Pluripotent cells may be cultured and maintained in an undifferentiated state using a variety of methods prior to a differentiation protocol on the embodiments. In certain embodiments, pluripotent cells may be cultured and maintained in an essentially undifferentiated state using defined, feeder-independent culture system, such as in a TeSR or E8 medium (see, e.g., Chen et al., *Nat. Methods,* 8(5):424-429, 2011, incorporated by reference). TeSR media, for example, are defined media which may be used to culture undifferentiated human embryonic stem cells. TeSR media includes both TeSR1 media and mTeSR media. TeSR includes bFGF, LiCl, γ-aminobutyric acid (GABA), pipecolic acid and TGFβ, and various methods utilizing TeSR have been described previously, e.g., in U.S. Application 2006/0084168 and Ludwig et al. (2006a; 2006b), which are incorporated by reference in their entirety. Alternately, undefined conditions may be used; for example, pluripotent cells may be cultured on fibroblast feeder cells or a medium which has been exposed to fibroblast feeder cells in order to maintain the stem cells in an undifferentiated state.

Feeder-independent culture systems and media may be used to culture and maintain pluripotent cells, such as hESC or iPSC. These approaches allow human embryonic stem cells to remain in an essentially undifferentiated state without the need for mouse fibroblast "feeder layers." As described herein, various modifications may be made to these methods in order to reduce costs etc. as desired.

It is expected that virtually any pluripotent or human embryonic stem cell line may be differentiated under defined conditions as described herein. For example, human embryonic stem cell line H1, H9, hES2, hES3, hES4, hES5, hES6, BG01, BG02, BG03, HSF1, HSF6, H1, H7, H9, H13B, and/or H14 etc. may be differentiated via methods described herein. Although human pluripotent cells may be preferably used in certain embodiments, in some instances it may also be possible to use other pluripotent cells, such as mammal, mouse, primate, etc. for hematopoietic differentiation.

In addition to human embryonic stem cells, iPSCs may be cultured and/or differentiated into hematopoietic precursor cells via the methods described herein. iPSCs are reprogrammed somatic cells that have stem cell-like properties (Takahashi et al., 2007; Takahashi et al., 2007; Nakagawa et al., 2007). As would be appreciated by one of skill, the term "pluripotent cells" includes both cells that naturally occur in or are derived from a blastocyst as well as cells that have been induced to de-differentiate into stem cells or return to a stem-cell-like state (see, e.g., Nakagawa et al., 2007; Yu et al., 2007).

In some aspects a matrix component may be included in a defined media for culturing and maintaining pluripotent cells in a substantially or essentially undifferentiated state. When cultured in a suitable semi-solid matrix, individual progenitors called colony-forming cells (CFCs) can proliferate to form discrete cell clusters or colonies. CFC assays may be performed by placing a cell suspension into a semi-solid medium, such as methylcellulose or collagen supplemented with nutrients and cytokines, followed by incubation, e.g., at about 37° C.

Various matrix components may be used to culture and maintain pluripotent cells, such as hESC or iPSC. For example, collagen IV, fibronectin, laminin, and vitronectin in combination may be used to provide a solid support for embryonic cell culturing and maintenance, as described in Ludwig et al. (2006), which is incorporated by reference in its entirety.

Matrigel™ may also be used to provide a substrate for cell culture and maintenance of pluripotent cells. Matrigel™ is a gelatinous protein mixture secreted by mouse tumor cells and is commercially available from BD Biosciences (New Jersey, USA). The mixture resembles the complex extracellular environment found in many tissues and is used by cell biologists as a substrate for cell culture. Methods for human embryonic stem cell culture and maintenance in defined media with Matrigel™ are described, e.g., in Ludwig et al. (2006), and may be used to culture pluripotent cells prior to hematopoietic differentiation. It is appreciated that additional methods for the culture and maintenance of human embryonic stem cells, as would be known to one of skill, may be used with the present embodiments.

III. NK Cell Differentiation

The method disclosed herein is directed to providing the appropriate conditions for developing hematopoietic cells from undifferentiated stem cells (hESCs, iPSCs). The differentiation of the stem cells is driven by formation of embryoid bodies (EBs). Analyses of transcription factor and cell surface antigen expression suggest that the method can provide the stem cells to follow developmental kinetics similar to what is observed during normal human ontogeny.

Pluripotent stem cells, such as hESCs and iPSCs, are capable of unlimited self-renewal while retaining the ability to derive myeloid, erythroid, and megakaryocytic hematopoietic cell lineages when induced or supported to differentiate under appropriate conditions.

The hESC-derived NK (hESC-NK) cells are also highly efficient at direct cell-mediated cytotoxicity and antibody dependent cell-mediated cytotoxicity, as well as cytokine production (e.g., IFN-γ). Like hESC-NK cells, the iPSC-derived NK (iPSC-NK) cells also acquire similar ability to kill cancer cells. The hESC-NK cells and iPSC-NK cells express activating and inhibitory receptors similar to NK cells isolated from adult peripheral blood.

The hESCs and iPSCs can differentiate to NK cells using a 2-stage in vitro differentiation scheme. The 2-stage differentiation scheme includes (Stage 1) generation of hematopoietic progenitor cells from stem cells using spin EBs, and (Stage 2) NK cell differentiation from spin EBs obtained from Stage 1. An example of the 2-stage in vitro differentiation scheme is provided in detail below. A skilled artisan will recognize, however, that a variety of methods may be used for generating hematopoietic progenitor cells from pluripotent cells. For example, U.S. Pat. No. 8,372,642, which is incorporated herein by reference, details a highly efficient culture system to generate hematopoietic progenitor cells.

Stage 1. Example generation of hematopoietic progenitor cells from hESCs or iPSCs by spin EB.
1. TrypLE-adapted undifferentiated hESCs/iPSCs are maintained on low-density MEF feeders or in the absence of feeder cells. One or two days before setting up spin EB differentiation, pass TrypLE-adapted hESCs/iPSCs onto fresh MEFs (or into a feeder-free system) at 1:1 ratio that will allow them to be 80%-90% confluent on the day of differentiation setup.
2. To prepare for spin EB plating, pipet 150 μl sterile water into the 36 outer wells of each 96-well plate to minimize loss of well volume to evaporation.
3. Aspirate culture media from hESCs/iPSCs and add 1.0 ml pre-warmed TrypLE Select to each well. Place plates in incubator (37° C.) until ES/iPSCs start to come off the plate. This typically takes ~5 min if TrypLE is pre-warmed; preferably, do not leave the plates in the incubator longer than 5 min.
4. Collect dissociated cells in a conical tube and pipet up and down to break up clumps. Dilute TrypLE with 1 volume Bovine Serum Albumin (BSA) Polyvinylalcohol Essential Lipids BPEL media and at least 1 volume DPBS. Spin cells down at 1500 rpm, 5 min, 8° C. Remove supernatant and resuspend the cells in 5 ml BPEL media plus 5 ml DPBS. Spin cells down again.
5. Remove supernatant and resuspend cells in 5-10 ml BPEL media. Pass cells through 70 μm filter into a fresh 50 ml conical in order to remove clumps. Count filtered cells and aliquot cells to be used for plating into a 50 ml conical. Spin cells down and resuspend them with stage I spin EB differentiation medium to $3 \times 10^4$ cells/ml.
6. Transfer 100 μl cell aliquots into each of the inner 60 wells of the prepared 96-well plates with 150 μl of water in outer wells. Spin 96-well plates at 480 g, 8° C. for 4 min. Incubate the plates at 37° C., 5% $CO_2$ for 8-11 days until hematopoietic progenitor $CD34^+CD45^+$ cells are generated. Do not disturb the plates during the first three days of differentiation while the EBs are forming (Note 5). Under certain conditions, the percentage of $CD34^+$ cells can be approximately 40%-60% and the percentage of $CD34^+CD45^+$ cells can be up to 20%-40%. By day 11, good differentiation should have more hematopoietic cells surrounding the initial EBs. Most cells remaining in the EB will be endothelial/mesenchymal progenitor populations.

As discussed above other methods for feeder-free cell generation of endothelial progenitor cells may be used in accordance with the instant embodiments. For example, certain methods for differentiating pluripotent cells into hematopoietic precursor cells or endothelial cells comprise: a) obtaining a plurality of substantially undifferentiated pluripotent cells in a defined media comprising at least one growth factor (i.e., growth factors appropriate to maintain pluripotency); b), optionally, incubating the cells in a defined media which is free or essentially free of BMP4, VEGF, IL-3, Flt3 ligand, and GMCSF; c) culturing the cells in a further defined media comprising an amount of BMP4 and VEGF sufficient to promote differentiation in a plurality of the cells; and d) culturing the cells in a defined media comprising an amount of either (1) IL-3 and Flt3 ligand, or (2) VEGF, FGF-2 or an FGF-2 mimic, and IGF sufficient to expand and promote differentiation in a plurality of the cells (see, e.g., U.S. Pat. No. 8,372, 642).

Stage 2. Example, NK cell generation.
1. Half-medium changes are performed every 5-6 days. During the first week, the NK cell differentiation medium contains 10 ng/ml IL-3, which is removed with the first medium change. Phenotyping of NK cell development can be performed by flow cytometry.
2. Mature $CD45^+CD56^+$ NK cells are obtained. The cells can be phenotyped by flow cytometry. In vitro function of hES/iPS cell-derived NK cells can be analyzed by measurement of direct cytolytic activity tumor cells (such as K562) by a standard $^{51}$Cr-release assay or immunological assays for cytotoxic granule or cytokine release.

IV. Additional Methods for Producing Hematopoietic Progenitor Cells

As indicated above, a range of methods may be employed to generate a population of hematopoietic progenitor cells for further NK cell production. In certain preferred aspects, hematopoietic progenitor cells generated using defined culture conditions and with the use of feeder cells. For example, after partially, essentially, or completely dissociating or individualizing pluripotent cells, the cells may be further cultured in a defined media to promote hematopoietic differentiation. It has been specific combinations of growth factors can substantially promote differentiation of the pluripotent cells into hematopoietic precursors and hematopoietic cell lineages. Sequential application of specific combinations of growth factors may be used to further promote differentiation of pluripotent cells. In certain embodiments, specific combinations of growth factors are critical for the hematopoietic differentiation of pluripotent cells. For example, combinations of BMP4, VEGF, Flt3 ligand, IL-3, and GMCSF may be used to promote hematopoietic differentiation. In certain aspects, sequential exposure of cell cultures to a first media that includes BMP4 and VEGF (and optionally FGF-2), followed by culture in a second media that includes Flt3 ligand, IL-3, and GMCSF can increase the differentiation of pluripotent cells into hematopoietic precursor cells and hematopoietic cells. In some aspects FGF-2 (e.g., 50 ng/ml) can be included in a media containing BMP4 and VEGF resulted in at least a doubling of the efficiency of the generation of hematopoietic precursor cells from pluripotent cells.

While differentiation of pluripotent cells into hematopoietic precursor cells may be performed using defined or undefined conditions, it will be appreciated that defined conditions are generally preferable in embodiments where the resulting cells are intended to be administered to a human subject. Hematopoietic stem cells may be cultured from pluripotent stem cells under defined conditions (e.g., using a TeSR media and a matrix component such as Matrigel™ or in an E8 media), and hematopoietic cells may be generated from embryoid bodies derived from the from pluripotent cells. In other embodiments, pluripotent cells may be co-cultured on OP9 cells or mouse embryonic fibroblast cells and subsequently differentiated.

Pluripotent cells may be allowed to form embryoid bodies as a part of the differentiation process. The formation of "embryoid bodies" (EBs), or clusters of growing cells, in order to induce differentiation generally involves in vitro aggregation of pluripotent stem cells into EBs and allows for the spontaneous and random differentiation of pluripotent stem cells into multiple tissue types that represent endoderm, ectoderm, and mesoderm origins. Three-dimensional EBs can thus be used to produce some fraction of hematopoietic cells and endothelial cells.

EBs may be formed as detailed supra. In some aspects, undifferentiated hESC or iPSC adapted to feeder free growth on Matrigel™ coated plates may be harvested at confluence using collagenase IV (1 mg/ml) treatment for about 10 minutes at about 37° C. The wells may be washed free of collagenase after the incubation and the EBs may be formed by scraping the wells in EB basal media. The media may be changed the next day to EB differentiation media containing different cytokine formulations.

To promote EB formation, the cells may be transferred to a low-attachment plates for an overnight incubation in "EB basal media" containing IMDM supplemented with about 20% BIT9500 (Stem Cell Technologies) or Serum Replacement 3, about 1% NEAA, about 1 mM L-glutamine, and about 0.1 mM mercaptoethanol, about 0.75% BSA, and about 50 ug/ml ascorbic acid. The next day the cells may be collected from each well and centrifuged. The cells may then be resuspended in "EB differentiation media," which comprises EB basal media supplemented with additional growth factors. For example, in some aspects, an EB differentiation media is used that is supplemented with about 10-100 ng/ml bone morphogenetic factor (BMP-4), e.g., about 50 ng/ml BMP-4, about 10-100 ng/ml vascular endothelial growth factor (VEGF) e.g., about 50 ng/ml VEGF, about 25-75 ng/ml stem cell factor (SCF), about 25-75 ng/ml Flt-3 ligand (Flt-3L), about 10-100 ng/ml interleukin-3 (IL-3), about 10-100 ng/ml interleukin-6 (IL-6), optionally, about 20-40 ng/ml granulocyte colony-stimulating factor (G-CSF), optionally, about 20-40 ng/ml granulocyte macrophage colony-stimulating factor (GM-CSF), optionally, about 0.2 U/ml erythropoietin (EPO), optionally, about 25 ng/ml thrombopoieitin (TPO), and, optionally, about 25-75 ng/ml FGF-2. The media may be changed every four days by transferring the EB's into a 15-mL tube and letting the aggregates settle for about 5 minutes. In certain embodiments, the EB differentiation media may include about BMP4 (e.g., about 10-100 ng/ml), VEGF (e.g., about 10-100 ng/ml), and optionally FGF-2 (e.g., about 25-75 ng/ml or about 50 ng/ml). In some aspects, an initial EB differentiation media is used that is supplemented with BMP-4, VEGF and optionally, FGF2, followed by culture in a second EB differentiation media supplemented with SCF, Flt-3 ligand, TPO, IL-6 and/or IL-3 as indicated above.

The supernatant may be aspirated and replaced with fresh differentiation medium. Alternately the cells may be half fed every two days with fresh media. The cells may be harvested at different time points during the differentiation process.

For example, a defined medium may be used to induce hematopoietic CD34+ differentiation. As detailed above, the defined medium may contain the growth factors BMP-4, VEGF, Flt3 ligand, IL-3 and/or GMCSF. Pluripotent cells may be cultured in a first defined media comprising BMP4, VEGF, and optionally FGF-2, followed by culture in a second media comprising either (Flt3 ligand, IL-3, and GMCSF) or (Flt3 ligand, IL-3, IL-6, and TPO). The first and second media may also comprise one or more of SCF, IL-6, G-CSF, EPO, FGF-2, and/or TPO. Substantially hypoxic conditions (e.g., less that 20% $O_2$) may further promote hematopoietic or endothelial differentiation.

Cells may be substantially individualized via mechanical or enzymatic means (e.g., using a trypsin or TrypLE™). A rho kinase inhibitor (ROCK inhibitor; e.g., H1152 or Y-27632) may also be included in the media. It is anticipated that these approaches may be automated using, e.g., robotic automation.

Although the use of defined methods for the differentiation of pluripotent cells into hematopoietic precursor cells may be preferred in certain instances, undefined approaches may nonetheless be used in various embodiments. One undefined method for the differentiation of hematopoietic stem cells from human ESCs involves culturing the ESCs on feeder cells, such as a mouse embryonic fibroblast (MEF) feeder layer or the mouse stromal cell line OP9, which induces robust differentiation to CD34$^+$. Briefly, ESCs may be grown on MEFs in the presence of growth factors, and the MEFs provide a substrate and likely some nourishment for the cells. In contrast to defined conditions, use of OP9 cells generally does not require extra growth factors to induce CD34+ differentiation. The mechanisms by which these processes occur are not fully understood. This approach may also be used in combination with certain growth factors and serum (Wang, 2007). MEFs are also often used for culturing and maintaining human ESCs. Methods that utilize culture on mouse embryonic fibroblasts, such as the below protocol, may be modified to include Knockout™ serum replacement instead of FBS.

The following undefined protocol may be used for differentiation of pluripotent cells into hematopoietic cells. H1 cells may be routinely maintained on MEFs, and then passed onto almost confluent OP9 stromal cells in αMEM+20% defined FBS+100 ng/ml TPO at $1 \times 10^5$ cells/well (1 well is 9.6 cm2). Cells may be fed with fresh medium at days 2 and 4. On day 7, cells may be split 1:3 onto fresh OP9 cells using collagenase IV. Cells may be fed with fresh medium at days 8 and 10. On day 11, cells may be split 1:1 onto fresh OP9 cells using collagenase IV, followed by Trypsin/EDTA to get single cells, and the medium may be changed to αMEM+10% defined FBS+100 ng/ml TPO. Cells may be fed by adding an additional 1 ml of this medium daily from days 14-16. In certain embodiments, methods for differentiation involving OP9 cells may be performed as described in Gaur et al., 2006, which is specifically incorporated by reference in its entirety.

V. Defined Culture Media and Components

As described herein, one or more defined culture medium may be advantageously used to promote the differentiation of pluripotent cells into hematopoietic precursor cells and/or NK cells; in particular, the elimination of animal products such as serum and mouse feeder layers can reduce the risks associated with exposure of cells to animal products and allow for the generation of cells that could be more safely administered to a human subject. As traditional stem cell culture development has relied on serum products and mouse feeder layers for differentiating stem cells into a variety of cell types, these traditional procedures have limited the scale on which differentiation can be conducted, increased biological variability and potential contamination, and severely hampered the use of ES cells in translational therapies in which they might otherwise prove useful. Various media components that may be employed according to the embodiments are detailed below.

A. Growth Factors

Various growth factors may be used to promote the differentiation of pluripotent cells into hematopoietic precursor cells. In certain embodiments, a defined culture medium of the present embodiments may contain one, two, or more growth factors such as, for example, (BMP-4 and VEGF) or (BMP-4, VEGF, FLT-3, IL-3, and GMCSF).

Growth factors which may be comprised in a defined culture medium of the present embodiments include, but are not limited to, BMP-4, VEGF, bFGF, stem cell factor (SCF), Flt3 ligand, IL-3, IL-6, IL-7, IL-9, IL-11, IL-15, insulin related growth factor 1 (IGF1), insulin related growth factor 2 (IGF2), erythropoietin (EPO), thrombopoietin (TPO), granulocyte-macrophage-colony-stimulating factor (GMCSF or GM-CSF), and granulocyte colony-stimulating factor (GCSF or G-CSF). A defined culture medium of the present embodiments may contain one, two, three, or more of these factors; for example, other growth factors may be included in a defined medium in order to increase proliferation or modulate the differentiation state of the cells. In certain embodiments, a defined media may contain at least (BMP-4 and VEGF, and optionally FGF-2) or (FLT-3, IL-3, and GMCSF); in these embodiments, while not necessary, one or more additional growth factor may be included in the defined media. For example, GMCSF can be substituted using TPO or SCF at about 25 ng/ml in the second step of the differentiation process. Various amounts of these factors may be used to stimulate cellular responses (e.g., in the amounts described in Yamamura et al., 2008; Fadilah et al., 2007; Bashey et al., 2007). For example, about 1-50 ng/mL, about 5-25 ng/mL, or about 10 ng/mL of TPO may be included to promote cell expansion or differentiation of cells. In various embodiments, SCF may be included in a defined media at a concentration of from about 5-100 ng/mL, about 10-50 ng/mL, or about 25 ng/mL. In various embodiments, IL-6 may be included in a defined media at a concentration of from about 5-50 ng/mL, about 5-25 ng/mL, or about 10 ng/mL. Granulocyte colony stimulating factor (G-CSF) may be used for generating granulocytes from hematopoietic precursor cells.

1. BMP-4

Bone morphogenetic protein-4 (BMP-4) is a member of the group of bone morphogenic proteins and a ventral mesoderm inducer. BMPs are expressed in adult human bone marrow (BM) and are important for bone remodeling and growth. In certain embodiments, inclusion of BMP4 is only needed for the first two to three days in culture, after which time it can be removed from the system with no detrimental effect on differentiation.

BMP-4 is important for the modulation of the proliferative and differentiative potential of hematopoietic progenitor cells (Bhardwaj et al., 2001; Bhatia et al., 1999; Chadwick et al., 2003). Additionally, BMP-4 can modulate early hematopoietic cell development in human fetal, neonatal, and adult hematopoietic progenitor cells (Davidson and Zon, 2000; Huber et al., 1998; Marshall et al., 2000). For example, BMP-4 can regulate the proliferation and differentiation of highly purified primitive human hematopoietic cells from adult and neonatal sources (Bhatia et al., 1999), and BMP-4 can promote hematopoietic differentiation in human embryonic stem cells (Chadwick et al., 2003).

BMP-4 may be included in a defined culture medium at a concentration of about 5-100 ng/mL, about 20-100 ng/mL, about 20-50 ng/mL, about 10-30 ng/mL, about 15-30 ng/mL, about 20-30 ng/mL, or any range derivable therein. In certain embodiments, BMP-4 is included in the defined culture media at a concentration of about 5, 10, 15, 20, 25, 30, 35, 40, 45, or about 50 ng/mL.

2. VEGF

Vascular endothelial growth factor (VEGF) is an important signaling protein which is involved in formation of the embryonic circulatory system and angiogenesis. VEGF can affect a variety of cell types including vascular endothelium and other cell types (e.g., neurons, cancer cells, kidney epithelial cells). In vitro, VEGF can stimulate endothelial cell mitogenesis and cell migration. VEGF function has also been shown to be important in a variety of disease states including cancer, diabetes, autoimmune diseases, and ocular vascular diseases.

VEGF may be included in a defined culture medium at a concentration of from about 10-100 ng/mL, about 20-100 ng/mL, about 10-50 ng/mL, about 15-30 ng/mL, about 20-30 ng/mL, about 20-50 ng/mL, or any range derivable therein. In certain embodiments, VEGF is included in the defined culture media at a concentration of about 2.5, 5, 10, 15, 20, 25, 30, 35, 40, 45, or about 50 ng/mL.

3. FGF-2

Basic fibroblast growth factor, also referred to as bFGF or FGF-2, is a growth factor which has been implicated in diverse biological processes, including limb and nervous system development, wound healing, and tumor growth. Previous studies have indicated that bFGF is unlikely to affect hematopoietic cell development or survival (Ratajczak et al., 1996.), although bFGF has been used to support feeder-independent growth of human embryonic stem cells (Ludwig et al., 2006). In certain embodiments, bFGF is not required to induce differentiation; thus, in various embodiments it may be included or excluded in a medium of the present embodiments.

bFGF may be included in a defined culture medium at a concentration of from about 5 to about 100 ng/mL, 5 to about 50 ng/mL, from about 5 to about 25 ng/mL, from about 25 to about 50 ng/mL, or any range derivable therein. In certain embodiments, bFGF is included in the defined culture media at a concentration of about 2.5, 5, 10, 15, 20, 25, 30, 35, 40, 45, 50, 55, 60, 65, 70, or about 75 ng/mL. These concentrations may be particularly useful for media used for the maintenance of pluripotent cells in an undifferentiated or substantially undifferentiated state. In various embodiments, FG2 (e.g., at about 100 ng/ml) may be used for maintenance of pluripotency of cells. To promote hematopoietic differentiation, cells may be exposed to FGF2 at a concentration between about 5-50 ng/ml.

In various embodiments, lower concentrations of bFGF may be included in a defined media in a "preconditioning" culture phase prior to hematopoietic differentiation. For example, from about 5 ng/mL to about 50 ng/mL, from about 10 ng/mL to about 30 ng/mL, from about 15 ng/mL to about 25 ng/mL, less than about 50 ng/mL, less than about 40 ng/mL, less than about 30 ng/mL, or about 10, 15, 20, 25, or 30 ng/mL bFGF may be included in a defined media in a preconditioning culture of pluripotent cells prior to differentiation of the cells into hematopoietic precursor cells. In certain embodiments, a TeSR media without growth factors which has been supplemented with bFGF (e.g., about 25-75 ng/mL or about 50 ng/ml) or FGF-2 and 0.1 ng/mL TGF-β may be used in a preconditioning culture of pluripotent cells prior to hematopoietic differentiation. In certain embodiments, this preconditioning step can be essential to promote subsequent hematopoietic differentiation.

After pluripotent cells have been preconditioned (e.g., in a TeSR media without growth factors supplemented with TGF-β and FGF-2 for about 1 day), cells may then be placed in an EB differentiation media comprising BMP4, VEGF, and FGF-2 (e.g., at about 25-50 ng/ml). As shown in the below examples, the inclusion of FGF-2 can result in at least a doubling in the efficiency for differentiation of pluripotent cells, such as hESC or iPSC, into hematopoietic precursor cells.

It is envisioned that, in certain embodiments, other fibroblast growth factors such as acidic FGF (aFGF), FGF4, FGF9, FGF17 or FGF18 may substituted for or included with bFGF, e.g., at the concentrations described above. Alternately, an FGF-2 mimicking compounds may be substituted for FGF-2 to produce substantially or essentially the same effect. FGF-2 mimics include FGF-2 mimicking peptides, antibodies, and small molecules. For example, synthetic peptide F2A4-K-NS mimics the effects of FGF-2 in vitro and in vivo (Lin et al., 2006) and may be substituted for FGF-2 in various embodiments of the present embodiments.

FG loop (FGL) peptide is another example of a FGF-2 mimetic which may be used in certain embodiments of the present embodiments. FGL is a 15 amino acid sequence in the second F3 module of NCAM that represents a part of the binding site of NCAM to the FGFR1. FGL has been shown to bind to and activate FGFR1 and to stimulate neurite outgrowth (Kiselyov et al., 2003).

The BioSET F2A peptide may also be substituted for FGF-2. The BioSET F2A peptide is a synthetic mimetic of the natural human FGF-2 growth factor. The BioSET F2A peptide and the F2A4-KNS peptide are available from FYI Tornier, Inc., or BioSurface Engineering Technologies, Inc. ("BioSET"). It is envisioned that combinations of FGF-2 mimicking compounds may also be substituted for FGF-2 in various embodiments of the present embodiments.

4. IL-3

Interleukin-3 (IL-3) is a hematopoietic growth factor involved in the survival, proliferation and differentiation of multipotent hematopoietic cells. In five mammalian species, including man, the gene encoding IL-3 has been isolated and expressed to yield the mature recombinant proteins. The human IL-3 gene encodes a protein of 133 amino acids with two conserved cysteine residues and 2 potential N-linked glycosylation sites (Wagemaker et al., 1990).

In certain embodiments, IL-3 is included in a culture medium of the present embodiments at a concentration of from 2.5 to about 50 ng/mL, 2.5 to about 50 ng/mL, from about 5 to about 50 ng/mL, from about 5 to about 25 ng/mL, from about 5 to about 15 ng/mL, or any range derivable therein. In certain embodiments, IL-3 is included in the defined culture media at a concentration of about 2.5, 5, 10, 15, 20, 25, or about 30 ng/mL. As shown in the below examples, Flt3 ligand and IL-3 can exert a synergistic action on differentiation of pluripotent cells into hematopoietic precursor cells. In certain embodiments, inclusion of IL-3 is included in the media for the first approximately 1-3 weeks in the culture of pluripotent cells, or from about day 5 to about day 7 of culture in a medium to promote differentiation of pluripotent cells, after which time it can be removed from the system with little or essentially no detrimental effect on differentiation.

5. FLT3 Ligand

Flt3 ligand, also referred to as FLT-3 ligand, is the endogenous ligand for FLT3. FLT3 is a receptor tyrosine kinase expressed by immature hematopoietic progenitor cells. The ligand for FLT3 is a transmembrane or soluble protein and is expressed by a variety of cells including hematopoietic and marrow stromal cells; in combination with other growth factors, Flt3 ligand can stimulate the proliferation and development of stem cells, myeloid and lymphoid progenitor cells, dendritic cells and natural killer cells. Activation of the receptor leads to tyrosine phosphorylation of various key adaptor proteins known to be involved in different signal transduction pathways that control proliferation, survival and other processes in hematopoietic cells. FLT3 and mutations affecting FLT3 are also important in pathological diseases, such as the prognosis and therapy of leukemia (Drexler et al., 2004).

In certain embodiments, Flt3 ligand is included in a culture medium of the present embodiments at a concentration of from 5 to about 100 ng/mL, 5 to about 50 ng/mL, from about 10 to about 30 ng/mL, from about 15 to about 30 ng/mL, from about 20 to about 30 ng/mL, or any range derivable therein. In certain embodiments, Flt3 ligand is included in the defined culture media at a concentration of about 2.5, 5, 10, 15, 20, 25, 30, 35, 40, 45, or about 50 ng/mL. In certain embodiments, Flt3 ligand is included in the media for the first approximately 1-3 weeks in the culture of pluripotent cells, or from about day 5 to about day 7 of culture in a medium to promote differentiation of pluripotent cells, after which time it can be removed from the system with little or essentially no detrimental effect on differentiation.

6. Granulocyte-Macrophage Colony-Stimulating Factor

Granulocyte-macrophage colony-stimulating factor, also abbreviated as GM-CSF or GMCSF, is a protein secreted by macrophages, T cells, mast cells, endothelial cells and fibroblasts. GMCSF is a cytokine that can function as a white blood cell growth factor, and GMCSF can stimulate stem cells to produce granulocytes (neutrophils, eosinophils, and basophils) and monocytes. Monocytes can exit the circulation and mature into macrophages. Thus, GMCSF can play a role in the immune/inflammatory cascade, by which activation of a small number of macrophages can rapidly lead to an increase in their numbers, a process crucial for fighting infection. The active form of GMCSF is typically found in vivo extracellularly as a homodimer. GMCSF is also referred to as molgramostim or sargramostim (Leukine) when expressed in yeast cells. In certain embodiments, recombinantly produced growth factors may be used to promote hematopoietic differentiation of pluripotent cells.

In certain embodiments, GMCSF is included in a culture medium of the present embodiments at a concentration of from about 2.5 to about 100 ng/mL, 2.5 to about 50 ng/mL, from about 5 to about 50 ng/mL, from about 5 to about 25 ng/mL, from about 5 to about 15 ng/mL, or any range derivable therein. In certain embodiments, GMCSF is included in the defined culture media at a concentration of about 2.5, 5, 10, 15, 20, 25, or about 30 ng/ml. In certain embodiments, inclusion of GMCSF ligand is included in the media for the first approximately 1-3 weeks in the culture of pluripotent cells, or from about day 5 to about day 7 of culture in a medium to promote differentiation of pluripotent cells, after which time it can be removed from the system with little or essentially no detrimental effect on differentiation.

7. Stem Cell Factor

Stem cell factor (SCF) is a cytokine which binds CD117 (c-Kit). SCF is also known as "KIT ligand," "c-kit ligand," or "steel factor." SCF exists in two forms: cell surface bound SCF and soluble (or free) SCF. Soluble SCF is typically produced in vivo by the cleavage of surface bound SCF by metalloproteases. SCF can be important for the survival, proliferation, and differentiation of hematopoietic stem cells and other hematopoietic progenitor cells. In vivo, SCF can change the BFU-E (burst-forming unit-erythroid) cells, which are the earliest erythrocyte precursors in the erythrocytic series, into the CFU-E (colony-forming unit-erythroid).

In certain embodiments, SCF is included in a culture medium of the present embodiments at a concentration of from about 5 to about 100 ng/mL, 5 to about 50 ng/mL, from about 10 to about 30 ng/mL, from about 15 to about 30 ng/mL, from about 20 to about 30 ng/mL, or any range derivable therein. In certain embodiments, SCF is included in the defined culture media at a concentration of about 2.5, 5, 10, 15, 20, 25, 30, 35, 40, 45, or about 50 ng/mL.

8. IL-6

Interleukin-6 (IL-6) is a pro-inflammatory cytokine. In vivo, IL-6 is secreted by T-cells and macrophages and stimulates immune responses to trauma or other tissue damage leading to inflammation. IL-6 can also play a role in responses to certain bacterium, and osteoblasts secrete IL-6 in vivo to stimulate osteoclast formation. In humans, smooth muscle cells in the tunica media of many blood vessels can produce IL-6 as a pro-inflammatory cytokine, and IL-6 is an important in vivo mediator of fever.

In certain embodiments, IL-6 is included in a culture medium of the present embodiments at a concentration of from about 2.5 to about 100 ng/mL, 2.5 to about 50 ng/mL, from about 5 to about 50 ng/mL, from about 5 to about 25 ng/mL, from about 5 to about 15 ng/mL, or any range derivable therein. In certain embodiments, IL-6 is included in the defined culture media at a concentration of about 2.5, 5, 10, 15, 20, 25, or about 30 ng/mL.

9. TPO

Thrombopoietin, or TPO, is a glycoprotein hormone which is primarily produced in vivo by the liver and kidney and is involved in the in vivo generation of platelets in the bone marrow. In certain embodiments, TPO is included in a culture medium of the present embodiments at a concentration of from about 2.5 to about 100 ng/mL, 5 to about 75 ng/mL, from about 10 to about 50 ng/mL, from about 15 to about 35 ng/mL, at about 25 ng/ml, or any range derivable therein. In certain embodiments, TPO is included in the defined culture media at a concentration of about 2.5, 5, 10, 15, 20, 25, 30, 35, 40, 45 or about 50 ng/mL.

B. ROCK Inhibitors and PKC Inhibitors

In still further aspects of the invention additional media components may be included in ES cell growth media such as molecules that reduce ES cell apoptosis or promote survival after the disassociation of cells (e.g., during splitting of cell populations or prior to the formation of EBs). A defined culture medium may be used to seed, culture, maintain, or differentiate ES cells and may contain an inhibitor of Rho-independent kinase and/or an inhibitor of protein kinase C(PKC). In certain embodiments, a ROCK inhibitor and/or a PKC inhibitor may be used to enhance the survival and differentiation efficiency of pluripotent cells after individualization. In certain embodiments, a ROCK inhibitor and/or a PKC inhibitor may be included in a seeding medium comprising TeSR or mTeSR media and a matrix component.

In certain embodiments, a defined culture media may comprise one or more Rho-associated kinase inhibitor such as Y-27632 or a derivative thereof. Furthermore, in some aspects, a defined media may comprise HA-100.

The HA-100 or Y-27632 may be present in an ES cell growth media, e.g., at a concentration of about 1-15 μM, 5-15 μM, 1-30 μM, 5-30 μM, or about 5, 6, 7, 8, 9, 10, 11, 12, 13, 14, 15, 16, 17, 18, 19, 20, 21, 22, 23, 24, 25, 26, 27, 28, 29, or 30 μM, or any range derivable therein. In certain embodiments, HA-100 or Y-27632 is present in an ES cell growth media at about 10-20 μM.

Other ROCK inhibitors which may be included in an ES cell growth media according to the present embodiments include H-1152 ((S)-(+)-2-Methyl-1-[(4-methyl-5-isoquinolinyl)sulfonyl]homopiperazine). H-1152 exhibits an approximately ten-fold greater potency than HA-100. Thus, H-1152 may be present in an ES cell growth media, e.g., at a concentration of about 0.1-1004, about 0.5-5 μM, about 1-3 μM, or about 0.5, 0.6, 0.7, 0.8, 0.9, 1, 2, 3, 4, or 5 μM, or any range derivable therein. In certain embodiments HA-100 is present in an ES cell growth media at about 1 μM. H-1152, which allows for very efficient seeding of individualized human ES cells in 96-well plates (similar to HA-100 but at 10-fold lower concentration). Individualized HES cells that are otherwise passaged in cell clumps allow more uniform cell densities per well, which is a stringent prerequisite for cell-based small molecule screening. H-1152 can thus be used in protocols for ES cell-based small molecule screening which involve automated cell culture according to the present embodiments. H-1152 has been previously described in, e.g., Ikenoya et al. 2002 and Sasaki et al. 2002, which are incorporated herein by reference.

Other ROCK inhibitors which may be included in an ES cell growth media include Y-27632, N-(4-Pyridyl)-N'-(2,4,6-trichlorophenyl)urea, 3-(4-Pyridyl)-1H-indole, glycyl-H1152 ((S)-(+)-2-Methyl-4-glycyl-1-(4-methylisoquinolinyl-5-sulfonyl)homopiperazine) and/or HA1100 (Hydroxyfausdil). Y-27632 ((R)-(+)-trans-4-(1-Aminoethyl)-N-(4-Pyridyl)cyclohexanecarboxamide) is commercially available from Sigma-Aldrich and has been described previously (see, e.g., Maekawa et al., 1999; Davies et al., 2000).

Exemplary ROCK inhibitors which may be used to promote cell survival include, but are not limited to, HA100, H1152, (+)-trans-4-(1-aminoethyl)-1-(pyridin-4-ylaminocarbonyl)cyclohexane dihydro-chloride monohydrate (e.g., WO00078351, WO00057913), imidazopyridine derivatives (e.g., U.S. Pat. No. 7,348,339), substituted pyrimidine and pyridine derivatives (e.g., U.S. Pat. No. 6,943,172) and substituted isoquinoline-sulfonyl compounds (e.g., EP00187371).

It is anticipated that a PKC inhibitor may be used in combination with or as a substitute for a ROCK inhibitor. For example a PKC inhibitor may be used to promote cell survival, e.g., after dissociation or individualization of pluripotent cells prior to differentiation into hematopoietic precursor cells. PKC inhibitors which may be used include, for example, a V5 peptide (e.g., U.S. Pat. No. 7,459,424), polymyxin B, calphostin C, palmitoyl-DL-carnitine, stearoylcarnitine, hexadecylphosphocholine, staurosporine and its derivatives, sangivamycin; safingol, D-erythro-sphingosine; chelerythrine chloride, melittin; dequalinium chloride; ellagic acid, HBDDE, 1-O-hexadecyl-2-O-methyl-rac-glycerol, Hypercin, K-252, NGIC-J, Phloretin, piceatannol, tamoxifen citrate, substituted piperazines and thiazines (e.g., U.S. Pat. No. 6,815,450).

C. Other Components

A defined culture medium may also contain additional components such as nutrients, amino acids, antibiotics, buffering agents, and the like. In certain embodiments a defined culture medium of the present embodiments may contain non-essential amino acids, L-glutamine, Pen-strep, and monothioglycerol.

BIT 9500 (StemCell Technologies Inc., Vancouver, Canada) may also be included in a defined culture medium of the present embodiments, e.g., in an amount of about from about 10% to about 30%, or in an amount of about 20%. BIT 9500 contains pre-tested batches of bovine serum albumin, insulin and transferrin (BIT) in Iscove's MDM. BIT 9500 contains 50 mg/mL bovine serum albumin (buffered with NaHCO3), 50 µg/mL rh insulin, 1 mg/mL human transferrin (iron-saturated). In certain embodiments, KOSR may be substituted for BIT 9500 in embodiments where a defined medium is not required. KOSR is an undefined medium which is commercially available (e.g., from Gibco/Invitrogen, catalog #10828) and has been described previously in WO98/30679.

The use of BIT, as described above, may be replaced by HIT; HIT includes the compositions described about in BIT, with the exception that the components, such as serum albumin, are human components (e.g., human serum albumin). For example, the use of HIT may be preferable in embodiments where the risk of a possible infection etc. is of particular concern.

Serum Replacement 3 (Sigma-Aldrich, St. Louis, Mo.) may also be substituted for BIT 9500. Serum Replacement 3 contains only human proteins (i.e., human serum albumin, human transferrin, human recombinant insulin). Serum Replacement 3 does not contain growth factors, steroid hormones, glucocorticoids, cell adhesion factors, detectable Ig or mitogens. As shown in the below examples, inclusion of Serum Replacement 3 can, in certain embodiments, further promote differentiation.

In various embodiments, a defined culture medium may contain one or more vitamin, mineral, salt, lipid, amino acid, or other component. For example, a defined medium of the present embodiments may contain one or more component present in TeSR medium, e.g., at the same or a comparable concentration as is included in TeSR.

VI. Separation of Cells

After preparation of hematopoietic (e.g., CD34+, CD43+) precursor cells from embryonic stem cells or iPSCs, it may be desirable to substantially purify or separate one or more sub-population of further or substantially differentiated cells (e.g., hematopoietic precursor cells, endothelial cells, etc.) from the cell population. Methods for separation of cells using flow cytometry, such as FACS, or magnetic activated cell sorting may be used to separate hematopoietic cells from a heterogeneous cell population. Exemplary cell separation protocols are also shown in the examples below.

A. Magnetic Activated Cell Sorting (MACS)

Cells may be isolated from differentiated hESCs using a magnetic activated cell sorter (MACS). MACS typically utilizes an antibody, such as a anti-CD34 antibody, in combination with magnetic beads to separate cells over a column. MACS may, in certain embodiments, be more gentle on cells and favorably affect cell viability and integrity as compared to FACS, possibly due to the laser illumination of cells involved with FACS.

Various MACS products are commercially available, including MACS MicroBeads™ columns or AutoMACS™ (Miltenyi Biotec, CA, USA), which may be used according to the manufacturer's instructions. PBS/0.5% BSA (without EDTA) may used as the buffer for cell isolation. In some experiments, a Dead Cell Removal Kit (Miltenyi Biotec) may be used to remove dead cells prior to isolation of CD34+ cells. Repeated MACS columns may be used if necessary.

B. FACS

Fluorescence activated cell sorting (FACS) may also be used to separate CD34+ cells. FACS utilizes the degree or fluorescence exhibited by a cell, e.g., due to bound an anti-CD34 antibodies comprising a fluorescent tag, to separate cells. In this way FACS may be used to separate hematopoietic CD34+ cells from a heterogeneous cell population.

For example, the following protocol may be used to perform FACS to quantify hematopoietic cells. Cells may be prepared in PBS containing 1% FBS or 0.5% BSA, and labeled for 15-30 minutes at 4° C. with a combination of monoclonal antibodies (mAbs), such as CD31-PE (clone WM-59), CD34-APC (clone 581, 8G12), CD45-FITC (clone HI30) (all from BD PharMingen), and KDR-PE (clone 89106) (R&D system). A 1:50 dilution for specific antibodies, and 1:200 dilution for IgG control may be used. The samples may be analyzed by a FACSCalibur™ (Becton-Dickson, New Jersey, U.S.A.) or another similar device.

VII. Bioreactors and Robotic Automation

One or more steps for the culture of stem cells and/or differentiation of NK cells from pluripotent cells may be automated. Automating a process using robotic or other automation can allow for more efficient and economical methods for the production, culture, and differentiation of cells. For example, robotic automation may be utilized in conjunction with one or more of the culture of human embryonic stem cells, passaging, addition of media, addition of differentiation media, culture in differentiation media, and separation of cell type, e.g., using magnetic separation or FACS.

A bioreactor may also be used in conjunction with the present embodiments to culture, maintain, and/or differentiate cells (e.g., human embryonic stem cells, CD34+ cells, hematopoietic cells, etc.) according to the present embodiments. Bioreactors provide the advantage of allowing for the "scaling up" of a process in order to produce an increased amount of cells. Various bioreactors may be used with the present embodiments, including batch bioreactors, fed batch bioreactors, continuous bioreactors (e.g., a continuous stirred-tank reactor model), and/or a chemostat.

For example, spinner flasks may be used to scale up methods for the maintenance and/or differentiation of pluripotent cells to allow for the generation of increased numbers of cells. In certain embodiments, the following protocol may be used to promote EB formation in spinner flasks: Undifferentiated hESC's and iPSC's may be adapted to feeder free growth on Matrigel coated plates and harvested at confluence, e.g., using TrypLE treatment for about 5 minutes at about 37° C. The cells may be harvested in EB basal media containing IMDM supplemented with about 20% BIT9500 (Stem Cell Technologies) or Serum Replacement-3 (Sigma Aldrich), about 1% NEAA, about 1 mM L-glutamine, and about 0.1 mM mercaptoethanol, about 0.75% BSA, about 50 ug/ml ascorbic acid and about 1 μM ROCK inhibitor (e.g., H-1152). The cells may then be placed in spinner flasks (e.g., 125 ml Corning) at a density of about 0.5-2 million cells per ml. The spinners may be set to 30-40 rpm overnight to facilitate EB formation. Alternately the cells could be placed under static conditions for 24 hours in low attachment plates. It is generally recognized that the cell density and/or speed of spinner flask movement may be varied depending on the particular spinner flask or bioreactor used. After about 12-24 hrs of culture the cells may be placed in an EB differentiation media containing cytokines without the ROCK inhibitor on a magnetic stir platform in a spinner flask, e.g., rotating at a speed of about 60 RPM. The side caps of the spinner flasks may be loosened to allow gas transfer. The cells may be placed in EB basal media supplemented with BMP-4, about VEGF, and FGF-2. On about the fourth day of differentiation the cells may be fed by allowing the spinner flask to remain still so that the suspended EB aggregates can settle to the bottom of the flask for 15-20 minutes. The spent media may then be aspirated (e.g., with allowing about 20 mL to remain in a 125 ml spinner). The cells may then be gently swirled and fresh media containing BMP-4, VEGF, and FGF-2 may be added to the cells. The spinner flasks may be set to a speed of about 40-60 rpm throughout the entire process of hematopoietic differentiation, although it is anticipated that substantially higher or lower speeds of rotation may be utilized. On about day 5-6 of differentiation the spent media was aspirated as described above and the cells may be placed in EB basal media supplemented with further growth factors. Spent media may be aspirated on about day 8 and 10 as described above. The EB cultures may be harvested on about day 12 of differentiation. Cells may be stained for the phenotypic expression of surface markers (e.g., CD34+ or CD45+) to quantify the hematopoietic progenitor content of the population.

Robotic automation specifically envisioned for use with the present embodiments may be obtained from, for example, Tecan (CA, USA). Robotics may include liquid handling tools such as cap-piercing probes and disposable tips to minimize carry-over between samples. In various embodiments, robotics may be utilized in conjunction with one or more bioreactor for culturing cells (e.g., during the maintenance or growth of hESCs, the differentiation of hESCs into hematopoietic cells, or the differentiation of hematopoietic cells into subsequent lineages such as erythrocytes, etc.). As shown in the below examples, conditions for the maintenance and generation of hematopoietic precursor cells may be at least partially or completely automated using the Tecan Cellerity™ system (an industrially relevant robotic platform). The Tecan Cellerity™ is equipped with Tecan liquid handling robot (Freedom EVO 200), an automated incubator (Storex500) with a capacity for 500 Roboflasks™, a media storage refrigerator, a Cedex cell counter, spinner flasks for expansion and seeding of suspension cells' and a ROMA robotic arm to handle plates and an 8-channel fixed tip pipette. Part, essentially all, or all of EB differentiation protocol may be automated. For example, on day 12 of differentiation the cells may be harvested by the Tecan Cellerity system and washed manually for cell surface staining of markers. Post staining, the cells may be analyzed using the Hypercyt connected to the Accuri flow cytometer. This process may be used for high-throughout screening of hematopoietic precursor populations. In certain embodiments, undifferentiated hESCs or iPSCs may be cultured on the robot, e.g., using Matrigel™ coated roboflasks (Corning) via the method described above. The maintenance, seeding, feeding and/or harvesting of the EBs may be partially or completely automated, e.g., using the Tecan Cellerity™ system. This robot has the capacity to include spinner flasks or a bioreactor may be used to generate large numbers of cells.

In certain embodiments, it may be useful to miniaturize or "scale down" methods of the present embodiments. These approaches may be particularly useful, e.g., where the methods comprise a high-throughput screen of compounds, e.g., which may promote de-differentiation or differentiation of cells towards a particular lineage. High-throughput screens may also be used to evaluate one or more property of a candidate substance (e.g., toxicity, ability to promote or reduce differentiation, etc.). Miniaturization of the methods may involve the use of low-attachment plates (e.g., 96 well plates) and/or culture of cells under low oxygen (e.g., less than about 25% $O_2$ or about 5% $O_2$) conditions. In certain embodiments, the following methods may be used: Undifferentiated hESC's or iPSC's adapted to feeder free growth on Matrigel coated plates may be preconditioned for 24 hours using TeSR without growth factors supplemented with about 0.1 ng/ml TGF and about 20 ng/ml zebrafish FGF. The cells may be harvested at confluence, e.g., using TrypLE treatment for about 5 minutes at about 37° C. The cells may be collected in EB basal media containing IMDM supplemented with about 20% BIT9500 or Serum Replacement-3, about 1% NEAA, about 1 mM L-glutamine, and about 0.1 mM mercaptoethanol, about 0.75% BSA, about 50 μg/ml ascorbic acid and about 1 μM ROCK inhibitor (e.g., H-1152). To initiate EB formation, the cells may be placed in low attachment 96 well plates at a density of about 0.1 million cells per well in EB basal containing a ROCK inhibitor. It is anticipated that the exact concentration of cells used may be varied to achieve a similar effect. EB formation may also be facilitated by incubating the plated at low $O_2$ conditions. After about 12-24 hrs the cells may be placed in EB differentiation media containing about 50 ng/ml bone morphogenetic factor (BMP-4), about 50 ng/ml vascular endothelial growth factor (VEGF), and about 25 ng/ml zebrafish FGF-2. About 300 μl of media was may be used per well in, e.g., a 96 well plate. On about day 3-4 of differentiation, the cells may be half fed by gently removing half the volume of spent media (e.g., between 100-150 μl) and adding equal volume of fresh media. On about day 5-6 of differentiation, the spent media may be aspirated as described above and the cells may be placed in EB basal media, e.g., supplemented with either: (1) about 25 ng/ml of Flt-3 ligand, about 10 mg/ml of IL-3 and about 10 ng/ml GMCSF, or (2) media containing about 25 ng/ml of Flt-3 ligand, about 25 ng/ml of SCF, about 25 ng/ml of TPO, about 10 ng/ml IL-3, and about 10 ng/ml IL-6. The differentiating EB cultures may be half fed with fresh media on about day 8 and 10 of differentiation as described above. EB cultures may be harvested on about day 12 of differentiation. These approaches can be successfully used to generate a variety of cell lineages (e.g., erythroid, megakaryocyte, macrophage, dendritic cells, mast cells, granulocyte), and similar results may be obtained using iPSCs or hESC.

Methods of the present embodiments may be utilized in a single cell assay, using robotic automation, by including the ROCK inhibitors HA100 and/or H1152 in the media to induce cells to adhere single cells to a plate. On the robot, the addition of the small molecules HA100 or H1152 or Y-27632 to the culture system can greatly improve the viability of pluripotent cells, including ES, hESC, and iPSCs. In certain embodiments, survival of pluripotent cells in a TeSR media can be improved by the inclusion of a ROCK inhibitor or a PKC inhibitor, particularly after the cells are proteolytically or mechanically separated into clumps or individualized. The ROCK inhibitors can promote individualized hES cells to attach to a surface and grow. Some or all of the process of maintenance or proliferation of pluripotent cells, as well as differentiation into hematopoietic precursor cells or a specific hematopoietic lineage may be automated. Part of all of the automated methods may utilize defined conditions.

VIII. Artificial Antigen Presenting Cells (AAPCS) and Use Thereof

Some aspects of the embodiments concern aAPCs and the use thereof in the preparation of NK cell compositions. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009), each of which is incorporated herein by reference.

In certain aspects, aAPCs used to expand NK cells express little or no MHC/HLA class I (e.g., as is the case for K562 cells). Examples of aAPC systems specifically adapted for NK cell expansion can be found, for example, in Denman et al., 2012; Campana et al. 2009 and the review of Cho et al., 2009, each of which is incorporated herein by reference.

In other preferred embodiments, the aAPCs, may be inactivated (for example, chemical treatment or irradiation), so that essentially no cell growth or replication occurs after the inactivation. Thus inactivation maintains the important APC functions of aAPCs while helping to alleviate concerns about safety of a cell therapy product developed using the aAPCs. For methods related to inactivation and aAPCs, see for example, U.S. Patent Application Publication No. 20090017000, which is incorporated herein by reference.

Subsequently, an inactivated aAPC culture may be maintained for as long a time as is appropriate to activate and enrich for a therapeutically effective population of NK cells. In some aspects, aAPCs are added to an NK culture periodically as the NK cells are expanded (e.g., every three days, five days or every week). Thus, in some aspects, NK cell expansion comprises 2, 3, 4, 5, 10 or more co-culture cycles aAPCs.

IX. Uses of Cytotoxic NK Cells

With the improved efficiency and defined components of this system, clinical translation of hESC/iPSC-derived cells becomes feasible. Current adoptive NK cell-based immunotherapy uses an NK cell containing clinical product (typically comprising approximately 50% NK cells) consisting of about $2 \times 10^7$ cells per kilogram (Miller et al., 2005). Our methods without the aAPCs would provide this number of NK cells from about $13 \times 10^6$ undifferentiated hESCs or iPSCs (approximately one six-well plate). Using the aAPCs would mean that fewer than $10^6$ undifferentiated hESCs/iPSCs would be required per patient at current NK cell doses.

This process can be used to produce substantially more NK cells starting from a single, homogenous and well-characterized starting cell population than can be done with individual apheresis donors used for peripheral blood NK (PB-NK) cells. Additionally, these methods decrease the amount of cell processing compared with that of peripheral blood, which requires depletion with anti-CD3 antibodies against T cells to prevent graft-versus-host disease and anti-CD20 antibodies against B cells to prevent passenger lymphocyte syndrome. Neither T cells nor B cells are present in the cultures of the present method (Kaufman, 2009). Using the expanding knowledge of KIRs and allo-reactivity, NK cells from diverse genetic backgrounds could be generated to create the optimal NK cell "superdonor", a concept recently established in a large cohort of subjects indicating that particular KIR haplotypes (centromeric BB) are optimal in clearing residual leukemia in patients undergoing allogeneic hematopoietic stem cell transplantation (Cooley et al., 2010). Improved treatment of patients with other tumors may also be feasible with these hESC- and iPSC-derived cells that have cytolyic activity against ovarian, pancreatic, breast cancer, prostate cancer, and myeloma cells (Woll et al., 2009) (FIG. 4). Treatment of HIV or other chronic viral infections may also be possible (Ni et al., 2011). Additionally, it may be possible to engineer hESCs and iPSCs with antitumor and antiviral chimeric antigen receptors to provide an off-the-shelf product of targeted lymphocytes for immunotherapies (Porter et al., 2011; Torikai et al., 2012; Knorr and Kaufman, 2010; Sadelain et al., 2009).

Clinical translation of hESC- and iPSC-derived cells continues to be steadily advancing. Indeed, investigators have shown the delivery of retinal pigment epithelial cells derived from hESCs are safe, and may be effective, in patients with a form of macular degeneration (Schwartz et al., 2012). Clinical use of hESC/iPSC-derived hematopoietic cells has been of keen interest for over a decade (Kaufman, 2009). Strictly considering cell number, the ability to create enough hESC-derived NK cells for therapy is more feasible than the number of cells needed to generate one unit of red blood cells (RBCs) ($10^{12}$ RBCs per unit). Studies on more efficient derivation of human iPSCs using nonintegrating methods more suitable for clinical translation are also advancing (Robinton and Daley, 2012). Therefore, the ability to produce large numbers of cytotoxic NK cells means the prospect of hESC- and iPSC-derived hematopoietic products for diverse clinical therapies can be realized in the not too-distant future.

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods of the Embodiments

FIG. 1 shows a flowchart 100 for an embodiment of the method for producing natural killer cells from undifferentiated stem cells. The method 100 uses undifferentiated stem cells, such as undifferentiated hESCs or iPSCs. The method comprises placing 102 undifferentiated stem cells in a first serum-free medium, aggregating 104 the undifferentiated stem cells in the first serum-free medium and forming spin-EBs by spin aggregation, culturing 106 the spin-EBs in the first serum-free medium for inducing production of precursor cells from the spin-EBs, and culturing 108 the precursor cells in a second serum-free medium for producing the natural killer cells from the precursor cells.

FIG. 2 shows a diagram that tracks with the flowchart 100 for the method, wherein the diagram separates the flowchart 100 into 2-stages: 202 and 204. In Stage I 202, hematopoietic progenitor cells are generated from hESCs or iPSCs by spin EB 206 and then the culturing process 208. After the direct transfer 210 of the cells from Stage 1 to Stage 2, in Stage 2 204, NK cells are generated 212.

Figure 3:
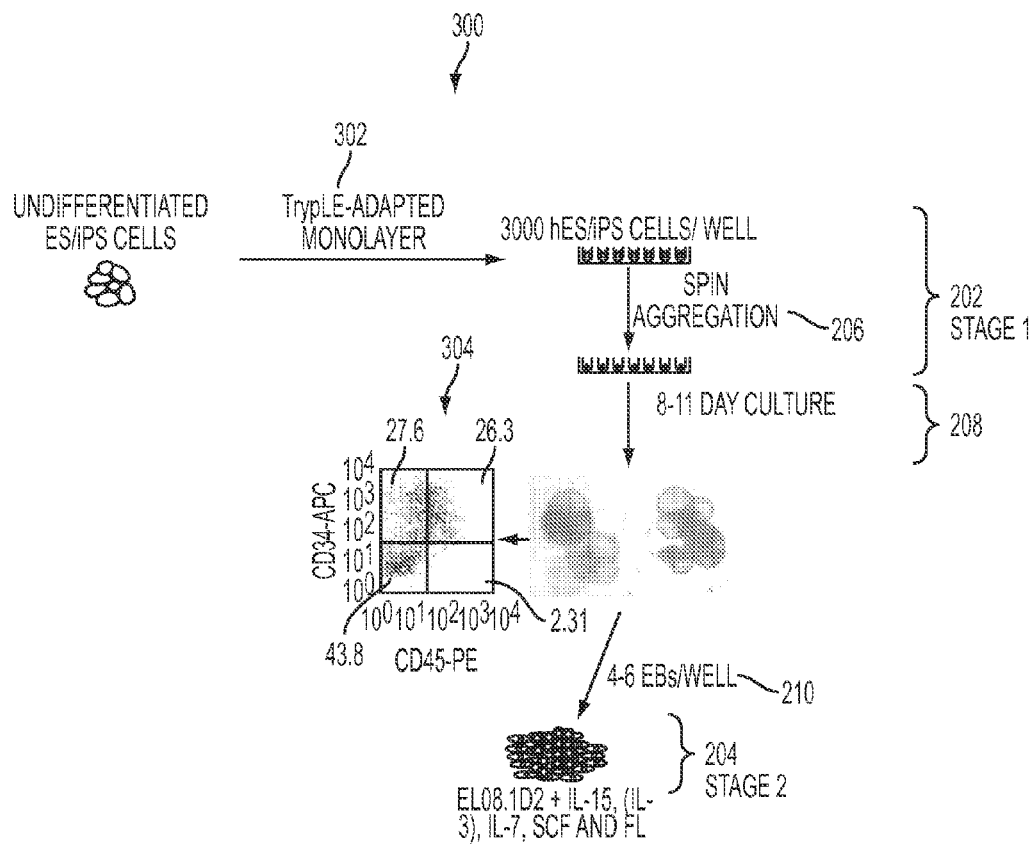
FIG. 3 shows an embodiment of the method for producing NK cells from undifferentiated human pluripotent stem cells.

FIG. 3 shows an embodiment of the method 300 wherein the undifferentiated stem cells (hESCs or iPSCs) are prepared 302 prior to promoting the differentiation of the cells, in order to generate undifferentiated stem cells that are more amenable to aggregation. The stem cells can be prepared 302 by passing the stem cells in TrypLE Select (Invitrogen) on low-density mouse embryoid fibroblasts (MEFs at, for example, 90,000 cells/well) for a minimum of 10 passages. For iPSCs, the UCBiP7 line derived from UCB CD34$^+$ hematopoietic progenitors can be used. Generating TypLE adapted hESCs or iPSCs, cultures around 60%-70% confluency can be dissociated and filtered through a 70 micron sterile filter. It is preferable to use only pure cultures of hESCs lacking any signs of differentiation. The cells can be passaged 1:1 on low density MEFs in regular hESC media until cellular proliferation allow passing at more dilute ratios, preferably occurring around the 10$^{th}$ passage. To set up TrypLE passaged hESCs into spin EBs, adapted cells around 70% confluency are dissociated with TrypLE and filtered through a 70 μm filter to remove any clumps. Except for the preparing step 302, the rest of the steps shown in FIG. 3 are substantially same as the steps shown in FIG. 2. Accordingly, corresponding steps are identified using the same reference characters. FIG. 3 shows the analysis 304 of the cell differentiation after day 11, performed by flow cytometry showing that the precursor cells express CD34 and CD45.

The method includes placing 102 undifferentiated stem cells in a first serum-free medium. The first serum-free medium includes natural killer cell promoting growth factors that include but are not limited to cytokines, interleukins, chemokines, growth factors, colony-stimulating factors, cell-bound proteins, or any combinations thereof. The first serum-free medium can include SCF complex, bone morphogenetic protein 4 (BMP4), and vascular endothelial growth factor (VEGF). For example, the stem cells can be placed 102 in a first serum-free medium at a concentration of 3000 cells per well (100 μl volume) of a round-bottom 96-well plate in BPEL media containing stem cell factor (SCF, 40 ng/ml), vascular endothelial growth factor (VEGF, 20 ng/ml), and bone morphogenic protein 4 (BMP4, 20 ng/ml). BPEL media can be made in 200 mL volumes and contain Iscove's Modified Dulbecco's Medium (IMDM, 86 mL, Invitrogen), F12 Nutrient Mixture with Glutamx I (86 mL, Invitrogen), 10% deionized Bovine Serum Albumin (BSA, 5 mL, Sigma), 5% Polyvinyl alcohol (10 mL, Sigma), Linoleic acid (20 uL of 1 mg/mL solution, Sigma), Linolenic acid (20 uL of 1 mg/mL solution, Sigma), Synthecol 500× solution (Sigma), α-monothioglyceral (Sigma), Protein-free hybridoma mix II (Invitrogen), ascorbic acid (5 mg/mL, Sigma), Glutamax I (Invitrogen), Insulin-transferrin-selenium 100× solution (Invitrogen), Penicillin/streptomycin (Invitrogen). The outer wells of the plate are then filled with sterile water to prevent evaporation of the media.

The method includes aggregating the undifferentiated stem cells in the first serum-free medium 104 and forming spin-EBs by spin aggregation. Spin aggregation uses a spin embryoid body (spin EB) protocol for blood cell differentiation without the use of murine stroma. It has been discovered that the spin EB process for driving the differentiation without the use of murine stroma achieves similar results, and it is more efficient than the process that uses murine stroma. The cells are aggregated 104 for aggregating the undifferentiated stem cells in the first serum-free medium and forming spin EBs. For example, the plates containing the cells and the media are spin aggregated at 1,500 RPMs for 5 minutes at room temperature and placed in a 37° C. incubator with 5% $CO_2$.

The method further includes culturing the spin-EBs in the first serum-free medium 106 for inducing production of precursor cells from the spin-EBs. An embodiment of the method includes the step of culturing the embryoid bodies 106 being performed in the absence M210-B4 murine stroma. Another embodiment of the method includes the step of culturing the embryoid bodies 106 being performed in the absence any murine stroma. During the culturing step 106, it is preferable that the cells are not removed from the first serum-free medium for at least 3 days to ensure formation of spin EBs in the plates. Spin EB differentiation is promoted under these conditions for 8-11 days, or 9-12 days, or preferably 11 days.

Figure 4A:
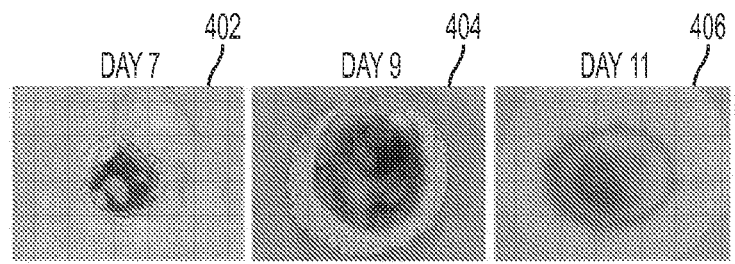
FIG. 4A shows example results of cell differentiation during a culturing step for generating hematopoietic progenitor cells. Aggregated hESCs or iPSCs form discrete spin EBs in each individual well and proliferate over a period of 11 days. Pictures were taken at 4× magnification at days 7, 9, and 11. At day 11 there are a large number of hematopoietic-appearing cells surrounding the EBs.
Figure 4B:
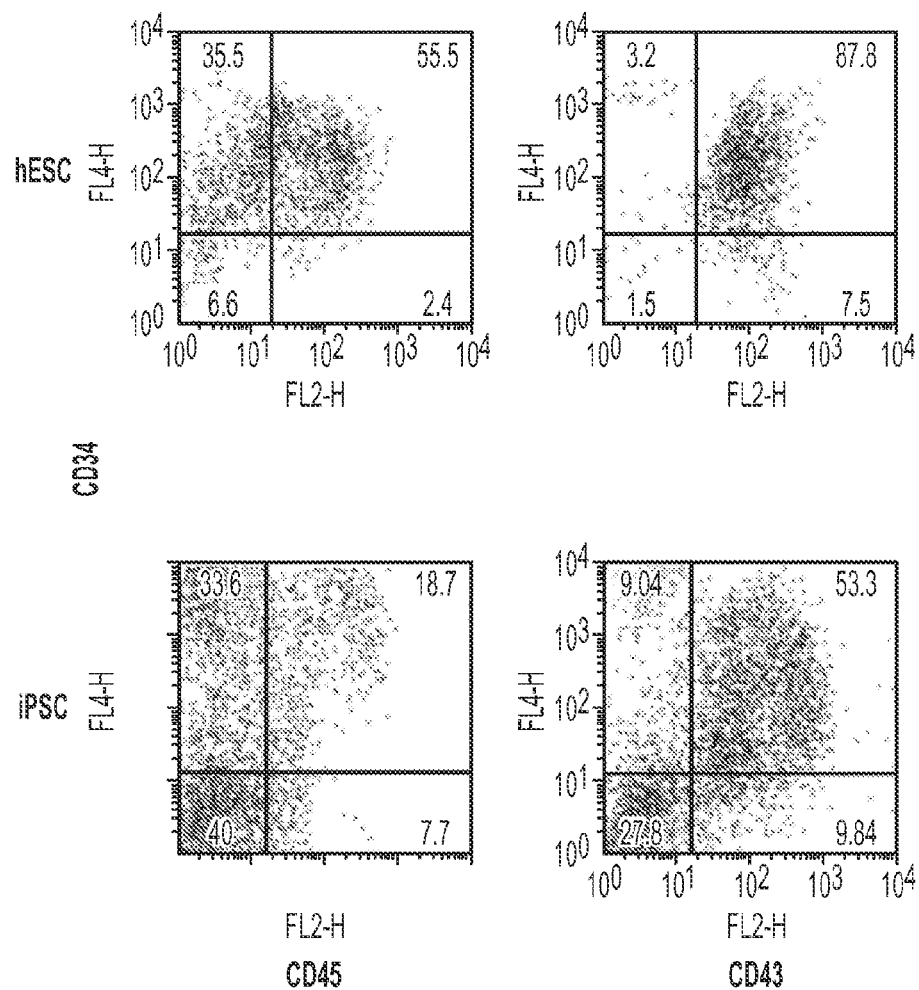
FIG. 4B shows cytometry analysis of cell differentiation for hESC and iPSC derived cells. Spin EBs generated higher frequencies of hematopoietic progenitors cells from hESCs and iPSCs than coculture on murine stromal cells (as in FIGS. 7-8). At day 11 of spin EB culture, individual EBs were collected, dissociated, and stained with antibodies against CD34, CD43, and CD45.

FIG. 4A shows the results of cell differentiation after day 7 402, after day 9 404, and after day 11 406. The method produces precursor cells that include CD34$^+$ cells that express CD34, CD34$^+$CD43$^+$ cells that co-express CD34 and CD43, and/or CD34$^+$CD45$^+$ cells that co-express CD34 and CD45. FIG. 4B shows analysis of the cell differentiation performed by flow cytometry. The flow cytometry can be performed using the following antibodies: CD34-APC, CD45-PE, CD31-PE, CD31-APC, CD-73PE, CD43-PE, NKp46-PE, NKp44-PE, CD56-APC, CD16-PercpCy5.5, CD117-PercpCy5.5, all of which may be obtained from Becton Dickson. CD158a/h-PE, CD158j-PE, CD158i-PE, CD158e1/e2, CD159a-PE and -APC, which may be obtained from Beckman Coulter. CD107aPercpCy5.5 and INF-γ PacBlue which may be obtained from eBioscince. Flow cytometry can be done on a BD FACS Calibur or LSRII and data analyzed using FlowJo (Treestar). FIG. 4B shows, for example, hESC-derived hematopoietic cells expressing CD34 (55.9±6.4%) with many coexpressing CD43 (41.8±9.51%) or CD45 (26.2±6.6%). FIG. 4B also shows iPSC-derived hematopoietic cells expressing CD34 (12.06±5.40%) and CD45 (3.20±1.43%). FIG. 4C shows an example of the spin EBs expressing CD34 alone and percentages of CD34 co-expression with CD45, CD43, CD31, and CD73.

After 8-11 days, or 9-12 days, or preferably 11 days, of culturing 106 the cells to promote spin-EB differentiation, the well plates can be directly transferred to another well to start culturing 108 in a second serum-free medium for producing the natural killer cells from the precursor cells. The method eliminates the need for cell sorting for sorting the precursor cells based on glycoproteins expressed by the precursor cells, between the culturing the spin-EBs step and the culturing the precursor cells step. As shown in FIG. 4D, the derived NK cells can also expresses various effectors molecules, including KIR, CD16, NKG2D, NKp46, and the apoptosis inducing ligand TRAIL.

The second serum-free medium includes NK cell initiating growth factors that include but are not limited to cytokines, interleukins, chemokines, growth factors, colony-stimulating factors, cell-bound proteins, or any combinations thereof. For example, the second serum-free medium can include SCF complex, VEGF, interleukin 3 (IL3), interleukin 6 (IL6), thrombopoietin (TPO), and erythropoietin (EPO). For example, the second serum-free medium can include IL3, interleukin 7 (IL7), interleukin 15 (IL15), SCF complex, and Fms-related tyrosine kinase 3 ligand (FLT3L). In an embodiment of the method for producing natural killer cells from undifferentiated stem cells, the step of culturing the precursor cells in the second serum-free medium is in the absence of exogenous stromal cells. In an embodiment of the method for producing natural killer cells from undifferentiated stem cells, the step of culturing the precursor cells in the second serum-free medium is in the absence of EL08-1D2 exogenous stromal cells. For example, 6 wells of the 96 well plate of the spin-EB differentiation from the above example can be directly transferred to one well of a 24-well plate in NK cell initiating growth factors that include but are not limited to cytokines, interleukins, chemokines, growth factors, colony-stimulating factors, cell-bound proteins, or any combinations thereof. The 24-well plates can contain 100,000 irradiated (3000 Rads) EL08-1D2 cells per well. Six wells of spin EBs can be directly transferred to uncoated 24-well plates. The method produces natural killer cells that express CD56, killer immunoglobulin-like receptors (KIRs), CD16, NKp44, NKp46, and NKG2D.

The culturing step 108 may take about 4 weeks. Within the first two weeks following the direct transfer (start of the culturing step 108), there is proliferation of nonadherent hematopoietic cells from the spin EBs at a similar level to what is seen with EL08-1D2 stroma. Additionally, the culturing step 108 causes the cells to produce their own adherent cells in culture. In other words, the spin EB cells produce their own spin EB stromal cell layers in the culture in the absence of exogenous stromal cells. The spin EB stromal cell layers express high levels of CD31 and CD73 in addition to MHC class I molecules (HLA-ABC and HLA-E), which are important for NK cell development and acquisition of killer immunoglobulin-like receptors 10. Additionally, the spin EB stromal cells also support the development of NK cells from UCB CD34$^+$ cells. Using these defined conditions, the cultures contain NK cells similar to conditions utilizing the EL08-1D2 stromal cells. These cells express a mature NK cell phenotype and are just as cytotoxic as their stromal-derived counterparts. These cells are also capable of secreting the cytokine IFN-γ. These data demonstrate successful in vitro derivation of functional, cytotoxic lymphocytes in the absence of any sorting or murine stromal cell support. With the absence of xenogeneic feeder layers, this provides a genetically amenable system to study human NK cell education as well as a single, defined human source for adoptive immunotherapy.

Figure 5:
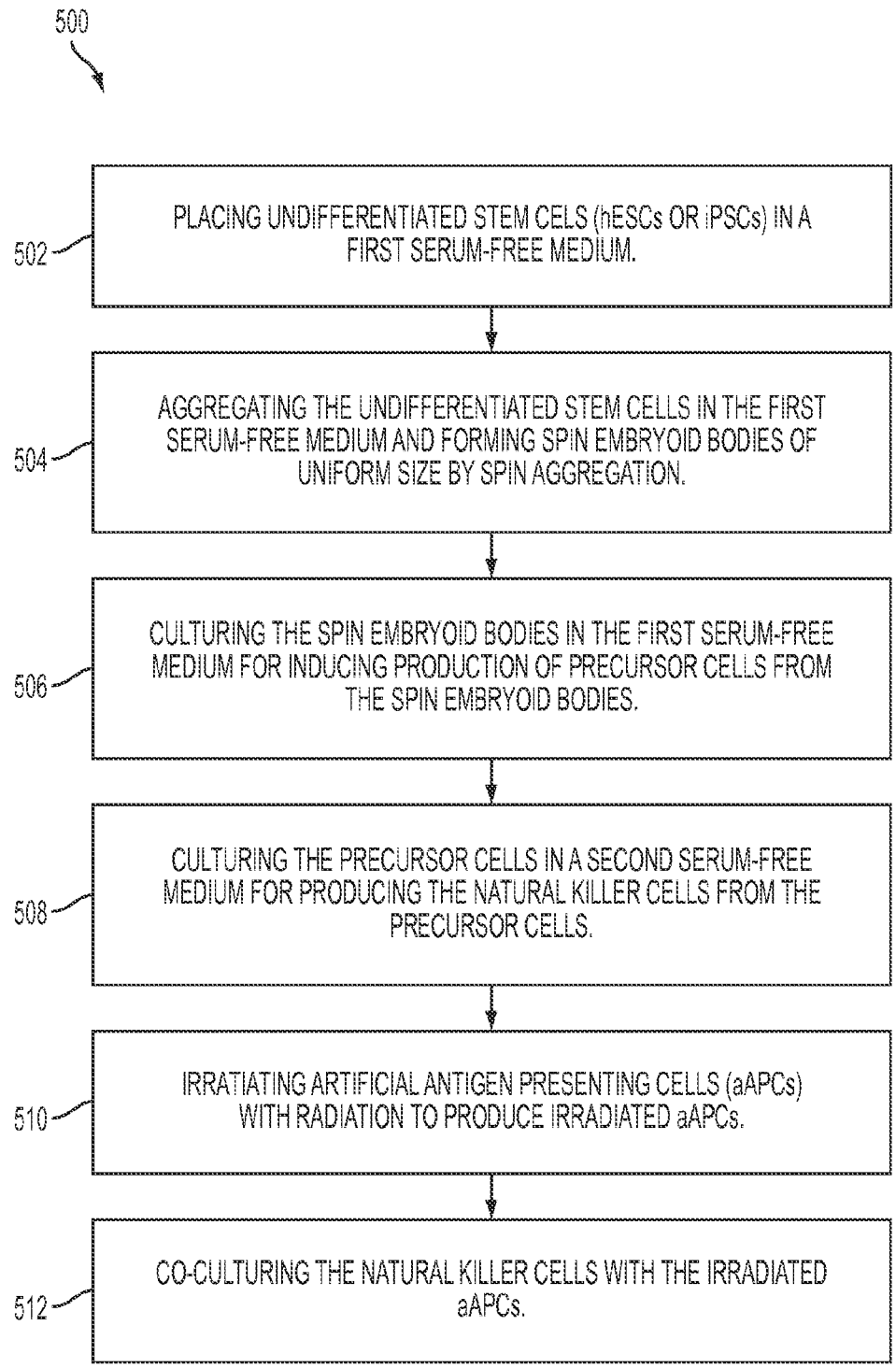
FIG. 5 shows a flowchart for an embodiment of the method for producing NK cells from undifferentiated stem cells.

After the NK cells are developed, the NK cells may be further co-cultured with artificial antigen presenting cells (aAPCs) to further expand NK cells. FIG. 5 shows a flowchart 500 of another embodiment of the method for producing natural killer cells from undifferentiated stem cells. The flowchart 500 shows steps 502, 504, 506, 508 that are similar to steps 102, 104, 106, 108 shown in FIG. 1. The flowchart 500 shows placing 502 undifferentiated stem cells in a first serum-free medium, aggregating 504 the undifferentiated stem cells in the first serum-free medium and forming spin-EBs by spin aggregation, culturing 506 the spin-EBs in the first serum-free medium for inducing production of precursor cells from the spin-EBs, culturing 508 the precursor cells in a second serum-free medium for producing the natural killer cells from the precursor cells, irradiating 510 artificial antigen presenting cells (aAPCs) with radiation to produce irradiated aAPCs, and co-culturing 512 the natural killer cells with the irradiated aAPCs. The co-culturing medium may also include interleukin 2 (IL-2). In an embodiment of the method, the step of co-culturing has a ratio of the natural killer cells to the irradiated aAPCs of 1:1.

Using Clone 9.mbIL-21 aAPCs can result in an additional 2-3 log expansion of derived NK cells. The aAPC-expanded cells maintain their NK cell phenotype as well as in vitro activity. These hESC-derived NK cells can be maintained and continually expanded in culture for more than 2 months.

Figure 6A:
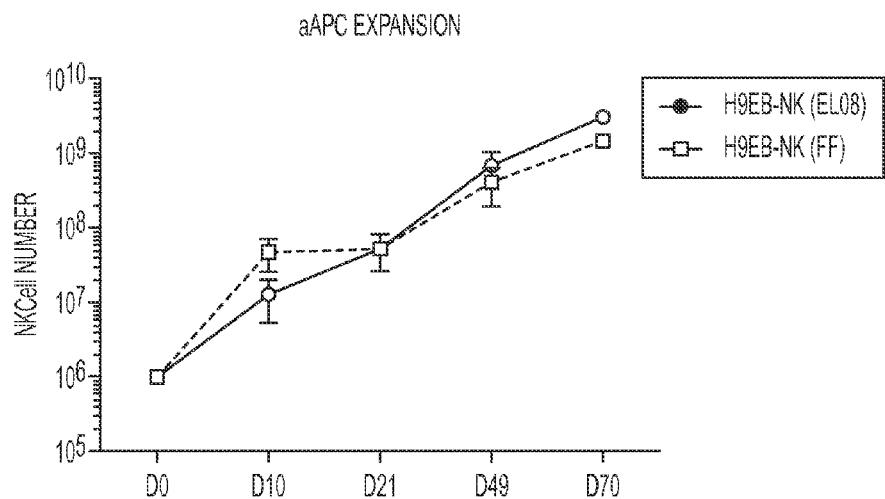
FIGS. 6A-6C show results from NK cell generated using the process shown in FIG. 5. (A) cell numbers from hESC-derived NK cells produced as FIG. 2-4, then further expanded with aAPCs for 70 days. (B) Following three weeks of expansion both the EL08-1D2 and feeder-free NK cell cultures maintain pre-expansion phenotype and were similar to expanded PB-NK cells. Each contained pure cultures of CD56$^+$ NK cells that remained CD94$^+$CD117$^-$. Each expressed high levels of KIR, CD16, and NKG2A with a small percentage of the cells expressing NKG2C (n=3). (C) Expanded NK cells maintained their in vitro function. Each was tested in a standard $^{51}$Cr release cytotoxicity assay against K562 targets (n=3 for each). Data are represented as mean±SEM.
Figure 6B:
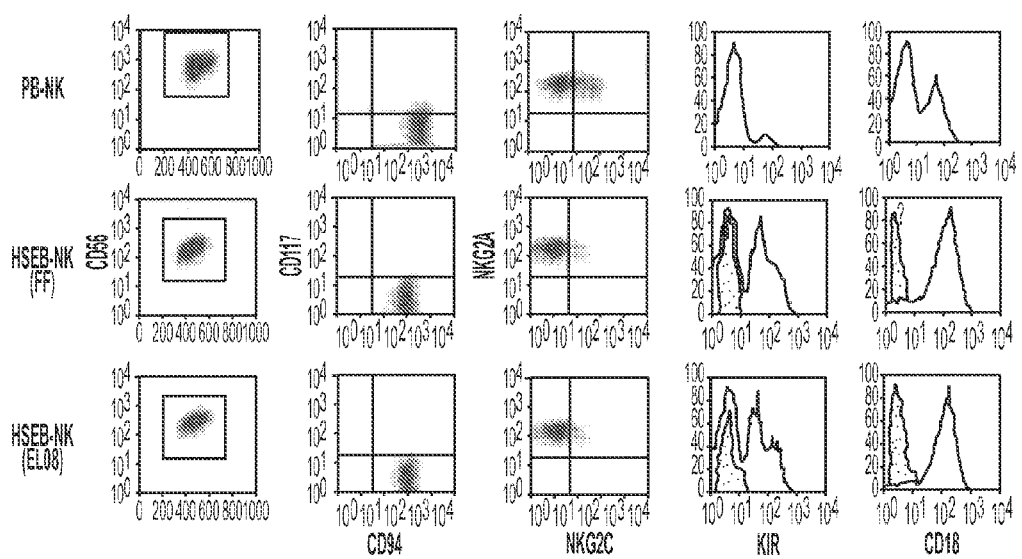
Figure 6C:
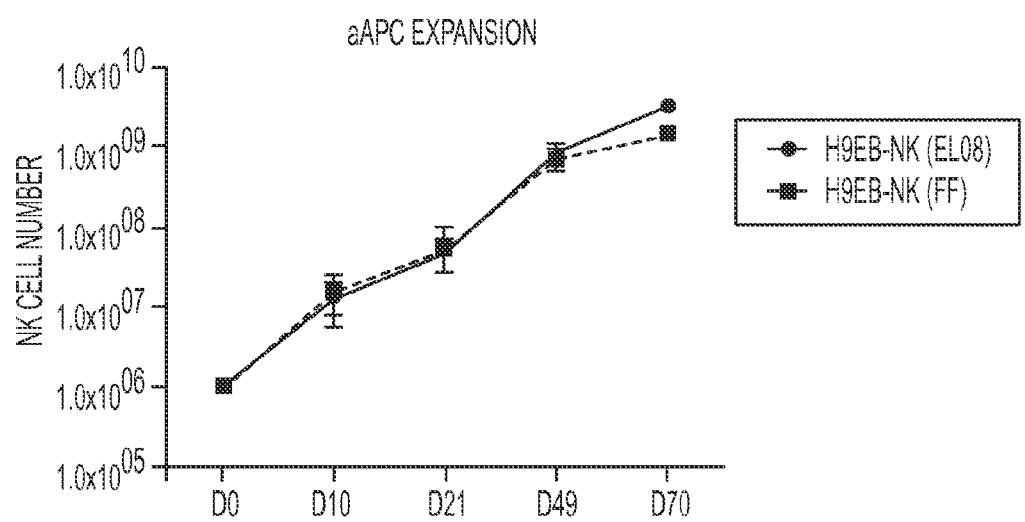

FIG. 6A shows NK cell expansion with artificial antigen presenting cells (aAPCs). Cultures containing aAPCs and 1×10$^6$ hESC-derived NK cells were evaluated for NK cell expansion at days 10, 21, 49 and 70 (D10 and 21: n=4, D49 and 70: n=2). FIG. 6B shows the analysis following 3 weeks of expansion for the NK cell cultures showing that the NK cells maintain pre-expansion phenotype and are similar to the comparative expanded PB-NK cells. Each cell cultures can contain pure cultures of CD56$^+$ NK cells that remain CD94$^+$ CD117$^-$. Each cell culture can express high levels of KIR, CD16 and NKG2A with a small percentage of the cells expressing NKG2C (n=3). FIG. 6C shows that the expanded NK cells maintain their in vitro function of killing cancer cells, when tested in a standard $^{51}$Chromium release cytotoxicity assay against K562 targets (n=3 for each). Further, studies have demonstrated that hESC and iPSC-derived NK cells kill HIV-infected cells.

With the improved efficiency and defined components of this system, clinical translation of hESC/iPSC-derived cells becomes feasible. Current adoptive NK cell-based immunotherapy uses an NK cell containing product (~50% NK cells) consisting of about 2×10$^7$ cells per kilogram. The process shown in FIG. 1 can provide this number of NK cells from about 13×10$^6$ undifferentiated hESCs or iPSCs. With the addition of the aAPCs co-culture process, as shown in FIG. 5, fewer than 10$^6$ undifferentiated hESCs/iPSCs are needed per patient at current NK cell doses.

Figure 7:
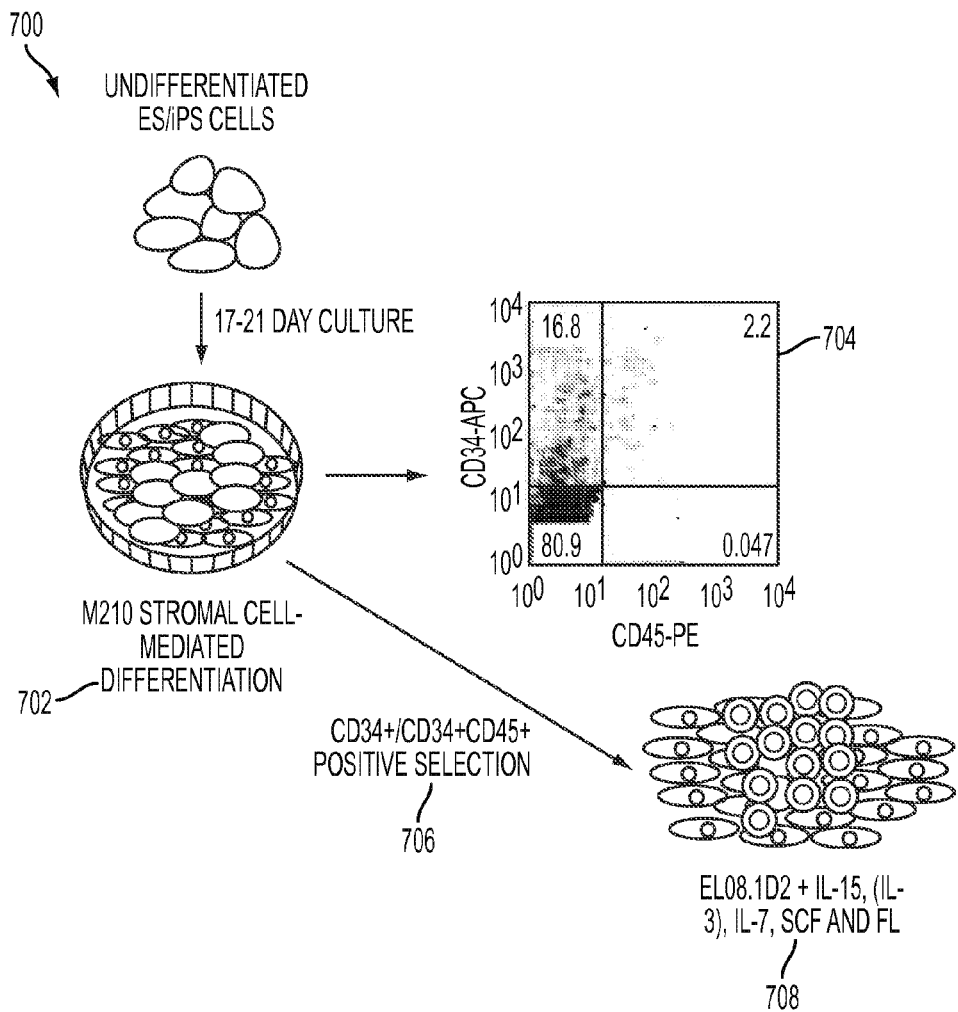
FIG. 7 shows a flow diagram of a comparative method that requires the step of co-culturing with murine stroma to support hematopoietic differentiation, and the step of cell sorting.

For comparison, productions of NK cells from hESCs and iPSCs can be performed by a method that requires co-culturing with murine stroma to support hematopoietic differentiation. The flow diagram 700 in FIG. 7 shows the comparative method for hematopoietic differentiation 702 by stromal cell co-culture using M210-B4. The undifferentiated hESCs or iPSCs are co-cultured in fetal bovine serum (FBS) for 14-24 days, and preferably 21 days. Under these conditions, hematopoietic progenitor cells, which include CD34$^+$ cells and/or CD34$^+$CD45$^+$ cells, can be developed from the hESCs or iPSCs (shown by analysis 704 by flow cytometry). Then, in this comparative method, cell sorting 706 must be performed to positively sort CD34$^+$ cells and/or CD34$^+$CD45$^+$ cells from the other cultured cells. The cell sorting 706 may be performed by magnetic sorting or florescence activated cell sorting (FACS). Then the sorted CD34$^+$ cells and/or CD34$^+$ CD45$^+$ cells are transferred to stromal cell co-culture 708 with EL08-1D2 cells in NK cell development conditions with natural killer cell promoting growth factors (that include but are not limited to cytokines, interleukins, chemokines, growth factors, colony-stimulating factors, cell-bound proteins, or any combinations thereof) for developing the NK cells from the CD34+CD45+ cells. After about 4-5 weeks, mature NK cells typically develop.

FIGS. 8A-8C shows example properties of NK cells developed from hESCs and iPSCs by using the method disclosed in FIG. 7. Two different hESC lines (H1 and H9) and three different iPSC lines (BJ1-iPS12, UCBiPS7, and DRiPS16) are shown. FIG. 8A shows the each cell lines' expression of CD34 and CD45 for each of the stem cell lines. FIG. 8B shows each of the cells lines' percent 34/45 expression ratio. FIG. 8C shows the cytotoxicity of NK cells derived from the cell lines against tumor targets (PB-NK, UCB-NK, UCB-iPS7-NK, DRiPS16-NK, H9-NK, H1-NK).

Figure 9:
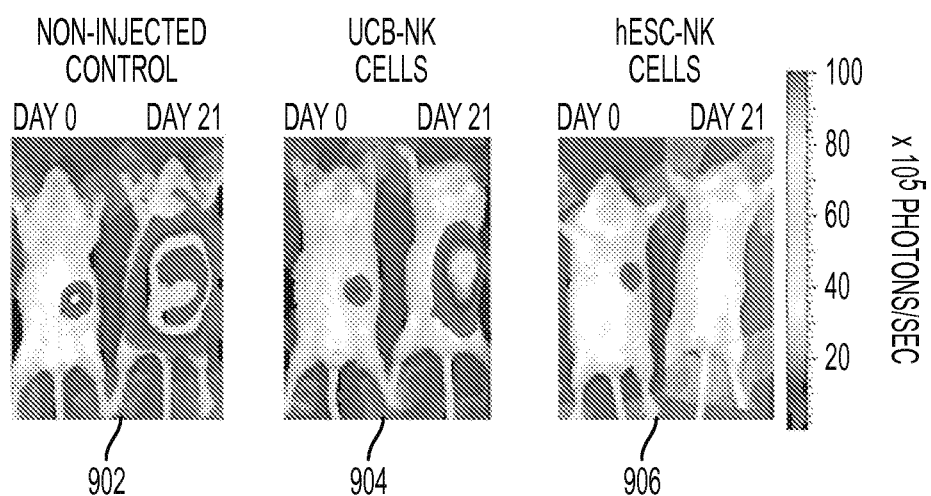
FIG. 9 shows results of in vivo tumor treatment results.

A method for killing cancerous cells include the method for producing NK cells, as disclosed above, further comprising extracting the NK cells, and delivering the NK cells to the cancerous cells. The delivering step can be by intravenous injection of the NK cells into a circulatory system of an animal or human. Alternatively, the NK cells could be injected intraperitoneally or directly into or near the cancerous cells. FIG. 9 shows a cytotoxicity comparison analysis results. In the cytotoxicity comparison analysis, a luciferase labeled leukemia cancer cell line was injected into mice. After three days, one of the mice was treated with Umbilical Cord Blood (UCB) derived NK cells, and another was treated with hESC-NK cells. FIG. 9 shows the cytotoxicity comparison results between the control mouse 902, the mouse that received UCB-derived NK cells 904, and the mouse that received hESC-NK cells 906. After twenty-one days, the cancer cells in the non-injected control 902 spread throughout the whole mouse. The UCB-derived NK cells were able to inhibit proliferation to some degree in the mouse 904. The hESC-NK cells eliminated the cancer cells in the mouse 906. These results show the ability of the hESC-NK cells to eliminate cancer cells quickly and efficiently. Thus, the hESC-NK cells and iPSC-NK cells are able to lyse human tumor cells by both direct cell-mediated cytotoxicity and antibody-dependent cellular cytotoxicity. Further, activated hESC-NK cells and iPSC-NK cells up-regulate cytokine production. Accordingly, hESC-NK cells could serve as a "universal" source of anti-tumor lymphocytes for novel clinical therapies. Further, iPSC-NK cells have similar ability to eliminate cancer cells as quickly and efficiently as the hESC-NK cells. It is expected that iPSC-NK cells will be able to be efficiently derived on a patient-specific basis using the method disclosed above for killing cancer cells.

Example 2

Clinical-Scale Derivation of Natural Killer Cells from Human Pluripotent Stem Cells for Cancer Therapy Maintenance and stromal cell-mediated differentiation of hESCs/iPSCs. hESCs (H9 and H1) and iPSCs (UCBiPS7, NHDF-iPS, BJ1-iPS) were maintained on mouse embryonic fibroblasts (MEF). Stromal cell-mediated differentiation of hematopoietic progenitors on M210-B4 (American Type Culture Collection, Manassas, Va.) cells was done as previously described (Hill et al., 2010; Tian et al., 2009; Woll et al., 2009). Briefly, undifferentiated hESCs or iPSCs were placed on M210-B4 in medium containing RPMI 1640 (Invitrogen, Carlsbad, Calif.), 15% defined fetal bovine serum (FBS) (Hyclone, Logan, Utah), 2 mM L-glutamine (Cellgro, Manassas, Va.), 1% non-essential amino acids (Invitrogen), 1% penicillin/streptomycin (Invitrogen), and 0.1 mM β-mercaptoethanol (Invitrogen). Media was changed three times per week, and after 18-21 days cells were harvested for CD34+CD45+ progenitor cell enrichment (Woll et al., 2009). One hundred thousand CD34+CD45+ cells were placed onto EL08-1D2 stroma with 1 mL NK cell initiating cytokines (interleukin [IL]-3, IL-7, IL-15, stem cell factor [SCF], fms-like tyrosine kinase receptor-3 ligand [FLT3L], all from Peprotech, Rocky Hill, N.J.). NK cell cultures were refreshed with 0.5 mL of cytokine-containing media every 4-5 days. Mature NK cells were measured at 28-35 days of culture on EL08-1D2.

Generation of Spin EBs.

In order to generate spin EBs amenable to aggregation, hESCs and iPSCs were passaged in TrypLE Select (Invitrogen) on low-density MEFs (90,000 cells/well) for a minimum of 10 passages. For the spin EB studies, the inventors used an H9 line modified with a green fluorescence protein/firefly luciferase construct (Tian et al., 2009) for future in vivo experiments. For iPSCs, the inventors tested the UCBiP7 line derived from umbilical cord blood (UCB) CD34+ hematopoietic progenitors. To generate TypLE adapted hESCs or iPSCs, cultures at approximately 60%-70% confluence were dissociated and filtered through a 70-μm sterile filter. Only pure cultures of hESCs lacking any signs of differentiation were used. Cells were passaged 1:1 on low-density MEFs in regular hESC media until cellular proliferation allowed passing at more dilute ratios, typically occurring around passage 10. To set up TrypLE passaged hESCs into stage I spin EBs, adapted cells at approximately 70% confluence were dissociated with TrypLE and filtered through a 70-μm filter to remove any clumps. Cells were then counted and placed at a concentration of 3000 cells per well (100 μl volume) of a round-bottom 96-well plate in BPEL (bovine serum albumin polyvinyl alcohol essential lipids) medium containing SCF (40 ng/ml), vascular endothelial growth factor (20 ng/ml), and bone morphogenic protein 4 (20 ng/ml). BPEL medium was made in 200-ml volumes and contained Iscove's modified Dulbecco's medium (86 ml; Invitrogen), F12 Nutrient Mixture with GlutaMAX I (86 ml; Invitrogen), 10% deionized bovine serum albumin (5 mL; Sigma-Aldrich, St. Louis, Mo.), 5% polyvinyl alcohol (10 ml; Sigma-Aldrich), linoleic acid (20 μL of 1 mg/ml solution; Sigma-Aldrich), linolenic acid (20 μL of 1 mg/ml solution; Sigma-Aldrich), Synthecol 500× solution (Sigma-Aldrich), α-monothioglyceral (Sigma-Aldrich), protein-free hybridoma mix II (Invitrogen), ascorbic acid (5 mg/ml; Sigma-Aldrich), GlutaMAX I (Invitrogen), insulin-transferrin-selenium 100× solution (Invitrogen), and penicillin/streptomycin (Invitrogen). The outer wells of the plate were filled with sterile water to prevent any evaporation of the medium. Plates were then spin-aggregated at 1,500 RPMs for five minutes at room temperature and placed undisturbed in a 37° C. incubator with 5% CO$_2$. Cells were not removed for at least three days to ensure formation of spin EBs in the plates.

NK Cell Differentiation from Spin EBs.

At day 11 of spin EB differentiation, 6 wells of a 96-well plate were directly transferred to one well of a 24-well plate in NK cell initiating cytokines, as described above. Initially, the 24-well plates contained 100,000 irradiated (3000 rads) EL08-1D2 cells per well. For completely defined conditions, 6 wells of spin EBs were directly transferred to uncoated 24-well plates. On the day of analysis each well was collected, filtered, and washed.

Flow cytometry. The following antibodies were used: CD34-APC, CD45-PE, CD31-PE, CD31-APC, CD-73PE, CD43-PE, NKp46-PE, NKp44-PE, CD56-APC, NKG2D-PE, TRAIL-PE, FAS ligand-PE, CD16-PercpCy5.5, and CD117-PercpCy5.5, all from Becton, Dickson and Company (Franklin Lakes, N.J.). CD158a/h-PE, CD158j-PE, CD158i-

PE, CD158e1/e2, and CD159a-PE and -APC were obtained from Beckman Coulter (Fullerton, Calif.). CD107aPercpCy5.5 and INF-γ PacBlue were obtained from eBioscience Inc. (San Diego, Calif.). Flow cytometry was done on a BD FACSCalibur or LSRII (BD Biosciences, San Diego, Calif.), and data were analyzed using FlowJo (Tree Star, Ashland, Oreg.).

Gene Expression.

For reverse transcription-polymerase chain reaction (RT-PCR), total RNA was prepared from cells using an RNeasy mini-kit (Qiagen, Valencia, Calif.). Following isolation of total RNA, complementary DNA was made using Superscript III reverse transcriptase (Life Technologies, Grand Island, N.Y.). RT-PCR was then performed on the resulting cDNA with the primers and cycle number listed in Table 1 using the Peltier Thermal Cycler-200 Annealing temperature was set at 55° C. for all primers except OCT4, which had an annealing temperature of 60° C. Products from the PCRs were then separated on a 0.9% agarose gel via electrophoresis.

no. 331904; Biolegend). Following an incubation of five hours, cells were harvested and analyzed as described above.

CD107a and IFNγ Assays.

NK cells were incubated with or without K562 targets at 1:1 effector to target ratios. CD107a-PerCPCy5.5 antibody was added to each well and allowed to incubate for one hour. GolgiStop and GolgiPlug (BD Biosciences) were then added to each well and incubated for another four hours. At the completion of incubation, cells were washed, stained with CD56APC, and fixed with 2% paraformaldehyde for 10 minutes on ice. Cells were then permeabilized with 1% saponin for 20 minutes at 4° C., washed, and stained for IFNγ.

Stromal Cell Functional Assays.

To assess the endothelial and mesenchymal stromal cell (MSC) characteristics of the stroma derived in NK cell cultures, nonadherent cells were first washed away and then the adherent layer was trypsinized and washed. Cells were stained with endothelial (CD31) and MSC (CD73) markers, as well as the hematopoietic (CD45), monocyte/macrophage

TABLE 1

Primers and PCR cycles.

| Primer Name | Direction | Sequence 5'→3' | SEQ ID NO. | Cycles | Amplicon Length (bp) |
|---|---|---|---|---|---|
| E4BP4 | Sense | AAA ATG CAG ACC GTC AAA AAG GA | 1 | 25 | 100 |
| E4BP4 | Antisense | CTT CTG ACA CTT CCG TTA AAG CA | 2 | 25 | 100 |
| E2A | Sense | TGT GCC AAC TGC ACC TCA A | 3 | 35 | 116 |
| E2A | Antisense | GGG ATT CAG GTT CCG CTC TC | 4 | 35 | 116 |
| ID2 | Sense | GAC CCG ATG AGC CTG CTA TAC | 5 | 25 | 165 |
| ID2 | Antisense | AAT AGT GGG ATG CGA GTC CAG | 6 | 25 | 165 |
| ID3 | Sense | TCG GAA CGC AGT CTG GCC ATC | 7 | 25 | 258 |
| ID3 | Antisense | CTC GGC TGT CTG GAT GGG AAG | 8 | 25 | 258 |
| PAX5 | Sense | CCA GTC CCA GCT TCC AGT CAC AG | 9 | 25 | 173 |
| PAX5 | Antisense | GGA GAC TCC TGA ATA CCT TCG TCT C | 10 | 25 | 173 |
| OCT4 | Sense | CCC CAG GGC CCC ATT TTG GTA CC | 11 | 20 | 309 |
| OCT4 | Antisense | CTT CCC TCC AAC CAG TTG CCC CAA AC | 12 | 20 | 309 |
| GAPDH | Sense | CCA CTC CTC CAC CTT TGA C | 13 | 25 | 102 |
| GAPDH | Antisense | ACC CTG TTG CTG TAG CCA | 14 | 25 | 102 |

In Vitro Cytotoxicity.

Tumor targets (K562, SVP10, S2013, OPM2, RPMI 8226, U266) were incubated with chromium 51 ($^{51}$Cr) for two hours at 37° C., washed three times, and co-cultured with NK cells at indicated effector to target (E:T) ratios. After a period of four hours, cells were harvested and analyzed. Specific $^{51}$Cr lysis was calculated using the equation: Percentage of specific lysis=100×(Test release−Spontaneous release)/(Maximal release−Spontaneous release). For redirected antibody-dependent cellular cytotoxicity (ADCC) assays, P815 targets were incubated as described above. Thirty minutes prior to the addition of the NK cells to target cells, effectors were incubated with either isotype control (catalog no. 400153; Biolegend, San Diego, Calif.) or NKp46 antibodies (catalog (CD14, CD15), and dendritic cell (CD11c) markers. To assess the ability of each of the stromal cell layers (EL08-1D2, human umbilical vein endothelial cells [HUVECs], feeder-free stroma) to support NK cell development, each was plated at 100,000 cells per well of a 24-well plate and irradiated (3,000 rads). HUVECs were grown as previously described (Hill et al., 2010). Each well was then seeded with 500 CD34$^{+}$ cells from umbilical cord blood. The no-stroma conditions contained UCB CD34$^{+}$ cells and media alone. Cells were then cultured under standard NK cell conditions as described above.

Artificial Antigen-Presenting Cell Expansion.

To expand hESC-derived NK cells from EL08-1D2 or feeder-free conditions, each was placed in culture with clone 9.mbIL-21 artificial antigen-presenting cells (aAPCs) (Denman et al., 2012). For the first week of culture, aAPCs were irradiated with 10,000 rads and added to NK cells at a ratio of 2:1 (day 0). The following stimulations with aAPCs (every 7 days) were at a 1:1 ratio. Cultures were fed three times per week (RPMI 1640, 15% FBS, 1% penicillin/streptomycin, 50 U/ml interleukin-2), maintaining cell counts at 250,000 cells/mL for optimal expansion.

Statistical Analysis.

Differences between groups were compared using Student t test post hoc analysis or ANOVA using Prism 4 (GraphPad Software, San Diego, Calif.). Results were considered significant at P values of 0.05 or less.

hESC- and iPSC-Derived Hematopoietic Progenitor Cells can Develop into NK Cells.

Figure 10:
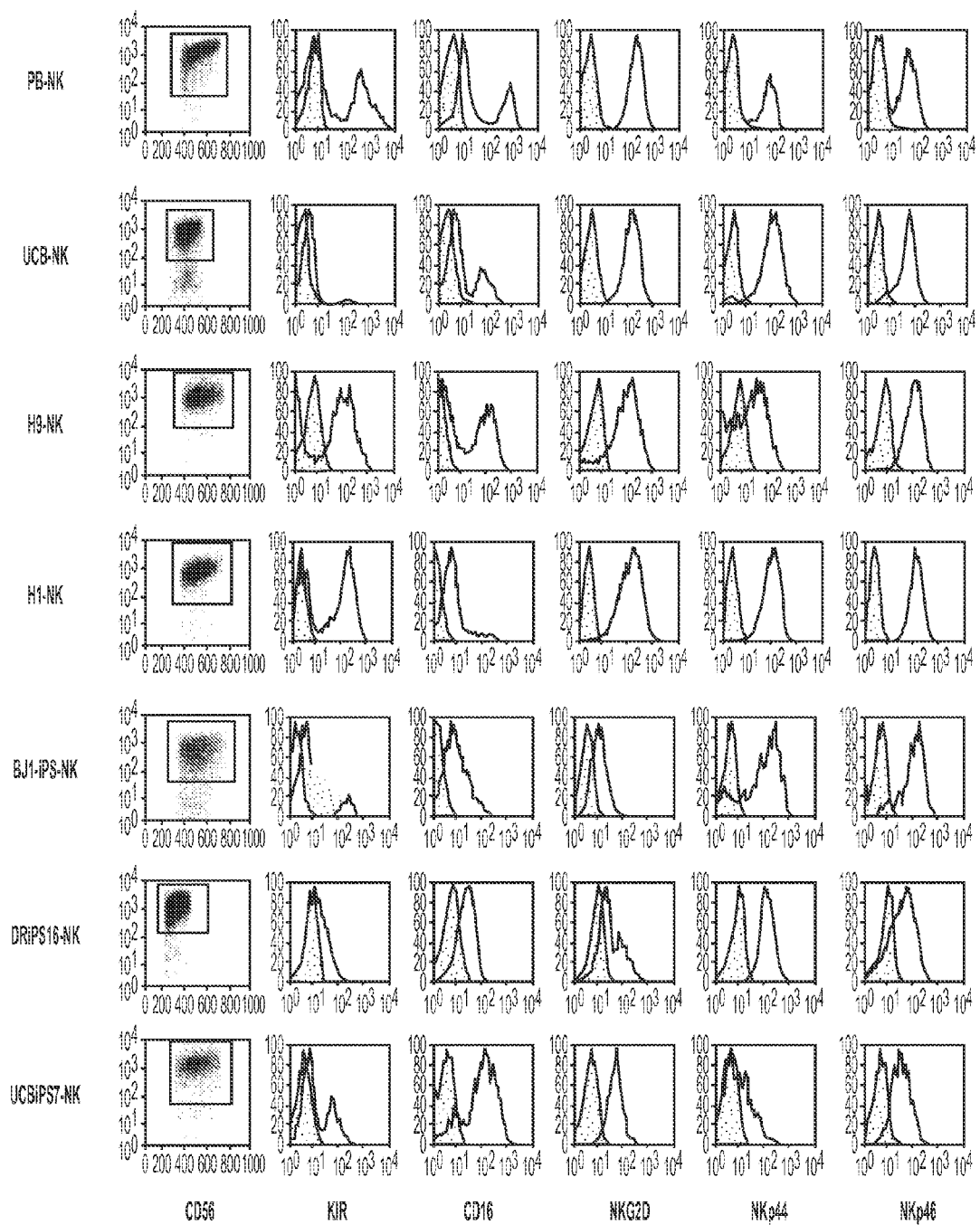
FIG. 10 Derivation of functional NK cells from human embryonic stem cells (hESCs) and induced pluripotent stem cells (iPSCs). NK cells derived from hESCs, iPSCs (BJ1-iPS, NHDF-iPS, UCB-iPS), or UCB CD34$^+$ cells or isolated from adult peripheral blood (PB-NK). Histogram plots are gated on CD56' events. KIR plots used a cocktail of KIR antibodies (CD158a/h, CD158e1/e2, and CD158i). Similar to PB-NKs, hESC- and iPSC-derived NK cells expressed markers of functionally mature NK cells (CD16, NKG2D, NKp44, NKp46, CD161). Histograms are representative of at least three individual experiments. Abbreviations: iPS, induced pluripotent stem; KIR, killer immunoglobulin-like receptor; NK, natural killer; PB, peripheral blood; UCB, umbilical cord blood.

Initial studies used a stromal cell coculture model (Ni et al., 2011; Woll et al., 2009; Woll et al., 2005) to compare hematopoietic and NK cell developmental potential of two different hESC lines (H1 and H9) and three different iPSC lines (BJ1-iPS12, UCBiPS7, and DRiPS16). UCBiPS7 and DRiPS16 were derived and characterized in the inventors' laboratory. For this method, hESCs or iPSCs are cultured on M210-B4 stromal cells in medium containing only FBS. Over a period of three weeks, all hESC and iPSC lines generated hematopoietic progenitor cells coexpressing CD34 and CD45 (FIGS. 8A, 8B, and 10). Whereas the H9 cells gave rise to the highest percentage of hematopoietic progenitor cells expressing CD34 and CD45 (6.46±1.75%), other hESC and iPSC lines yielded consistently lower numbers: 1.45±0.18% for H1 hESCs, 2.46±1.71% for UCBiPS7, 0.92±0.14% for DRiPS16, and 1.43±0.35% for the BJ1-iPS line (FIG. 8B). These numbers are similar to what the inventors and others have previously shown, where the efficiency of hematopoietic development using the stromal cell-based system is relatively limited (Choi et al., 2009; Ledran et al., 2008). After demonstrating that different iPSC lines give rise to varying numbers of hematopoietic progenitor cells, we generated NK cells from each of the hESC/iPSC-derived CD34$^+$CD45$^+$ cell populations. Here, CD34$^+$CD45$^+$ cells were sorted and cultured in conditions known to support human NK cell development, including the murine stromal cell line EL08-1D2 and cytokines (SCF, FLT3L, IL-15, IL-7, IL-3) (Woll et al., 2009) for four weeks. Although distinct lines of hESCs or iPSCs gave rise to varying frequencies of hematopoietic progenitor cells, each cell line was able to produce phenotypically mature and functional NK cells. Both hESC- and iPSC-derived NK cells consist of a homogenous population of cells expressing CD56, killer immunoglobulin-like receptors (KIRs), CD16, NKp44, NKp46, and NKG2D (FIG. 10). Also, NK cells from all five hESC/iPSC populations were able to kill tumor cells similar to NK cells isolated from peripheral blood (PB-NK) (FIG. 8C). These results demonstrated that although individual hESCs and iPSCs have reproducible differences in their ability to derive hematopoietic progenitor cells, each was capable of making mature, cytolytically active NK cells.

Enhanced Generation of Progenitor Cells Eliminates Cell Sorting in the Derivation of hPSC-Derived NK Cells.

In an effort to better understand specific stimuli required to mediate the derivation of NK cells from hESCs or iPSCs and to improve culture efficiency, the inventors took a stepwise approach to translate these methods to completely feeder-free and serum-free culture system. First, undifferentiated hESCs and iPSCs were supported to produce hematopoietic progenitor cells using a "spin EB" method (Ng et al., 2008; Ng et al., 2005). Here, defined numbers (3,000 cells) of undifferentiated hESCs (H9) or iPSCs (UCBiPS7) were spin aggregated in serum-free medium in a 96-well format (FIG. 2). Over a period of 11 days these cultures demonstrated hematopoietic cell development and proliferation (FIG. 4A). Not only did this method remove the need for M210-B4 murine stroma, the inventors found that it allows higher frequency and more consistent generation of hematopoietic progenitor cells from both hESCs and iPSCs. For hESCs the inventors found that a majority of the hematopoietic cells expressed CD34 (55.9±6.4%), with many coexpressing CD43 (41.8±9.51%) or CD45 (26.2±6.6%) (FIGS. 4B and 4C). iPSCs also generated CD34$^+$ cells (12.06±5.40%) and CD45$^+$ cells (3.20±1.43%), although typically fewer than hESCs. This method provides significant improvement over the M210-B4 stromal-based system (FIGS. 8A, 8B, and 10) for both hESCs and iPSCs.

Figure 11:
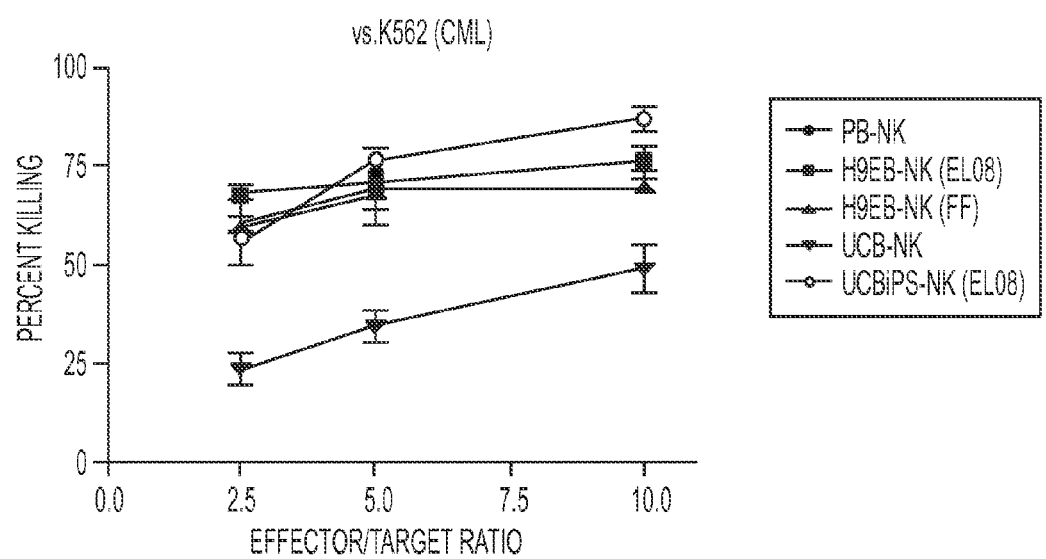
FIG. 11 Derivation of functional NK cells in feeder-free conditions. Cytotoxicity assay against the leukemic cell line K562 (N=4 per cell type). hESC- and iPSC-derived NK cells kill K562 cells similarly to activated PB-NK cells and significantly better than UCB-NK cells (p=0.0054). Data are represented as mean±SEM. Abbreviations: CML, chronic myelogenous leukemia; ES, embryonic stem; hESC, human embryonic stem cell; iPSC, induced pluripotent stem cell; NK, natural killer; PB, peripheral blood; UCB, umbilical cord blood.
Figure 14:
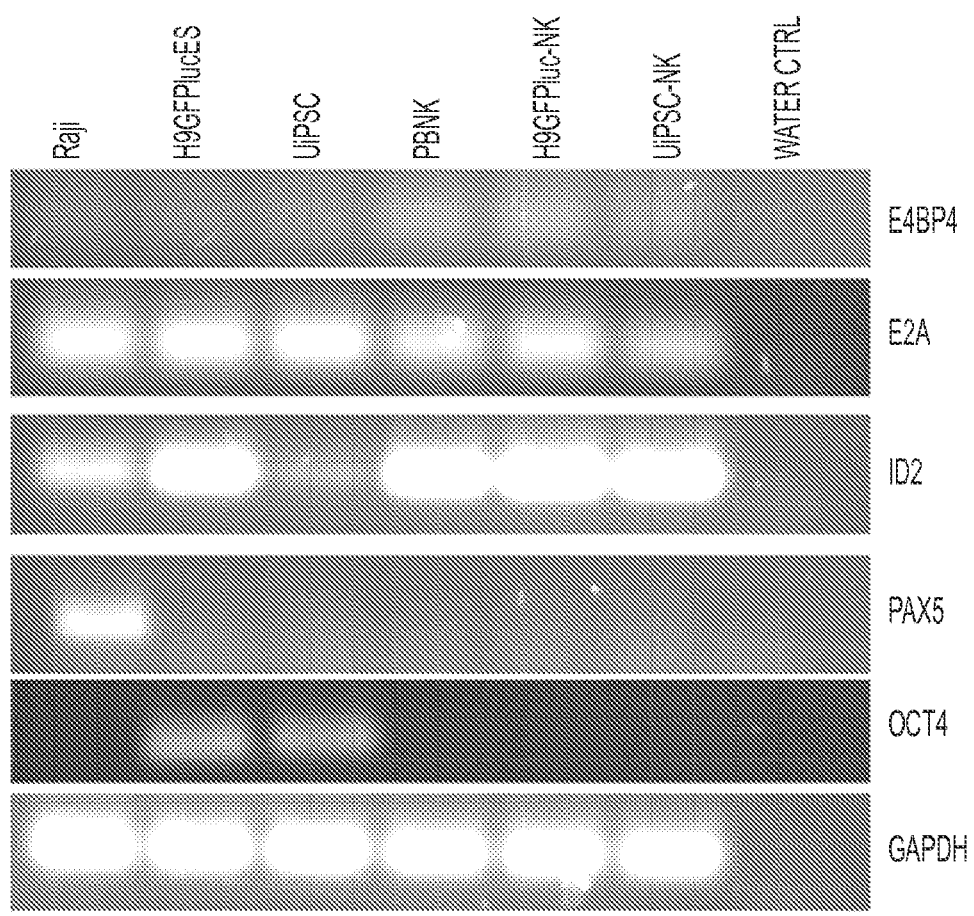
FIG. 14 Spin EB-derived NK cells express lineage specific factors. Each NK cell population was tested by reverse transcriptase PCR for genes important in NK cell development. Compared to PB-NK cells, hESC- and iPSC-derived NK cells express E4BP4, E2A, and ID2. They do not express the pluripotency factor OCT4 or the B-cell lineage-specific transcription factor PAX5.
Figure 15:
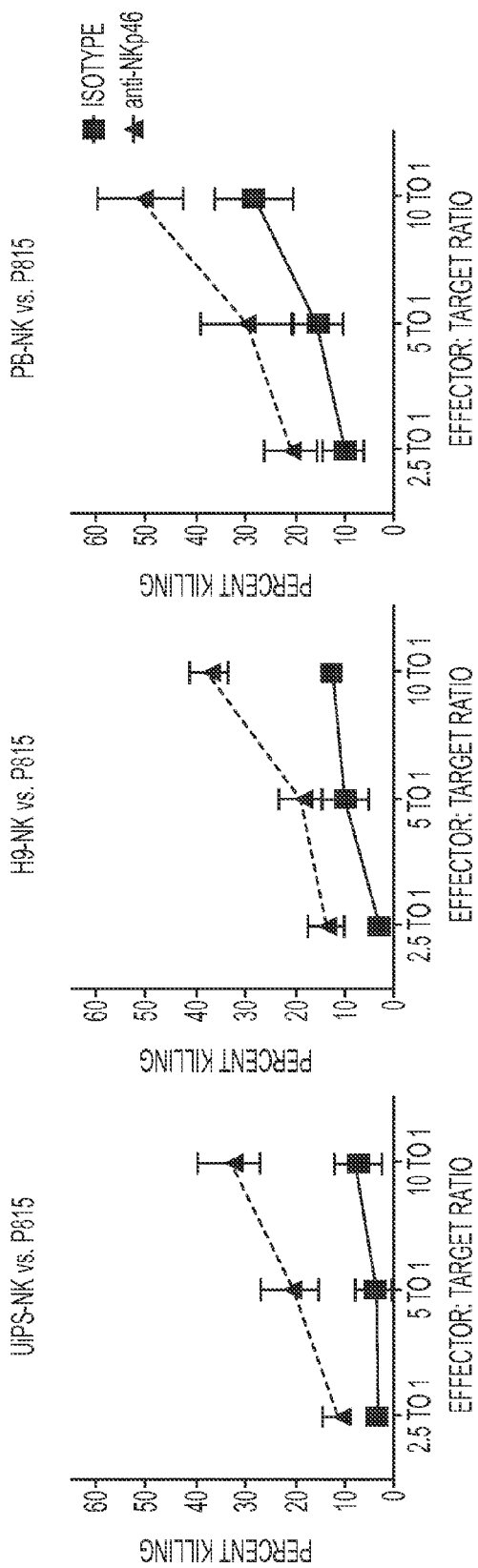
FIG. 15 Spin EB-derived NK cells can be triggered through the activating receptor NKp46. NK cells from hESCs, iPSCs, and peripheral blood were tested for redirected killing through the NKp46 activating receptor, or reverse ADCC. Each effector line was pre-incubated with isotype control or anti-NKp46 antibodies prior to adding to P815 target cells (which can bind the Fc portion of an antibody). NK cells were then co-incubated with P815 target cells at increasing effector to target ratios.

The inventors next tested the ability of the hematopoietic progenitor cells generated in the spin EB system to derive NK cells. To do this, the inventors directly transferred spin EBs, without dissociation or sorting, into NK cell initiating conditions containing cytokines and EL08-1D2 stroma. As previously shown, this stage II culture system provides reliable development of NK cells over a period of four weeks (Ni et al., 2011; Woll et al., 2009). Similar to stromal cell coculture-derived progenitor cells, spin EB-derived hematopoietic progenitors acquired NK cell surface markers culminating in a mature NK cell phenotype (FIG. 4D). Indeed, the inventors found that spin EB-derived cells differentiate into a homogenous population of CD56$^+$ NK cells expressing CD94 in the absence of CD117 (Woll et al., 2009). Additionally, these cells expressed high levels of KIRs, CD16, NKG2D, NKp46, and TRAIL. They also have a gene expression profile consistent with the NK cell lineage. They expressed ID2, E2A, and E4BP4 (FIG. 14). They did not express the B cell lineage-specific transcription factor PAX5. Also, in contrast to the parent lines, hESC- and iPSC-derived NK cells did not express the pluripotency factor OCT4. Spin EB-derived NK cells (from both hESCs and iPSCs) not only had the correct phenotype and genotype but killed K562 tumor cells at a similar level to PB-NK cells and were more cytotoxic than UCB-derived NK cells (FIG. 11). Additionally, the inventors demonstrated specific killing mediated by the activating receptor, NKp46, expressed on the hESC- and iPSC-derived NK cells. Similar to PB-NK cells, hESC- and iPSC-derived NK cells could be triggered, through a reverse ADCC assay, to kill P815 targets (FIG. 15). These data demonstrate that not only does the spin EB approach provide a feeder-free system to generate high numbers of hematopoietic progenitor cells, but that these progenitors do not require sorting to differentiate into phenotypically mature NK cells with cytotoxic function similar to activated PB-NK cells.

hPSC-Derived Stroma Support NK Cell Development from Hematopoietic Progenitor Cells.

Figure 12A:
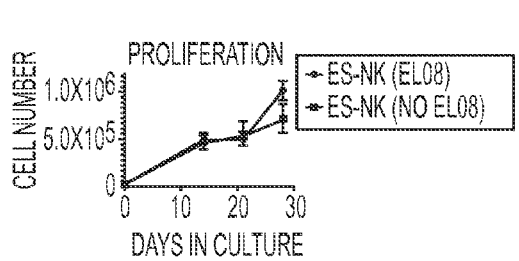
FIG. 12 hPSC-derived stroma support development of mature NK cells. (A) hESC-derived NK cells proliferated in the presence or absence of murine EL08-1D2 stromal cells. At four weeks of culture with or without EL08 cells, the stromal cells provided 56.8-fold expansion and feeder-free cells expanded 40.4-fold. N=4 for each condition. (B) hESC-derived stroma following two weeks of NK cell culture. Cells were imaged at 40× magnification. The hematopoietic cells were then washed away and cells were reimaged to evaluate only the stromal layer. The stromal cells also express GFP, indicating their hESC origin (the parent H9 line used is engineered to be GFP$^+$). (C) Stroma from feeder-free conditions expressed surface antigens typical of both endothelial (CD31) and mesenchymal stromal cells (MSCs), but do not express the pan-hematopoietic marker CD45 or myeloid markers (CD14, CD15, CD11c). (D) Stroma derived from feeder-free conditions supported the development of NK cells from UCB CD34$^+$ HSCs. Each stromal layer (EL08-1D2, HUVEC, feeder-free stroma) was evaluated at day 28 for the presence of NK cells (CD56). A no-stroma, cytokine-only condition is also shown. CD56$^+$ events were then evaluated for the expression of CD117, CD94, NKG2A, and KIR (N=2). Abbreviations: ES, embryonic stem; GFP, green fluorescence protein; HUVEC, human umbilical vein endothelial cell; KIR, killer immunoglobulin-like receptor; NK, natural killer.
Figure 12B:
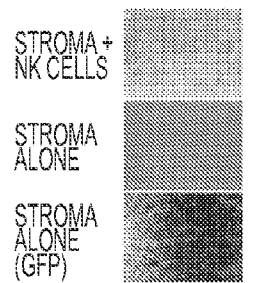
Figure 12C:
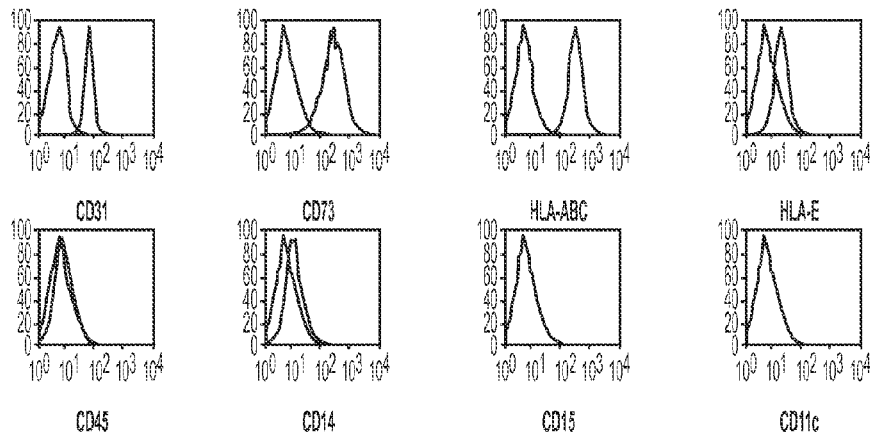
Figure 12D:
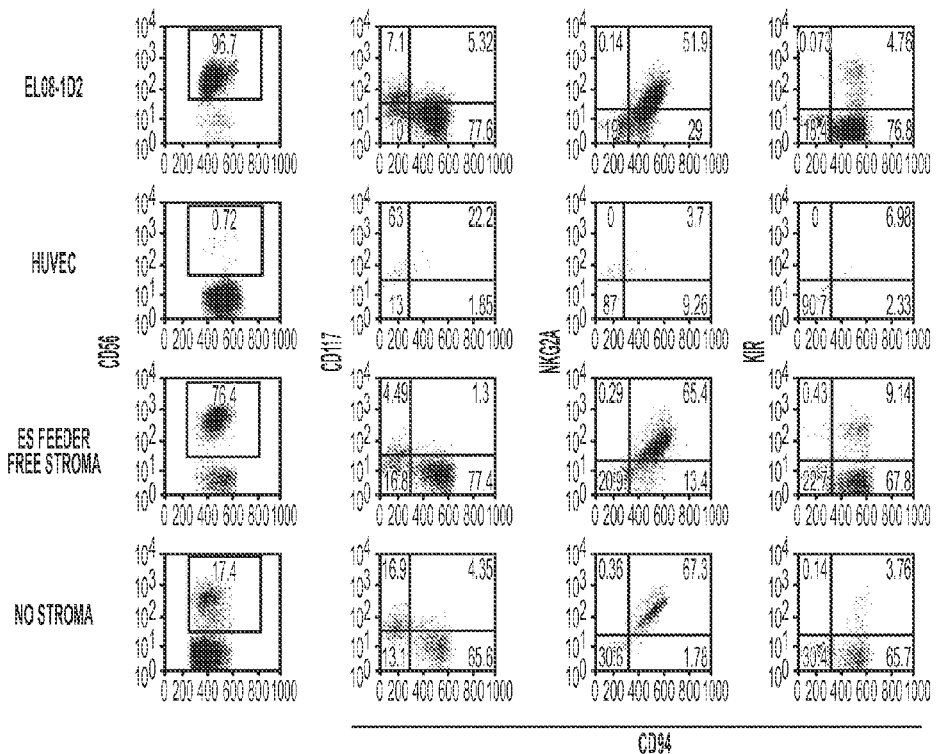
Figure 16A:
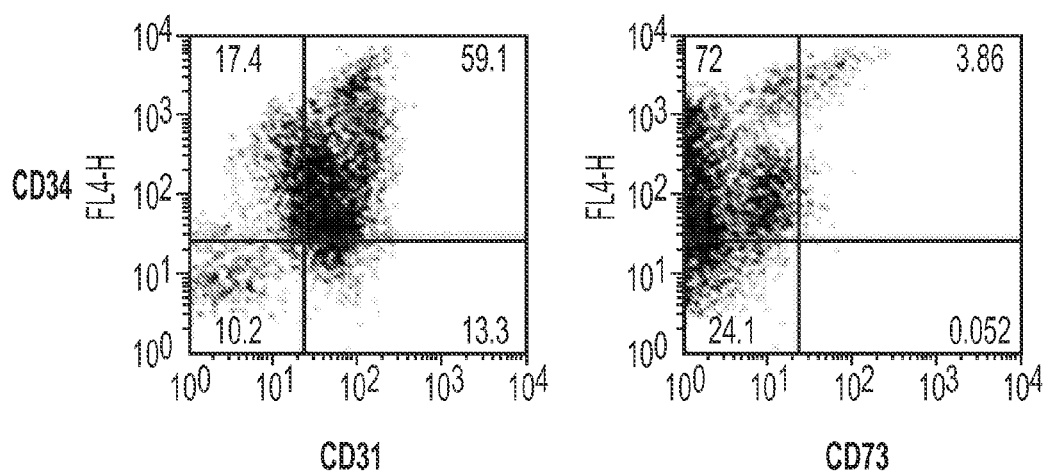
FIG. 16 Spin EBs contain progenitors for both endothelial cells and mesenchymal stromal cell. (A) Day 11 (day of transfer to NK cell conditions) spin EBs were analyzed for the presence of the endothelial (CD31) or mesenchymal stromal cell (CD73) markers. A large portion of the CD34$^+$ cells co-express CD31. Flow cytometry plots are representative of at least three independent experiments.
Figure 18A:
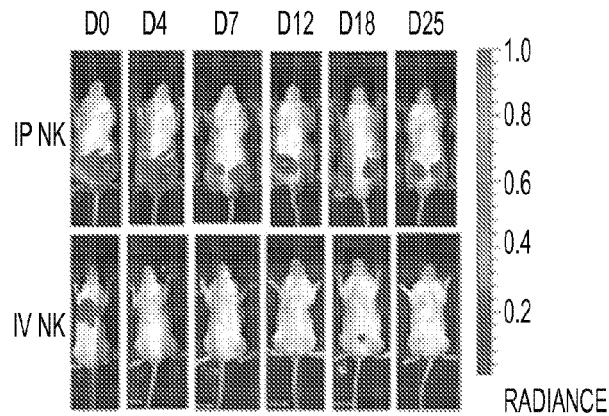
FIG. 18 Persistence of hESC-derived NK cells. (A) Persistence of hESC-derived NK cells injected IV versus IP was monitored by bioluminescent imaging at the indicated time points (D=days) following NK cell injection. (B) Quantification of the hESC-derived NK cell luciferase signal in mice receiving cells intravenous (IV) versus intraperitoneal (IP) and compared to noninjected controls. IP injected NK cells persisted for the entire 25 days, whereas IV injected cells were undetectable by day 4. (C) Analysis of some mice at day 19 to assess engraftment of IV and IP injected NK cells within the spleen, bone marrow, peritoneum, and peripheral blood compared to noninjected controls. hESC-derived NK cells were analyzed for their expression of GFP or staining of CD56 and CD45 surface antigens. Plots are representative of 4 IP mice and 3 IV mice. For the noninjected control group, two mice were analyzed.
Figure 18B:
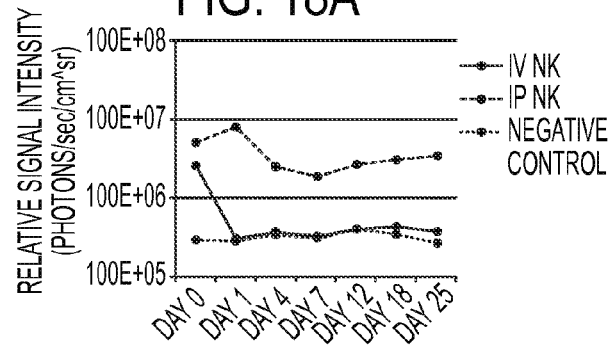
Figure 18C:
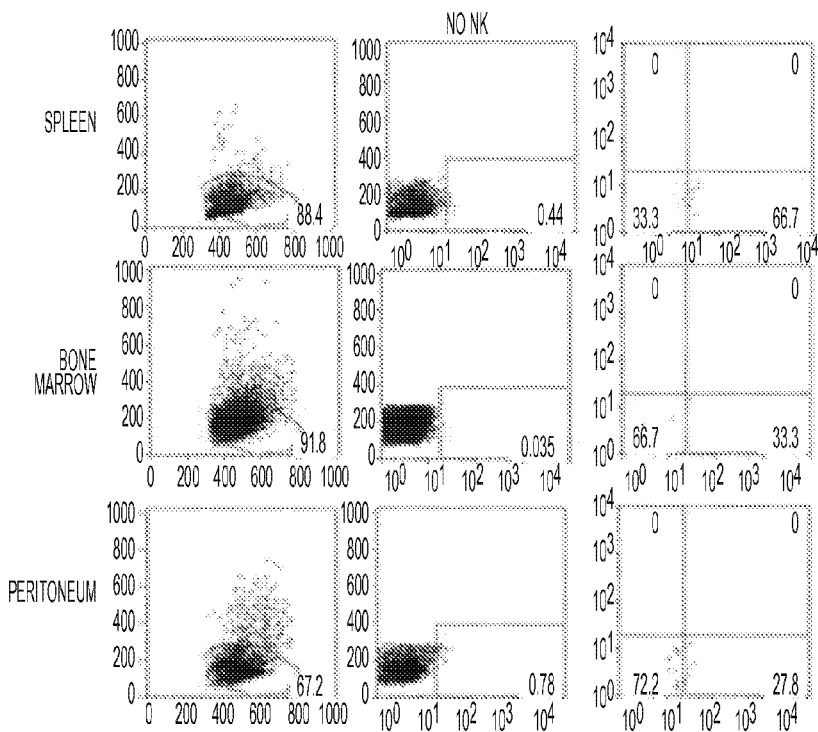
Figure 18C:
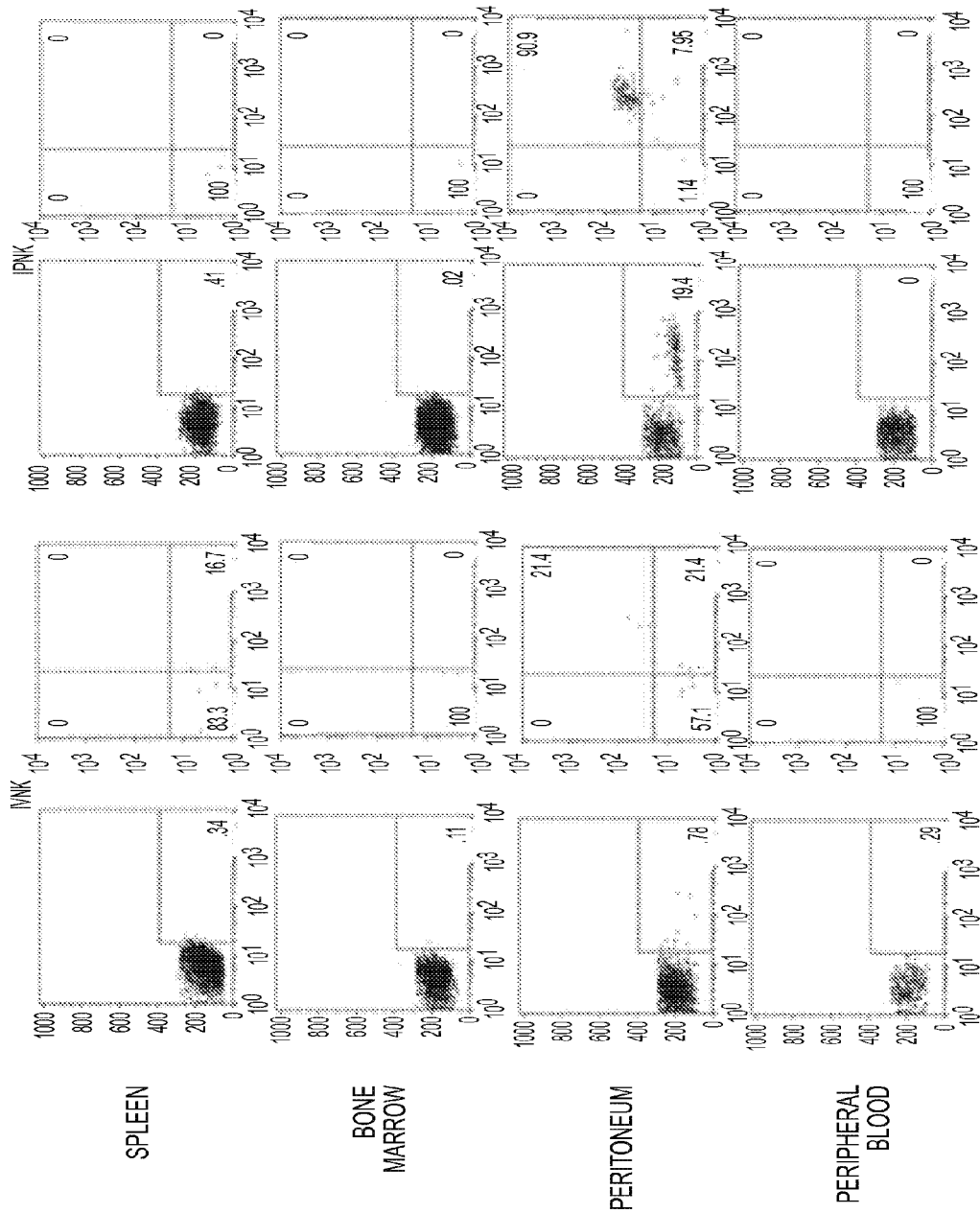

To more completely define the conditions required for NK cell development from hESCs and iPSCs, the inventors next tested spin EB-derived cells in a feeder-free and serum-free stage II system containing NK cell promoting cytokines (IL-3, IL-7, IL-15, SCF, FLT3L) without EL08-1D2 or other exogenous stromal cells (FIG. 2). Within the first two weeks following transfer, there was proliferation of nonadherent hematopoietic cells from the spin EBs at a similar level to what is seen with EL08-1D2 stroma (FIG. 12A). Additionally, the inventors found these cells started to produce their own adherent cells in culture (FIG. 12B). The inventors have previously demonstrated development of endothelial cells (ECs) and mesenchymal stromal cells (MSCs) from hESCs (Hill et al., 2010; Kopher et al., 2010). Here, the inventors demonstrated both of these cell types (CD34$^+$CD31$^+$ ECs and CD34+CD73+ MSCs) (FIG. 16) are routinely produced in the spin EB cultures. As nonhematopoietic cells such as ECs and MSCs that reside in the bone marrow are known to support NK cells in vivo, the inventors hypothesized that these adherent cells could efficiently support growth of NK cells from hESCs in vitro (Carson et al., 1997; Mrozek et al., 1996). Notably, the inventors found the spin EB stromal cell layers express high levels of CD31 and CD73 (FIG. 12C) in addition to MHC class 1 molecules (HLA-A,B,C and HLA-E) known to be important for NK cell development and acquisition of KIRs (Kim et al., 2005). Additionally, these spin EB-derived stromal cells support the development of NK cells from UCB CD34+ cells similar to EL08-1D2 stroma and more efficiently than human umbilical vein endothelial cells or cytokines alone (FIG. 12D).

Figure 13A:
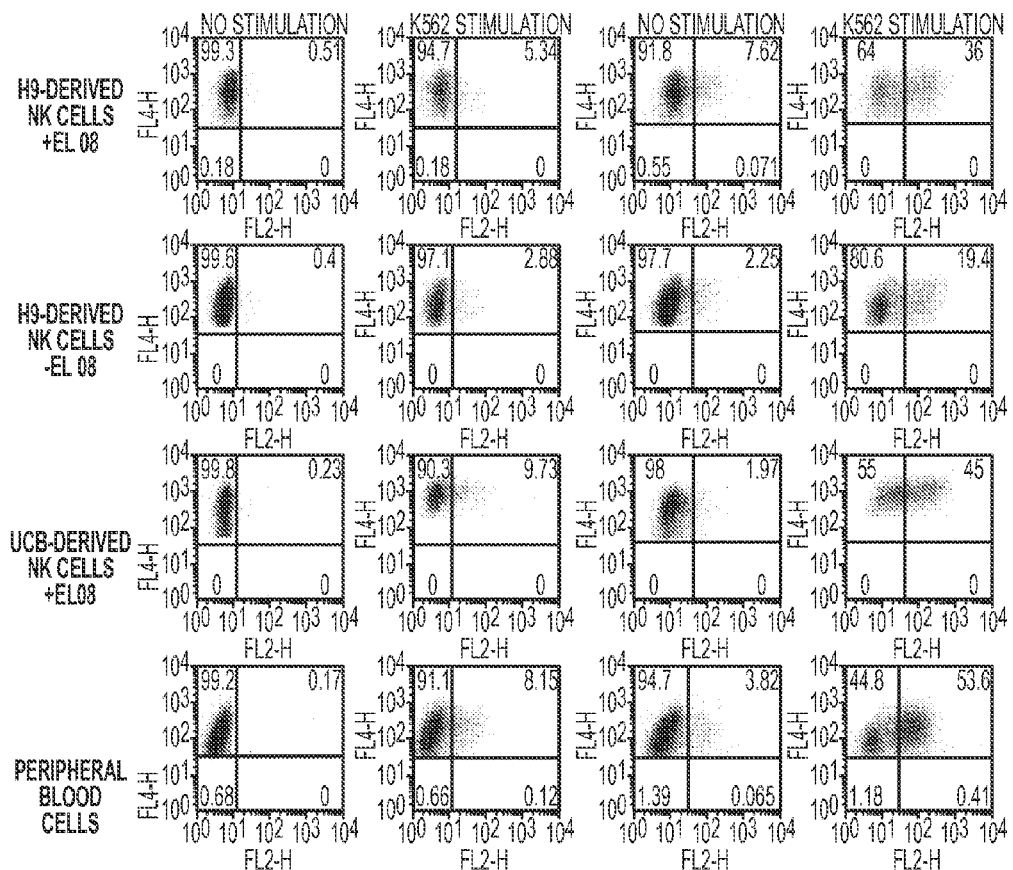
FIG. 13 Spin EB-derived NK cells are functional against a variety of targets. (A) hESC-derived NK cells in feeder or feeder-free conditions, UCB-derived NK cells, and PB-NK cells were tested against K562 targets for IFNγ secretion and CD107a expression. Effectors were incubated with targets for five hours and analyzed by flow cytometry. (B) Each effector population was also tested against myeloma (RPMI 8226, U266, OPM-2) and pancreatic cancer (S2013, S2VP10) targets using a standard $^{51}$Cr release assay. Data are represented as mean±SEM. Abbreviations: IFNγ, interferon γ; NK, natural killer; PB, peripheral blood; UCB, umbilical cord blood.
Figure 13B:
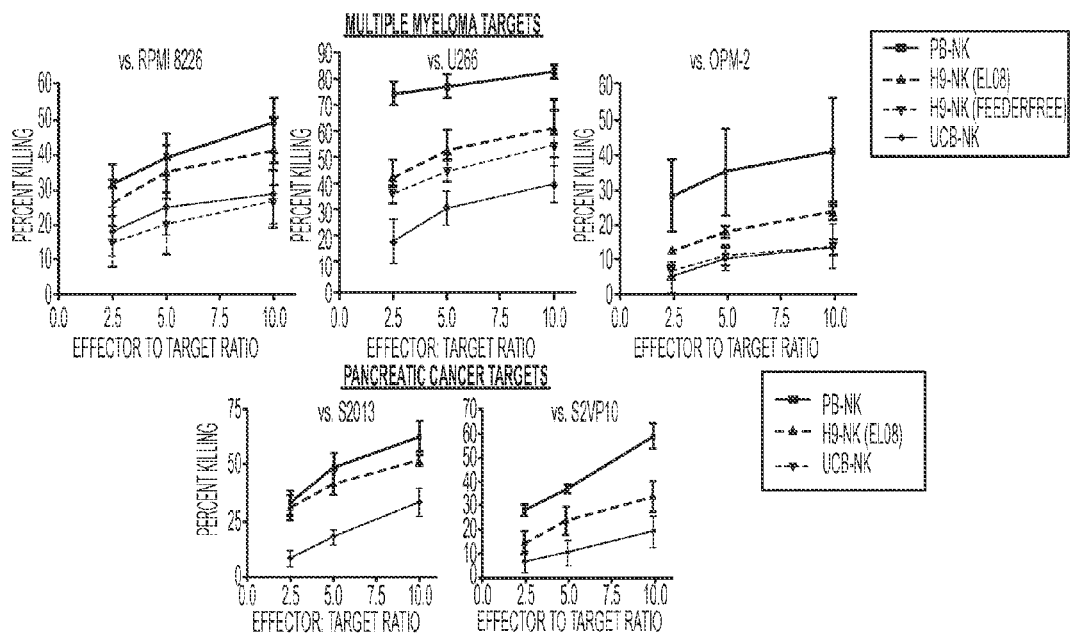

Using these defined conditions with no exogenous stromal cells, NK cells developed in similar numbers and phenotype compared to stage II conditions using the EL08-1D2 stromal cells (FIGS. 10 and 4D). These cells expressed a mature NK cell phenotype and were comparable to their stromal-derived counterparts in cytotoxicity assays, indicating proper NK cell education and acquisition of effector function. Spin EB-derived NK cells degranulated, made IFN-γ, and also had activity against diverse tumor targets including pancreatic cancer and multiple myeloma (FIG. 13). These data demonstrate for the first time, successful in vitro derivation of functional, cytotoxic lymphocytes in the absence of any sorting or murine stromal cell support. Avoiding xenogeneic feeder layers provides a novel, genetically amenable system to study human NK cell education, as well as a defined human source for adoptive immunotherapy.

Clinical-Scale Expansion of hESC-Derived NK Cells for Antitumor Immunotherapy.

Although this EB-based approach shows marked expansion and clinical feasibility, the inventors next aimed to further enhance the number of NK cells generated through another clinically amenable method. Recently, several groups have used aAPCs to expand T cells or NK cells for adoptive immunotherapy (Fujisaki et al., 2009; Denman et al., 2012). One major hindrance of this approach is that high levels of in vitro expansion lead to shortening of telomeres and cellular senescence. Denman et al. have generated an aAPC line expressing membrane bound IL-21 (clone 9.mbIL-21) leading to marked expansion of PB-NK cells while maintaining telomere length and in vitro activity (Denman et al., 2012). The inventors tested whether these aAPCs could lead to further expansion of hESC-derived NK cells and found that clone 9.mbIL-21 aAPCs mediated an additional 2-3 log expansion of both the EL08-1D2 and feeder-free derived NK cells. The aAPC-expanded cells maintained their NK cell phenotype as well as in vitro activity (FIGS. 6B and 6C). Additionally, these hESC-derived NK cells could be maintained and continually expanded in culture for more than two months. Combined, the spin EB method and aAPC expansion provide a straightforward, translatable approach to generate enough human NK cells from hPSCs for cancer immunotherapy.

Example 3

Engineered Human Embryonic Stem Cell-Derived Lymphocytes to Study In Vivo Trafficking and Immunotherapy hESC Maintenance and Hematopoietic Differentiation.

hESCs were maintained on low-density (90,000 cells/well of a six-well plate) mouse embryonic fibroblasts (MEFs). Generation of hematopoietic progenitor cells from hESCs was accomplished using an established method (Ng et al., 2008). To generate spin embryoid bodies (EBs) amenable to aggregation, hESCs and iPSCs were passaged in TrypLE Select (Invitrogen) on low-density MEFs (90,000 cells/well). To follow the hESC-derived NK cells in vivo, we used an H9 line modified with a GFP/firefly luciferease construct (Tian et al., 2009). TrypLE adapted hESCs around 60%-70% confluency were dissociated and filtered through a 70-micron sterile filter. Cells were then counted and placed at a concentration of 3000 cells per well (100 mL volume) of a round-bottom 96-well plate in the BPEL medium containing the stem cell factor (SCF, 40 ng/mL), vascular endothelial growth factor (VEGF, 20 ng/mL), and bone morphogenic protein 4 (BMP4, 20 ng/mL) (Ng et al., 2008). The outer wells of the plate were filled with sterile water to prevent any evaporation of the media. Plates were then spin aggregated at 1,500 RPMs for 5 min at room temperature and placed undisturbed in a 37° C. incubator with 5% $CO_2$.

NK Cell Differentiation from Spin EBs.

At day 11 differentiation, six wells of a 96-well plate were directly transferred to one well of a 24-well plate in NK cell initiating cytokines (IL-3, IL-7, IL-15, SCF, fms-like tyrosine kinase receptor-3 ligand (FLT3L), all from Peprotech) (Woll et al., 2009). NK cell cultures were refreshed with 0.5 mL of cytokine containing media every 4-5 days. Mature NK cells were measured at 28-35 days of culture. Following 4 weeks of NK cell culture, cells were further expanded using artificial antigen presenting cells (aAPCs) (Denman et al., 2012).

Cell Lines.

K562 cells were obtained from American Type Culture Collection (ATCC). K562 cells expressing mbGLuc were generated as follows. First, membrane-bound Gaussia luciferase (mbGluc) was PCR amplified using the following primers: 5'''-CATACA<u>GAATTC</u>ATGGCTCTCCC-AGTGACTGCCCTACTGCTT-3' (SEQ ID NO: 15) and 5'-CATACA<u>GAATTC</u>GGATCCCTATTATTGAATCCGCC-TGTGGTT-3' (SEQ ID NO: 16). EcoRI sites are underlined. The mbGluc fragment was then digested and subcloned in to an EcoR1 digested pKT2-mCAGs-IRES-GFP:zeo construct containing an EcoRI splice junction between the mCAGs promoter and the internal ribosomal entry site (IRES). Orientation was confirmed by restriction enzyme digest at sites within the distal ends of the subcloned mbGluc sequences. To generate turboFP650 expressing K562 cells, we PCR amplified the sequence containing the turboFP650 (Evrogen) as above, using the primers 5'-CATACA<u>ATCGAT</u>ATGGGAGAGGATAGCGA-3' (SEQ ID NO: 17) and 5'-CATACA<u>AGATCT</u>ATCAGTTATCTAGATCC-GGT-3' (SEQ ID NO: 18). ClaI and BglII sites are underlined, respectively. The PCR fragment was then digested with ClaI and BglII and ligated into the pKT2-mbGluc-IRES-GFP:zeo construct in place of the GFP:zeo fusion protein. Confirmed constructs were then nucleofected into K562 cells using a Lonza 4D-nucleofector device. Turbo-FP650 expressing K562 cells were sorted on a FACsAria cell sorter (BD Biosciences).

In Vivo Fluorescent and Bioluminescent Imaging to Follow Trafficking of hESC-Derived NK Cells.

At 24 h before tumor inoculation, 6- to 8-week-old non-obese diabetic/severe combined immunodeficiency with gamma-chain knockout (NOD/SCID/gC$^{-/-}$) mice (Jackson Labs) were given a sublethal dose of irradiation (225-250 cGy). A total of $1\times10^6$ mbGluc+ or mbGluc+/turboFP650+ K562 cells were resuspended in 200 mL of the Iscoves modified Dulbecco's medium (IMDM) (HyClone Laboratories)

supplemented with 20% FBS (Life Technologies). Cells were then injected subcutaneously into the upper left thorax of the mice. The tumors were allowed to engraft for 4 (mbGluc$^+$) or 7 days (turboFP650$^+$). Mice were then given an IP injection of $10\times10^6$ hESC-NK cells resuspended in 300 mL of the IMDM supplemented with 20% FBS. For all experiments, mice receiving no NK cell infusion were included as a negative control and tumor-only mice were included as a positive control for tumor engraftment. All mice received IP injections of IL-2 ($1\times10^4$ U/mouse) and IL-15 (10 ng/mouse) every day for the first 7 days after NK cell injection followed by IL-2 only every 2 to 3 days until mice were sacrificed. All mice were housed, treated, and handled in accordance with the guidelines set forth by the University of Minnesota Institutional Animal Care and Use Committee and the National Institutes of Health's Guide for the Care and Use of Laboratory Animals. To follow tumor progression and NK cell trafficking simultaneously, we utilized two dual-imaging schemes. To track the mbGluc$^+$ K562 cells and Fluc$^+$ hESC-NK cells, bioluminescent imaging was performed using a Xenogen IVIS Spectrum imaging system (Caliper Life Science). Before imaging, mice were anesthetized with isoflurane. A bioluminescent image was acquired using a 1-min exposure 10-15 s following IV injection of coelenterazine (320 mg; Nanolight Technology) or 10 min after IP injection of D-luciferin (150 mg/kg; GOLD Bio Technology). Mice were imaged individually following injection of coelenterazine and allowed to recover before injection of D-luciferin. Optical images were analyzed with Living Image software version 4.2 (Caliper Life Science).

To track turboFP650$^+$ K562 cells and Fluc$^+$ hESC-NK cells, fluorescent and bioluminescent imaging was performed using a Xenogen IVIS Spectrum imaging system. Before imaging, mice were anesthetized as described. A bioluminescent image was acquired for a total 1-min exposure 10 min after IP injection of D-luciferin. Immediately following, a fluorescent imaging sequence was acquired by performing an emission scan for turboFP650 (Excitation: 605, Emission: 660-720) and background signal (Excitation: 570, Emission: 640-720) using autoexposure settings. To separate the tumor and background signal, fluorescent imaging sequences were spectrally unmixed and set to a standard scale using Living Image software version 4.2 (Caliper Life Science).

Immunohistochemistry.

Tumor tissue collected at the time of sacrifice was fixed in 10% formalin for 24-36 h and embedded in paraffin. Four micron sections were cut using a microtome, mounted onto uncharged slides, and rehydrated according to standard protocols. Slides were pretreated with a citrate buffer, 6.0 pH, in a Oster steamer for 30 min, and allowed to cool for 15 min. Primary antibodies were used at the following concentrations: Human NKp46 (R&D Systems; AF1850, 1:100), IgG1 kappa isotype control (eBioscience; Cat #14-4714-82, 1:50). Antibody detection was by horseradish peroxidase-labeled streptavidin and DAB chromagen (Covance). Tissue sections were counterstained in hematoxylin. In every experiment, human tonsil tissue was stained as a positive control and tumor tissue from mice receiving no NK cell injection as a negative control. Images were taken at 10×, 40×, and 63× objective magnifications.

Generation of NK Cells from Luciferase-Expressing hESCs for In Vivo Tracking.

To study lymphocyte trafficking in a mouse xenograft model, the inventors used a well-characterized differentiation protocol to derive NK cells from hESCs (Woll et al., 2005; Ni et al., 2011; Woll et al., 2009). hESC-derived NK cells have a potent antitumor activity both in vitro and in vivo, but tumor clearance had been demonstrated to be a direct result of trafficking NK cells. Using hESCs modified to express firefly luciferase and GFP (Tian et al., 2009), the inventors first demonstrated the ability to differentiate into hematopoietic progenitor cells and subsequently NK cells (FIG. 17). To further explore the function of hESC-derived NK cells in vivo, the inventors developed a model to monitor NK cell persistence and trafficking, as well as tumor burden. The inventors compared the survival of hESC-derived NK cells upon transfer into immunodeficient mice via the IV or IP route. Typically, effector cells for adoptive immunotherapy have been administered IV. For the treatment of leukemia with adoptively transferred NK cells, it is important that these effectors can traffic to sites of tumor involvement, including the spleen and bone marrow. However, this may not be an optimal delivery system for all malignancies, such as ovarian cancer. Additionally, injection of NK cells into a nonhematopoietic or nonlymphoid compartment using an IP approach can provide a more rigorous test of trafficking Mice also received injections of IL-2 (10,000 units/mouse) and IL-15 (10 ng/mouse) for the first 7 days followed by injections of IL-2 (10,000 units/mouse) every other day until the end of the study. Mice receiving IP delivery of NK cells had prolonged persistence compared to those injected IV (FIG. 18). IV delivery of NK cells first trafficked to the lungs of the mice, but were absent by day 4, whereas IP delivery of NK cells lead to persistence for greater than 4 weeks. At day 19, mice were sacrificed and engraftment within the peripheral blood, spleen, bone marrow, and peritoneum was examined. Both routes of NK cell delivery had low levels of engraftment within the peripheral blood, bone marrow, and spleen as measured by GFP$^+$ and CD56$^+$CD45$^+$ cell surface antigens. However, there was a high level of NK cells in the peritoneum of IP injected mice compared to IV injected mice or controls (FIG. 18). This corresponds with the bioluminescent imaging data and led to the conclusion that IP delivery of NK cells allows enhanced persistence of NK cells in vivo and would be optimal for trafficking studies.

NK Cells Persist and Colocalize with Tumors In Vivo.

Next, the inventors took advantage of firefly luciferase stably expressed by our hESC-derived NK cells, as a well-characterized reporter of lymphocyte persistence in vivo (Na et al., 2012; Negrin and Contag, 2006). Previous studies demonstrating the powerful antitumor activity of hESC-derived NK cells in vivo used luciferase-positive tumor cells; however, the inventors were unable to follow NK cells concurrently. To image both NK cells and tumors in the same mouse, the inventors adopted another luciferase reporter of the Gaussia luciferase family. Using a recombinant form of the Gaussia protein that has been modified to be tethered to the membrane (membrane-bound Gaussia luciferase, mbGluc) (Santos et al., 2009), the inventors were able to utilize two different substrates to image both tumors and NK cells in the same mouse. The inventors initially subcloned the mbGluc gene into a Sleeping Beauty backbone driven by an mCAGS promoter. The inventors were able to stably transduce K562 tumor cells and select for cells with the luciferase activity in response to the substrate coelenterazine (activated by Gaussia luciferase), but not luciferin (activated by Firefly luciferase).

Figure 19:
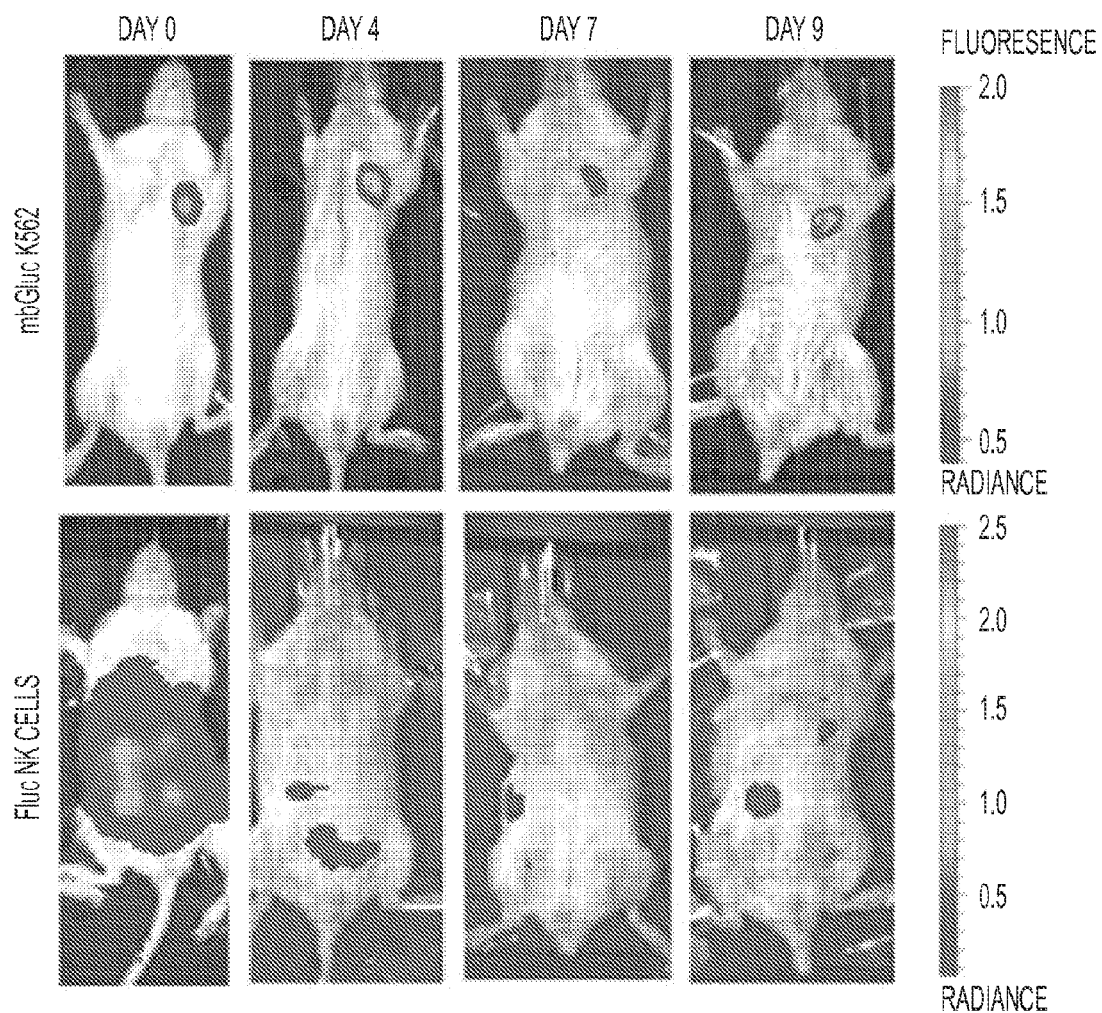
FIG. 19 Dual-bioluminescent imaging to monitor hESC-derived NK cell trafficking in vivo. Monitoring of a single mouse over a period of 9 days for the presence of both tumor cells (mbGluc$^+$, top row) and NK cells (firefly luciferase$^+$, Fluc, bottom row). NK cell trafficking to the tumor site can be seen on day 9 in this particular mouse.

To use both reporters in vivo, the inventors took advantage of the fact that coelenterazine, the substrate for mbGLuc, is rapidly degraded in vivo (Santos et al., 2009). Firefly luciferase (expressed in the hESC-derived NK cells) is reciprocally stable in vivo (Santos et al., 2009; Kim et al., 2010) and was delivered second. Using these two reporters, the inventors were able to initially image mbGluc$^+$ tumor cells, and then image the firefly luc-expressing hESC-derived NK cells in the same mouse. The inventors replicated our initial model by allowing K562 tumor cells to engraft in sublethally irradiated mice for 4 days before NK cell injection (Woll et al., 2009). Because the aim of this study was to study NK cell trafficking, the inventors increased the tumor dose to 1 million cells to better allow tumor growth. The inventors' previous studies, which demonstrated a complete tumor clearance, used a dose of 200,000 cells per mouse. At day 0, NK cells were given IP and mice were treated with cytokines Mice were evaluated for both tumor size and NK cell trafficking at days 0, 4, 7, 9 to 12. Here NK cells were capable of trafficking to tumor sites (FIG. 19). This typically occurred between day 9 and 12, but was variable among mice. Additionally, not every mouse demonstrated trafficking by bioluminescence (4 out of 6 mice showed trafficking) Thus, hESC-derived NK cells can be followed for trafficking in this dual-bioluminescent system. Although not every mouse demonstrated trafficking, this could be due to the absolute number of luciferase+ cells needed to demonstrate the bioluminescent signal and the negative mice could be below the limit of detection. Additionally, increasing the tumor burden of the mice ($1\times10^6$ cells vs. 200,000 cells) was necessary to allow enough NK cells to accumulate and give a bioluminescent signal over background.

Improved Dual Reporter Imaging with Firefly Luciferase and the Fluorescent Protein turboFP650.

Figure 20A:
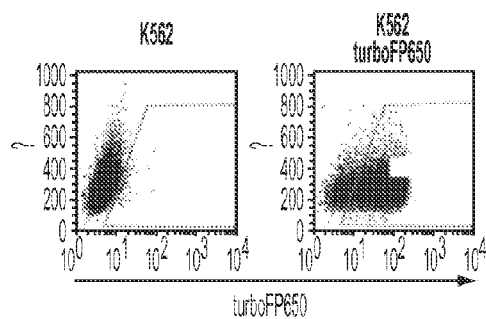
FIG. 20 Enhanced dual-reporter imaging utilizing TurboFP650-expressing K652 cells. (A) K562 cells modified with a TurboFP650 reporter were analyzed and sorted by FACs. (B) Five mice were injected with both TurboFP650$^+$ K562 tumor cells and 10×10$^6$ NK cells and followed for 2 weeks. The images demonstrate trafficking of hESC-derived NK cells expressing firefly luciferase at (B) days 9 and (C) 12. (D) K562 tumor burden was quantified by measuring TurboFP650 signal at days 0, 9, and 12. The NK cell signal (total or trafficked NK cells) was quantified by measuring the firefly luciferase activity. Those NK cells, which had trafficked, were measured by quantifying the amount of NK cell signals colocalizing with the tumor region.
Figures 20B, 20C:
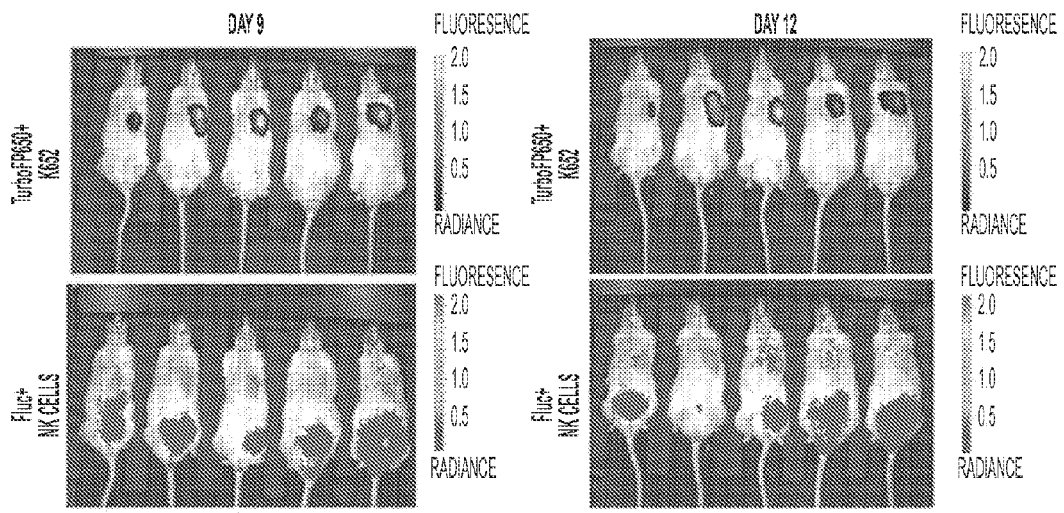
Figure 20D:
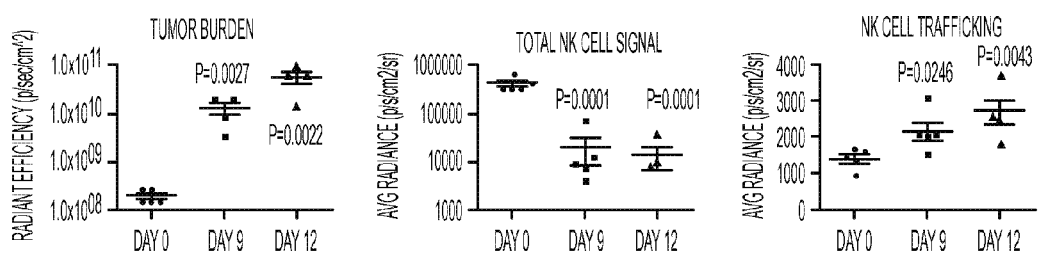

The use of mbGluc in conjunction with firefly luciferase provided a reliable, yet technically challenging model to study NK cell trafficking. This is primarily because the substrate for Gaussia luciferase, coelenterazine, needs to be delivered intravenously. This was difficult for several reasons. First, due to the decay kinetics of the substrate, a limited number of mice could be imaged simultaneously (Santos et al., 2009). Also, repeated injection of the coelenterazine substrate leads to injury of the tail vein over time. To overcome this, the inventors took advantage of a more recently described fluorescent reporter that can be imaged in vivo (Scherbo et al., 2010; Lin et al., 2009). TurboFP650 is a red-shifted fluorescent reporter (excitation 592 nm, emission 650 nm) with tissue penetrance for optimal in vivo imaging. It also does not require delivery of a second substrate. The inventors used a similar cloning approach to express the turboFP650 protein in K562 cells using Sleeping Beauty. Stable expression of TurboFP650 was determined by flow cytometry. Following confirmation of stable transduction for more than 1 week, cells were sorted using the same parameters as above. Sorted cells maintained expression of the TurboFP650 protein and were used for further in vivo studies (FIG. 20).

Using the same in vivo model as above, mice were engrafted with 1 million TurboFP650+ K562 tumor cells and allowed to engraft for 7 days. At day 0, mice were then given firefly luciferase expressing NK cells intraperitoneally and followed for trafficking. Similar to the dual-luciferase studies, NK cells were able to track to turboFP650+tumor cells in four of the five mice, which occurred within 9-12 days post-NK cell injection (FIG. 20). Importantly, the tumor burden and quantity of NK cells can be determined simultaneously. First, turboFP650 provides a reliable in vivo marker of tumor progression. The inventors saw a significant increase in tumor burden in all mice at both days 9 (P=0.0027) and 12 (P=0.0022). The inventors next measured the level of total NK cell signal in each of the mice, and as before, saw that it decreases significantly from day 0 to day 9 (0.0001) or day 12 (P=0.0001). Reciprocally, the inventors saw increased NK cell signal at the site of tumor at day 9 (P=0.0246) and day 12 (P=0.0043), indicating successful trafficking of hESC-derived NK cells to the tumor site. These data support the use of turboFP650 as a reporter compared to mbGluc. By overcoming the technical limitations of using coelenterazine-based reporters, these studies provide an enhanced in vivo system to monitor two cell populations over time.

Trafficking of hESC-Derived NK Cells to Tumor Confirmed by Immunohistochemistry.

Figure 21A:
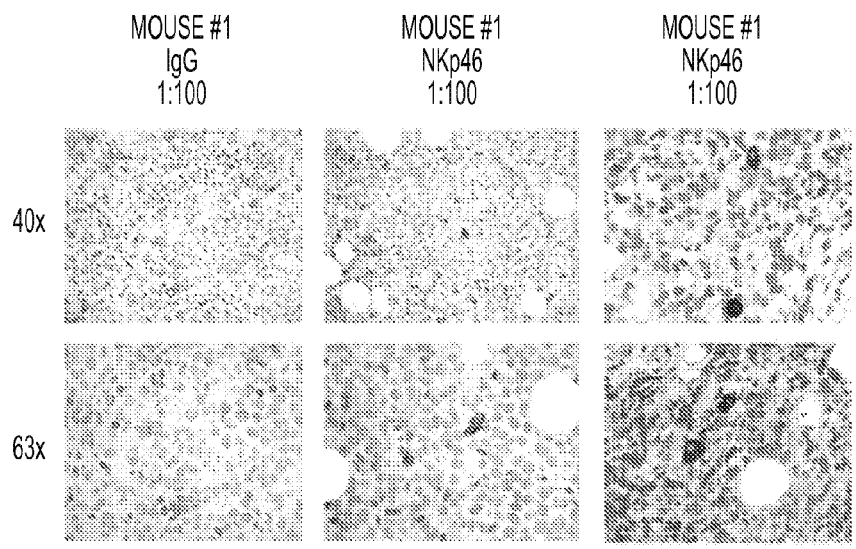
FIG. 21 Immunohistochemical (IHC) confirmation of in vivo NK cell trafficking (A) Tumor tissue from mice with positive trafficking by bioluminescence imaging was formalin fixed and paraffin embedded before IHC. Sections were then stained with isotype (IgG1) or anti-NKp46 antibodies at the indicated concentrations. Isotype and NKp46 antibodies were performed on serial sections. (B) Tumor-only mice demonstrated no staining for NK cells, whereas the positive control, human tonsil tissue (C), had numerous NK cells present.
Figure 21B:
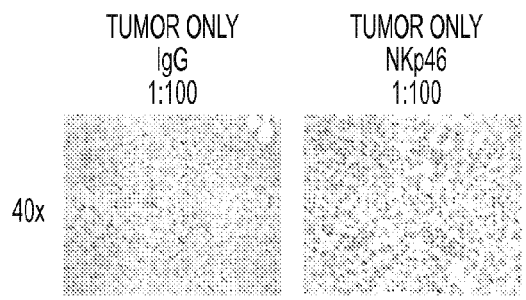
Figure 21C:
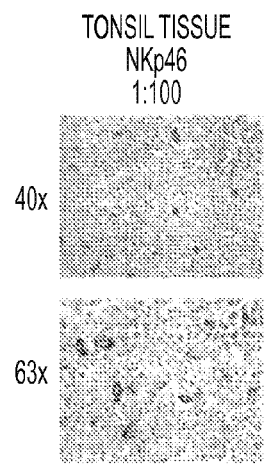

To definitively show NK cells at the tumor site, the inventors more closely examined tumors taken from mice. To confirm the presence of human NK cells at the tumor site, the inventors extracted the tumors, paraffin embedded them, and used immunohistochemistry as a qualitative, confirmatory measure of NK cell trafficking. Compared to the tumor-only (no NK cell injection) group and isotype controls, mice with demonstrated NK cell trafficking by bioluminescent imaging had human NK cells present as demonstrated by NKp46 staining on IHC (FIG. 21). Human tonsil tissue was used as a positive control. NKp46 is a more specific marker of human NK cells, as CD56 can also mark other tissue types. The NK cells positive by IHC staining were uniformly dispersed throughout each tumor tissue section stained, with 15-20 hESC-derived NK cells per section. These data further support the trafficking of NK cells to the tumor site and that bioluminescent imaging using firefly luciferase is an effective model to study lymphocyte trafficking in vivo.

Discussion.

Importantly, these studies were able to demonstrate trafficking of hESC-derived NK cells to the site of tumor and strongly support the hypothesis that hESC/iPSC-derived NK cells directly kill tumor cells in vivo. Without the utility of a dual-bioluminescent imaging model, trafficking would have been much more difficult to discern. Additionally, use of bioluminescent imaging allowed easier and more rapid quantification than IHC. Not all mice grossly demonstrated trafficking by bioluminescent imaging and signs of trafficking ranged over 9-12 days. However, bioluminescent quantification indicates a significant difference in NK cell signal accumulation in the tumor region (FIG. 20). It is possible that some NK cells traffic and are below our limit of detection. Or, NK cells can indeed traffic to tumor, but do not receive the correct signals to stay within the tumor environment. In this case, one could modify the NK cells with tumor-specific receptors to enhance intratumoral persistence and activity (Moon et al., 2011). This has been recently accomplished using chimeric antigen receptors in human T cells (Porter et al., 2011; Carpenito et al., 2009). hESCs and iPSCs provide an optimal platform for such a modification. The studies also confirm our initial findings that unmodified hESC-derived NK cells traffic to tumor sites to clear disease.

Together, these data provide a model system to follow two different populations of human cells in mice and should not be limited to antitumor therapies. The use of two diverse reporter systems combined with hESC/iPSC-derived cells has broad applicability to a number of biological systems. For therapeutic purposes, the ability to derive almost any blood cell from hESCs could provide banks of cells for new therapeutics (Kaufman, 2009). Alternatively, given the relative ease of manufacturing iPSCs and technological advances in this process, the thought of using patient's autologous cells for therapy is also reasonable (Daley, 2007). hPSCs also provide a platform to take gain- and loss-of-function approaches in studying lymphocyte development and trafficking. Constitutive or conditional knock down of particular molecules affecting these processes would be beneficial and a major advantage over using cells isolated from primary sources (HSCs or peripheral blood), which are intrinsically resistant to genetic modification.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,225,042,
U.S. Pat. No. 6,355,476
U.S. Pat. No. 6,362,001
U.S. Pat. No. 6,790,662
U.S. Pat. No. 6,815,450
U.S. Pat. No. 6,943,172
U.S. Pat. No. 7,348,339
U.S. Pat. No. 7,459,424
U.S. Pub. No. 2009/0017000
U.S. Pub. No. 2009/0004142
EP00187371
WO98/30679
WO00/057913
WO00/078351
WO2007/103009
Bashey et al., *Transfusion*, 47(11):2153-60, 2007
Bhardwaj et al., *Nat. Immunol.* 2(2):172-80, 2001.
Bhatia et al., Bone morphogenetic proteins regulate the developmental program of human hematopoietic stem cells. *J. Exp. Med.*, 189(7):1139-48, 1999.
Campana et al. *Cancer Res.* 69(9):4010-4017, 2009.
Carpenito et al., Control of large, established tumor xenografts with genetically retargeted human T cells containing CD28 and CD137 domains. *Proc. Natl. Acad. Sci. USA*, 106:3360-3365, 2009.
Carson et al., A potential role for interleukin-15 in the regulation of human natural killer cell survival. *The Journal of Clinical Investigation*, 99:937-943, 1997.
Chadwick et al., Cytokines and BMP-4 promote hematopoietic differentiation of human embryonic stem cells. *Blood*, 102(3):906-15, 2003.
Cho et al., Expansion and Activation of Natural Killer Cells for Cancer Immunotherapy. *Korean Lab Med.* 29(2): 89-96, 2009.
Choi et al., Hematopoietic and Endothelial Differentiation of Human Induced Pluripotent Stem Cells. *Stem Cells*, 27:559-567, 2009.
Cooley et al., Donor selection for natural killer cell receptor genes leads to superior survival after unrelated transplantation for acute myelogenous leukemia. *Blood*, 116:2411-2419, 2010.
Daley, Towards the generation of patient-specific pluripotent stem cells for combined gene and cell therapy of hematologic disorders. *Am. Soc. Hematol. Educ. Prog.*, 2007:17-22, 2007.
Davidson and Zon, Turning mesoderm into blood: the formation of hematopoietic stem cells during embryogenesis. *Curr. Top. Dev. Biol.*, 50:45-60, 2000.
Davies et al., Specificity and mechanism of action of some commonly used protein kinase inhibitors. *Biochem. J.*, 351 (Pt 1):95-105, 2000.
Denman et al., Membrane-bound IL-21 promotes sustained ex vivo proliferation of human natural killer cells. *PLoS ONE*, 7:e30264, 2012.
Drexler et al., *Growth Factors*, 22(2):71-73, 2004.
Fadilah et al., Cord blood CD34+ cells cultured with FLT3L, stem cell factor, interleukin-6, and IL-3 produce CD11c+ CD1a−/c− myeloid dendritic cells. *Stem Cells, Dev.*, 16(5): 849-55, 2007
Fujisaki et al., Expansion of highly cytotoxic human natural killer cells for cancer cell therapy. *Cancer Research*, 69:4010-4017, 2009.
Galic et al., T lineage differentiation from human embryonic stem cells. *Proc. Natl. Acad. Sci. USA*, 103:11742-11747, 2006.
Gaur et al., Megakaryocytes derived from human embryonic stem cells: a genetically tractable system to study megakaryocytopoiesis and integrin function. *J Thromb Haemost.*, 4(2):436-42, 2006
Hill et al., Human embryonic stem cell-derived vascular progenitor cells capable of endothelial and smooth muscle cell function. *Experimental Hematology*, 38:246-257, 2010.
Huber et al., Cooperative effects of growth factors involved in the induction of hematopoietic mesoderm. *Blood*, 92(11): 4128-37, 1998.
Ikenoya et al., Inhibition of rho-kinase-induced myristoylated alanine-rich C kinase substrate (MARCKS) phosphorylation in human neuronal cells by H-1152, a novel and specific Rho-kinase inhibitor. *J. Neurochem.* 81(1):9-16, 2002.
Kaufman, Toward clinical therapies utilizing hematopoietic cells derived from human pluripotent stem cells. *Blood*, 114:3513-3523, 2009.
Kim et al., Licensing of natural killer cells by host major histocompatibility complex class I molecules. *Nature*, 436: 709-713, 2005.
Kim et al., Non-invasive detection of a small number of bioluminescent cancer cells in vivo. *PLoS One*, 5:e9364, 2010.
Kiselyov et al., *Structure*, 11(6):691-701, 2003.
Knorr and Kaufman, Pluripotent stem cell-derived natural killer cells for cancer therapy. *Translational Research*, 156:147-154, 2010.
Kopher et al., Human embryonic stem cell-derived CD34+ cells function as MSC progenitor cells. *Bone*, 47:718-728, 2010.
Ledran et al., Efficient hematopoietic differentiation of human embryonic stem cells on stromal cells derived from hematopoietic niches. *Cell Stem Cell*, 3:85-98, 2008.
Lin et al., *Int. J. Mol. Med.* 17:833-839, 2006.
Lin et al., Autofluorescent proteins with excitation in the optical window for intravital imaging in mammals. *Chem. Biol.*, 16:1169-1179, 2009.
Ljunggren and Malmberg, Prospects for the use of NK cells in immunotherapy of human cancer. *Nature Reviews Immunology*, 7:329-339, 2007.
Ludwig et al., *Nature Biotech.*, (2):185-187, 2006a.
Ludwig et al., *Nature Methods*, 3(8):637-646, 2006b.
Maekawa et al., *Science*, 285(5429):895-8, 1999.
Marshall et al., *Blood*, 96:1591-1593, 2000.

Miller et al., Successful adoptive transfer and in vivo expansion of human haploidentical NK cells in patients with cancer. *Blood,* 105:3051-3057, 2005.

Moon et al., Expression of a functional CCR2 receptor enhances tumor localization and eradication by human T cells expressing a mesothelin-specific chimeric antibody receptor. *Clin. Cancer Res.,* 17:4719-4730, 2011.

Mrozek et al., Role of interleukin-15 in the development of human CD56+ natural killer cells from CD34+ hematopoietic progenitor cells. *Blood,* 87:2632-2640, 1996.

Na et al., Concurrent visualization of trafficking, expansion, and activation of T lymphocytes and T-cell precursors in vivo. *Blood,* 116:28, 2010.

Negrin and Contag, In vivo imaging using bioluminescence: a tool for probing graft-versus-host disease. *Nature Reviews Immunology,* 6:484-490, 2006.

Ng et al., A protocol describing the use of a recombinant protein-based, animal product-free medium (APEL) for human embryonic stem cell differentiation as spin embryoid bodies. *Nature Protocols,* 3:768-776, 2008.

Ng et al., Forced aggregation of defined numbers of human embryonic stem cells into embryoid bodies fosters robust, reproducible hematopoietic differentiation. *Blood,* 106:1601-1603, 2005.

Ni et al., Human pluripotent stem cells produce natural killer cells that mediate anti-HIV-1 activity by utilizing diverse cellular mechanisms. *Journal of Virology,* 85:43-50, 2011.

Porter et al., Chimeric antigen receptor-modified T cells in chronic lymphoid leukemia. *New Engl. J. Med.,* 365:725-733, 2011.

Ratajczak et al., *Br. J. Haematol.,* 93(4):772-782, 1996.

Robinton and Daley, The promise of induced pluripotent stem cells in research and therapy. *Nature,* 481:295-305, 2012.

Rosenberg et al., Adoptive cell transfer: a clinical path to effective cancer immunotherapy. *Nature Reviews Cancer,* 8:299-308, 2008.

Sadelain et al., The promise and potential pitfalls of chimeric antigen receptors. *Curr. Opin. Immunol.,* 21:215-223, 2009.

Santos et al., Sensitive in vivo imaging of T cells using a membrane-bound Gaussia princeps luciferase. *Nat. Med.,* 15:338-344, 2009.

Sasaki et al. The novel and specific Rho-kinase inhibitor (S)-(+)-2-methyl-1-[(4-methyl-5-isoquinoline)sulfonyl]-homopiperazine as a probing molecule for Rho-kinase-involved pathway. *Pharmacol Ther.* 93(2-3):225-32, 2002.

Schwartz et al., Embryonic stem cell trials for macular degeneration: a preliminary report. *The Lancet,* 379:713-720, 2012.

Shcherbo et al., Near-infrared fluorescent proteins. *Nat. Methods,* 7:827-829, 2010.

Tian et al., Bioluminescent imaging demonstrates that transplanted human embryonic stem cell-derived CD34+ cells preferentially develop into endothelial cells. *Stem Cells,* 27:2675-2685, 2009.

Torikai et al., A foundation for universal T-cell based immunotherapy: T cells engineered to express a CD19-specific chimeric-antigen-receptor and eliminate expression of endogenous TCR. *Blood,* 119:5697-5705, 2012.

Wagemaker et al., *Biotherapy,* 2(4):337-345, 1990.

Woll et al., Human embryonic stem cells differentiate into a homogeneous population of natural killer cells with potent in vivo antitumor activity. *Blood,* 113:6094-6101, 2009.

Woll et al., Human embryonic stem cell-derived NK cells acquire functional receptors and cytolytic activity. Journal of Immunology, 175:5095-5103, 2005.

Yamamura et al., *Stem Cells,* 26(2):543-9, 2008.

What is claimed is:

1. A method for producing natural killer cells from undifferentiated stem cells, the method comprising:
   placing undifferentiated stem cells in a serum-free medium;
   aggregating the undifferentiated stem cells in the serum-free medium and forming spin embryoid bodies by spin aggregation;
   culturing the spin embryoid bodies in the serum-free medium for inducing production of precursor cells from the spin embryoid bodies;
   culturing the precursor cells in a second serum-free medium and in the absence of exogenous stromal cells to produce the natural killer cells from the precursor cells; and
   co-culturing the natural killer cells with inactivated artificial antigen presenting cells (aAPCs).

2. A method for producing natural killer cells from pluripotent stem cells, the method comprising:
   (a) aggregating the pluripotent stem cells in a first serum-free medium, thereby forming embryoid bodies;
   (b) culturing the embryoid bodies in a second serum-free medium, thereby producing hematopoietic progenitor cells; and
   (c) culturing the hematopoietic progenitor cells in a third serum-free medium comprising interleukin 3 (IL-3), interleukin 7 (IL-7), interleukin 15 (IL-15), SCF, and Fms-related tyrosine kinase 3 ligand (FLT3L) and in the absence of exogenous stroma or stromal cells, thereby producing natural killer cells; and
   (d) co-culturing the natural killer cells with inactivated artificial antigen presenting cell (aAPCs).

3. The method according to claim 2, wherein the pluripotent stem cells are human embryonic stem cells (hESCs) or induced pluripotent stem cells (iPSCs).

4. The method according to claim 2, wherein the aggregating is performed by spin aggregation.

5. The method according to claim 2, wherein the second serum-free medium comprises SCF, bone morphogenetic protein 4 (BMP4), and vascular endothelial growth factor (VEGF).

6. The method according to claim 2, wherein the hematopoietic progenitor cells express CD34.

7. The method according to claim 2, wherein the hematopoietic progenitor cells co-express CD34 and CD43.

8. The method according to claim 2, wherein the hematopoietic progenitor cells co-express CD34 and CD45.

9. The method according to claim 2, wherein the method does not include a step of cell sorting between steps (b) and (c).

10. The method according to claim 2, wherein the natural killer cells that are produced express one or more of CD56, killer immunoglobulin-like receptors (KIRs), CD16, NKp44, NKp46, and NKG2D.

11. The method according to claim 2, further comprising co-culturing the natural killer cells with inactivated aAPCs in a medium that comprises interleukin 2 (1L2).

12. An immunotherapeutic method of treating a patient comprising:
   (a) producing a population of natural killer (NK) cells by a method of claim 2; and
   (b) administering an effective amount of said NK cells to a patient in need thereof.

13. The method of claim 12, wherein the patient is a cancer patient.

14. The method of claim 13, wherein the patient has an infectious disease.

15. The method of claim 14, wherein the patient has a viral infection.

16. The method of claim 12, wherein the pluripotent cells are from the patient.

17. An immunotherapeutic method of treating a patient comprising administering an effective amount of natural killer cells produced by a method of claim 2 to a patient in need thereof.

* * * * *

SEQUENCE LISTING

```
<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: Synthetic Primer

<400> SEQUENCE: 1
aaaatgcaga ccgtcaaaaa gga                                            23

<210> SEQ ID NO 2
<211> LENGTH: 23
<212> TYPE: DNA
<213> ORGANISM: Artificial Sequence
<220> FEATURE:
<223> OTHER INFORMATION: Synthetic Primer

<400> SEQUENCE: 2
cttctgacac ttccgttaaa gca                                            23

<210> SEQ ID NO 3
<211> LENGTH: 19
<212> TYPE: DNA
<213> ORGANISM: Artificial Sequence
<220> FEATURE:
<223> OTHER INFORMATION: Synthetic Primer

<400> SEQUENCE: 3
```
tgtgccaact gcacctcaa					19

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
gggattcagg ttccgctctc					20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
gacccgatga gcctgctata c					21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
aatagtggga tgcgagtcca g					21

<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7
tcggaacgca gtctggccat c					21

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
ctcggctgtc tggatgggaa g					21

<210> SEQ ID NO 9
<211> LENGTH: 23
<212> TYPE: DNA
<213> ORGANISM: Artificial Sequence
<220> FEATURE:
<223> OTHER INFORMATION: Synthetic Primer

<400> SEQUENCE: 9
ccagtcccag cttccagtca cag				23

<210> SEQ ID NO 10
<211> LENGTH: 25
<212> TYPE: DNA
<213> ORGANISM: Artificial Sequence

```
<220> FEATURE:
<223> OTHER INFORMATION: Synthetic Primer

<400> SEQUENCE: 10
ggagactcct gaataccttc gtctc                                           25

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer

<400> SEQUENCE: 11
ccccagggcc ccattttggt acc                                             23

<210> SEQ ID NO 12
<211> LENGTH: 26
<212> TYPE: DNA
<213> ORGANISM: Artificial Sequence
<220> FEATURE:
<223> OTHER INFORMATION: Synthetic Primer

<400> SEQUENCE: 12
cttccctcca accagttgcc ccaaac                                          26

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
ccactcctcc acctttgac                                                  19

<210> SEQ ID NO 14
<211> LENGTH: 18
<212> TYPE: DNA
<213> ORGANISM: Artificial Sequence
<220> FEATURE:
<223> OTHER INFORMATION: Synthetic Primer

<400> SEQUENCE: 14
accctgttgc tgtagcca                                                   18

<210> SEQ ID NO 15
<211> LENGTH: 42
<212> TYPE: DNA
<213> ORGANISM: Artificial Sequence
<220> FEATURE:
<223> OTHER INFORMATION: Synthetic Primer

<400> SEQUENCE: 15
catacagaat tcatggctct cccagtgact gccctactgc tt                        42

<210> SEQ ID NO 16
<211> LENGTH: 42
<212> TYPE: DNA
<213> ORGANISM: Artificial Sequence
<220> FEATURE:
<223> OTHER INFORMATION: Synthetic Primer

<400> SEQUENCE: 16
catacagaat tcggatccct attattgaat ccgcctgtgg tt                        42
```

```
<210> SEQ ID NO 17
<211> LENGTH: 29
<212> TYPE: DNA
<213> ORGANISM: Artificial Sequence
<220> FEATURE:
<223> OTHER INFORMATION: Synthetic Primer

<400> SEQUENCE: 17
catacaatcg atatgggaga ggatagcga                                    29

<210> SEQ ID NO 18
<211> LENGTH: 32
<212> TYPE: DNA
<213> ORGANISM: Artificial Sequence
<220> FEATURE:
<223> OTHER INFORMATION: Synthetic Primer

<400> SEQUENCE: 18
catacaagat ctatcagtta tctagatccg gt                                32
```